US006943282B1

(12) United States Patent
Adang et al.

(10) Patent No.: US 6,943,282 B1
(45) Date of Patent: Sep. 13, 2005

(54) INSECT RESISTANT PLANTS

(75) Inventors: Michael J. Adang, Madison, WI (US); John D. Kemp, Las Cruces, NM (US)

(73) Assignee: Mycogen Plant Science, Inc., Indianapolis, IN (US)

(*) Notice: Subject to any disclaimer, the term of this patent is extended or adjusted under 35 U.S.C. 154(b) by 1826 days.

(21) Appl. No.: 07/713,624

(22) Filed: Jun. 10, 1991

Related U.S. Application Data

(63) Continuation of application No. 07/260,574, filed on Oct. 21, 1988, now abandoned, which is a continuation-in-part of application No. 06/848,733, filed on Apr. 4, 1986, now abandoned, which is a continuation-in-part of application No. 06/535,354, filed on Sep. 24, 1983, now abandoned.

(51) Int. Cl.$^7$ .......................... A01H 5/00; C12N 15/82
(52) U.S. Cl. .................. 800/317.4; 800/279; 800/302; 435/418
(58) Field of Search ............................ 435/172.3, 320.1, 435/69.1, 240.4, 418; 800/205, DIG. 42, 43, 44, 56, 27, 302, 317.4, 279

(56) References Cited

U.S. PATENT DOCUMENTS 5,064,648 A * 11/1991 Hickle et al. ............... 435/69.1
5,159,135 A * 10/1992 Umbeck ..................... 800/205
5,254,799 A    10/1993 De Greve et al.
5,317,096 A     5/1994 De Greve et al.

FOREIGN PATENT DOCUMENTS

EP           0193259   *  9/1986   .............. 435/172.3

OTHER PUBLICATIONS

Barton et al (1987) Plant & Physiol. 85: 1103–1109.*
Vasil (Apr. 1988) Biotechnology 6: 397–402.*
Fischhoff et al (1987) Biotechnology 5: 807–813.*
Wong et al (1983) Journal of Biol. Chem. 258 (3): 1960–1967.*
Held et al (1982) Proc. Nat'l Acad. Sci. USA 79: 6065–6069.*
Klier et al (1982) EMBO J. 1: 791–799.*
Bevan et al (1983) Nature 304: 184–187.*
Fraley et al (1983) Proc. Natl. Acad. Sci. USA 80: 4803–4807.*
Herrera–Estrella et al (1983) Nature 303: 209–213.*
Barton et al (1987) Plant & Physiology 85: 1103–1109.*
Brinster et al (Nov. 1981) Cell 27: 223–231.*
Thorne et al (Jun. 1986) Journal of Bacteriology 166 (3): 801–811.*
Hofte et al (Jun. 1989) Microbiological Reviews 53(2): 242–255.*
Vaeck et al (Jul. 1987) Nature 328: 33–37.*
Jordon et al (1988) Plant Cell Reports 7: 285–287.*
Gelvin (1987) Plant Molecular Biology 8: 355–359.*
Thorne, et al. (Jun. 1986) Journal of Bacteriology 166 (3): 801–811.*
Hofte, et al (Jun. 1989) Microbiological Reviews 53(2): 242–255.*
Vaeck, et al (Jul. 1987) Nature 328: 33–37.*
Vasil (Apr. 1988) Biotechnology 6: 397–402.*
Fischhoff, et al (1987) Biotechnology 5: 807–813.*
Wong, et al (1983) Journal of Biol. Chem. 258(3): 1960–1967.*
Held, et al (1982) Proc. Natl. Acad. Sci, USA 79: 6065–6069.*
Klier, et al (1982) EMBO J. 1: 791–799.*
Fischhoff et al. (1987) Biotechnology 5:807–813.
DeGreve et al., EPO publication No. 0,193,259, published Mar. 9, 1986.
Gengenbach et al., Proc. Natl. Acad. Sci U.S.A. 74(11): 5113–5117 (1977).
Hibberd et al., Proc. Natl. Acad. Sci. U.S.A. 79: 559–563 (1982).
Green et al., Maize for Biological Research, ed. W.F. Sheridan, p. 367–371 Plant Molecular Biology Association (1982).

* cited by examiner

Primary Examiner—Anne Kubelik
(74) Attorney, Agent, or Firm—Saliwanchik, Lloyd & Saliwanchik

(57) ABSTRACT

A method for expressing insecticidal protein structural genes in plant genomes is provided. In the preferred embodiments this invention comprises placing a structural gene for the *Bacillus thuringiensis* crystal protein under control of a plant or a T-DNA promoter and ahead of a polyadenylation site followed by insertion of said promoter/structural gene combination into a plant genome by utilizing an *Agrobacterium tumefaciens* Ti plasmid-based transformation system. The modified Ti plasmid is then used to transform recipient plant cells. Also provided are the plants and tissues produced by this method and bacterial strains, plasmids, and vectors useful for execution of this invention.

23 Claims, 4 Drawing Sheets

Partial Sequence of the Crystal Protein Gene

```
AAGTGGATTTTATATATAAGTATAAAAAGTAATAAGACTTTAAAATAAGTTAACGGAATACAAACCCTTAATGCATTGGTTAAACATTGTAAAGTCTAAA 100

GCATGCATAATGGGCGAGAAGTAAGTAGATTGTTAACACCCTGGGTCAAAAATTGATATTTAGTAAAATTAGTTGCACTTTGTGCATTTTTTGATAAGAT 200

GAGTCATATGTTTTAAATTGTAGTAATGAAAAACAGTATTATATCATAATGAATTGGTATCTTAATAAAAGAGATGGAGGTAACTTATGGATAACAATCC 300
                                                                                      MetAspAsnAsnPr

GAACATCAATGAATGCATTCCTTATAATTGTTTAAGTAACCCTGAAGTAGAAGTATTAGGTGGAGAAAGAATAGAAACTGGTTACACCCCAATCGATATT 400
oAsnIleAsnGluCysIleProTyrAsnCysLeuSerAsnProGluValGluValLeuGlyGlyGluArgIleGluThrGlyTyrThrProIleAspIle

TCCTTGTCGCTAACGCAATTTCTTTTGAGTGAATTTGTTCCCGGTGCTGGATTTGTGTTAGGACTAGTTGATATAATATGGGGAATTTTTGGTCCCTCTC 500
SerLeuSerLeuThrGlnPheLeuLeuSerGluPheValProGlyAlaGlyPheValLeuGlyLeuValAspIleIleTrpGlyIlePheGlyProSerG

AATGGGACGCATTTCTTGTACAAATTGAACAGTTAATTAACCAAAGAATAGAAGAATTCGCTAGGAACCAAGCCATTTCTAGATTAGAAGGACTAAGCAA 600
lnTrpAspAlaPheLeuValGlnIleGluGlnLeuIleAsnGlnArgIleGluGluPheAlaArgAsnGlnAlaIleSerArgLeuGluGlyLeuSerAs

TCTTTATCAAATTTACGCAGAATCTTTTAGAGAGTGGGAAGCAGATCCTACTAATCCAGCATTAAGAGAAGAGATGCGTATTCAATTCAATGACATGAAC 700
nLeuTyrGlnIleTyrAlaGluSerPheArgGluTrpGluAlaAspProThrAsnProAlaLeuArgGluGluMetArgIleGlnPheAsnAspMetAsn

AGTGCCCTTACAACCGCTATTCCTCTTTTTGCAGTTCAAAATTATCAAGTTCCTCTTTTATCAGTATATGTTCAAGCTGCAAATTTACATTTATCAGTTT 800
SerAlaLeuThrThrAlaIleProLeuPheAlaValGlnAsnTyrGlnValProLeuLeuSerValTyrValGlnAlaAlaAsnLeuHisLeuSerValL

TGAGAGATGTTTCAGTGTTTGGACAAAGGTGGGGATTTGATGCCGCGACTAGCAATAGTCGTTATAATGATTTAACTAGGCTTATTGGCAACTATACAGA 900
euArgAspValSerValPheGlyGlnArgTrpGlyPheAspAlaAlaThrSerAsnSerArgTyrAsnAspLeuThrArgLeuIleGlyAsnTyrThrAs

TTATGCTGTACGCTGGTACAATACGGGATTAGAACGTGTATGGGGACCGGATTCTAGAGATTGGGTAAGGTATAATCAATTTAGAAGAGAATTAACACTA 1000
pTyrAlaValArgTrpTyrAsnThrGlyLeuGluArgValTrpGlyProAspSerArgAspTrpValArgTyrAsnGlnPheArgArgGluLeuThrLeu

ACTGTATTAGATATCGTTGCTCTGTTCCCGAATTATGATAGTAGAAGATATCCAATTCGAACAGTTTCCCAATTAACAAGAGAAATTTATACAAACCCAG 1100
ThrValLeuAspIleValAlaLeuPheProAsnTyrAspSerArgArgTyrProIleArgThrValSerGlnLeuThrArgGluIleTyrThrAsnProV

TATTAGAAAATTTTGATGGTAGTTTTCGAGGCTCGGCTCAGGGCATAGAAAGAAGTATTAGGAGTTCACATTTGATGGATATACTTAACAGTATAACCAT 1200
alLeuGluAsnPheAspGlySerPheArgGlySerAlaGlnGlyIleGluArgSerIleArgSerSerHisLeuMetAspIleLeuAsnSerIleThrIl

CTATACGGATGCTCATAGGGGTTATTATTATTGGTCAGGGCATCAAATAATGGCTTCTCCTGTAGGGTTTTCGGGGCCAGAATTCACTTTTCCGCTATAT 1300
eTyrThrAspAlaHisArgGlyTyrTyrTyrTrpSerGlyHisGlnIleMetAlaSerProValGlyPheSerGlyProGluPheThrPheProLeuTyr

GGAACTATGGGAAATGCAGCTCCACAACAACGTATTGTTGCTCAACTAGGTCAGGGCGTGTATAGAACATTATCGTCCACTTTATATAGAAGACCTTTTA 1400
GlyThrMetGlyAsnAlaAlaProGlnGlnArgIleValAlaGlnLeuGlyGlnGlyValTyrArgThrLeuSerSerThrLeuTyrArgArgProPheA

ATATAGGGATAAATAATCAACAACTATCTGTTCTTGACGGGACAGAATTTGCTTATGGAACCTCCTCAAATTTGCCATCCGCTGTATACAGAAAAAGCGG 1500
snIleGlyIleAsnAsnGlnGlnLeuSerValLeuAspGlyThrGluPheAlaTyrGlyThrSerSerAsnLeuProSerAlaValTyrArgLysSerGl
```

FIG. 1 - 2

INSECT RESISTANT PLANTS

This is a continuation of application Ser. No. 07/260,574, filed Oct. 21, 1988 now abandoned.

This is a continuation-in-part of co-pending application Ser. No. 06/848,733, filed Apr. 4, 1986 now abandoned, a continuation-in-part application of application Ser. No. 06/535,354, filed Sep. 24, 1983, now abandoned, both of which are incorporated herein by reference.

FIELD OF THE INVENTION

The present invention is in the fields of genetic engineering, plant husbandry, and bacterial bio-affecting compositions, especially those derived from the genus Bacillus.

BACKGROUND OF THE INVENTION

Insecticidal Protein

*Bacillus thuringiensis*, a species of bacteria closely related to *B. cereus*, forms a proteinacious crystalline inclusion during sporulation. This crystal is parasporal, forming within the cell at the end opposite from the developing spore. The crystal protein, often referred to as the delta-endotoxen, has two forms: a nontoxic protoxin of approximate molecular weight (MW) of 130 kilodaltons (kD), and a toxin having an approx. MW of 67 kD. The crystal contains the protoxin protein which is activated in the gut of larvae of a number of insect species. Klowden, M. J. et al. (1983) Appl. Environ. Microbiol. 46:312–315, have shown solubilized protoxin from *B. thuringiensis* var. *israelensis* is toxic to *Aedes aegypti* adults. During activation, the protoxin is cleaved into two polypeptides, one or both of which are toxic. In vivo, the crystal is activated by being solubilized and converted to toxic form by the alkalinity and proteases of the gut. In vitro the protoxin may be solubilized by extremely high pH (e.g., pH 12), by reducing agents under moderately basic conditions (e.g., pH 10), or by strong denaturants (guanidium, urea) under neutral conditions (pH 7), and once solubilized, may be activated by the action of the protease trypsin. The crystal protein is reported to be antigenically related to proteins within both the spore coat and the vegetative cell wall. Carbohydrate is not involved in the toxic properties of the protein.

*B. thuringiensis* and its crystalline endotoxin are useful because the crystal protein is an insecticidal protein known to be poisonous to the larvae of over a hundred of species of insects, most commonly those from the orders Lepidoptera and Diptera. Insects susceptible to the action of the *B. thuringiensis* crystal protein include, but need not be limited to, those listed in Table 1. Many of these insect species are economically important pests. Plants which can be protected by application of the crystal protein include, but need not be limited to, those listed in Table 2. Different varieties of *B. thuringiensis*, which include, but need not be limited to, those listed in Table 3, have different host ranges (Faust R. M. et al. (1982) in *Genetic Engineering in the Plant Sciences*, Panapolous, N.J. (ed.) pp. 225–254); this probably reflects the toxicity of a given crystal protein in a particular host. The crystal protein is highly specific to insects; in over two decades of commercial application of sporulated *B. thuringiensis* cells to crops and ornamentals there has been no known case of effects to plants or noninsect animals. The efficacy and safety of the endotoxin have been reviewed by Faust, R. M. et al., supra. Other useful reviews include those by Fast, P. G. (1981) in *Microbial Control of Pests and Plant Diseases*, 1970–1980, Burges H. D. (ed.), pp. 223–248; and Huber, H. E. and Luthy, P. (1981) in *Pathogenesis of Invertebrate Microbial Diseases*, Davidson, E. W. (ed.), pp. 209–234.

The crystal protein gene usually can be found on one of several large plasmids that have been found in *Bacillus thuringiensis*, though in some strains it may be located on the chromosome (Kronstad, J. W. et al. (1983) J. Bacteriol. 154:419–428). Several of the genes have been cloned into plasmids that can grow in *E. coli*. Whiteley's group (Whiteley, H. R. et al. (1982) in Molecular Cloning and gene Regulation in Bacilli, Ganesan, A. T. et al (eds.), pp. 131–144; Schnepf, H. E. and Whiteley, H. R. (1981) Proc. Natl. Acad. Sci. USA 78:2893–2897; and European pat. application 63,949) reported the cloning of the toxin from *B. thuringiensis* var. *kurstaki* strains HD-1-Dipel and HD-73, using the enzymes Sau3AI (under partial digest conditions) and BglII, respectively, to insert large gene-bearing fragments having approximate sizes of 12 kbp and 16 kbp into the BamHI site of the *E. coli* plasmid vector pBR322. The HD-1 crystal protein was observed to be located on a 6.6 kilobase pair (kbp) HindIII fragment. Crystal protein from the HD-1-Dipel gene which was toxic to larvae, immunologically identifiable, and the same size as authentic protoxin, was observed to be produced by transformed *E. coli* cells containing pBR322 clones or subclones. This indicated that the Bacillus gene was transcribed, probably from its own promoter, and translated in *E. coli*. Additionally, this suggests that the toxic activity of the protein product is independent of the location of its synthesis. That the gene was expressed when the fragment containing it was inserted into the vector in either orientation suggests that transcription was controlled by its own promoter. The transcriptional and translational start sites, as well as the deduced sequence for the amino-terminal 333 amino acids of the HD-1-Dipel protoxin, have been determined by nucleic acid sequencing (Wong, H. C. et al. (1983) J. Biol. Chem. 258:1960–1967). The insecticidal gene was found to have the expected bacterial ribosome binding and translational start (ATG) sites along with commonly found sequences at −10 and −35 (relative to the 5'-end of the mRNA) that are involved in initiation of transcription in bacteria such as *B. subtilis*. Klier, A. et al. (1982) EMBO J. 1:791–799, have reported the cloning of the crystal protein gene from *B. thuringiensis* strain berliner 1715 in pBR322. Using the enzyme BamHI, a large 14 kbp fragment carrying the crystal protein gene was moved into the vector pHV33, which can replicate in both *E. coli* and Bacillus. In both *E. coli* and sporulating *B. subtilis*, the pHV33-based clone directed the synthesis of full-size (130 kD) protoxin which formed cytoplasmic inclusion bodies and reacted with antibodies prepared against authentic protoxin. Extracts of *E. coli* cells harboring the pBR322 or pHV33-based plasmids were toxic to larvae. In further work, Klier, A. et al. (1983) Nucl. Acids Res. 11:3973–3987, have transcribed the berliner crystal protein gene in vitro and have reported on the sequence of the promoter region, together with the first 11 codons of the crystal protein. The bacterial ribosome binding and translational start sites were identified. Though the expected "−10" sequence was identified, no homology to other promoters has yet been seen near −35. Held et al. (1982) Proc. Natl. Acad. Sci. USA 77:6065–6069 reported the cloning of a crystal protein gene from the variety *kurstaki* in the phage g-based cloning vector Charon4A. *E. coli* cells infected with one of the Charon clones produced antigen that was the same size as the protoxin (130 kD) and was toxic to larvae. A 4.6 kbp EcoRI fragment of this Charon clone was moved into pHV33 and an *E. coli* plasmid vector, pBR328. Again, 130 kD antigenically identifiable crystal protein was produced by both *E. coli* and *B. subtilis* strains harboring the appropriate plasmids. A *B. thuringiensis* chromosomal sequence which cross-hybridized with the cloned crystal protein gene was identified in *B. thuringiensis* strains which do not produce crystal protein during sporulation.

In addition to the crystal protein, *B. thuringiensis* produces at least three other toxins. Two of them, the heta-exotoxin and gamma-exotoxin, are phospholipase enzymes that degrade lipids. *B. cereus* is also known to produce phospholipases (or lecithinases) which are toxic to insect larvae. Other bacterial enzymes which are involved in insect pathogenesis include, but need not be limited to, hyaluronidases, phosphatases, and proteases. Protease produced by *Pseudomonas aeruginosa* has been shown to have a specific affinity to proteins of *Galleria mellonella* larvae (see Lysenko, O. and Kucera, M. (1971) in Microbial Control of Insects and Mites, Burges, H. D. and Hussey, N. W. (eds.), pp. 205–227).

Chang, S. (1983) Trends Biotechnol. 1:100–101, reported that the DNA sequence of a complete HD-1 gene had been publicly presented (ref. 5 therein), and that the HD-1 toxin moiety resides in the amino-terminal 67 kD peptide.

Shuttle Vectors

Shuttle vectors, developed by Ruvkun, G. B. and Ausubel, F. M. (1981) Nature 298:85–88, provide a way to insert foreign genetic materials into position of choice in a large plasmid, virus, or genome. There are two main problems encountered when dealing with large plasmids or genomes. Firstly, the large plasmids may have many sites for each restriction enzyme. Unique site-specific cleavage reactions are not reproducible and multi-site cleavage reactions followed by ligation lead to great difficulties due to the scrambling of the many fragments whose order and orientation one does not want changed. Secondly, the transformation efficiency with large DNA plasmids is very low. Shuttle vectors allow one to overcome these difficulties by facilitating the insertion, often in vitro, of the foreign genetic material into a smaller plasmid, then transferring, usually by in vivo techniques, to the larger plasmid.

A shuttle vector consists of a DNA molecule, usually a plasmid, capable of being introduced into the ultimate recipient bacteria. It also includes a copy of the fragment of the recipient genome into which the foreign genetic material is to be inserted and a DNA segment coding for a selectable trait, which is also inserted into the recipient genome fragment. The selectable trait ("marker") is conveniently inserted by transposon mutagenesis or by restriction enzymes and ligases.

The shuttle vector can be introduced into the ultimate recipient cell, typically a bacterium of the family Rhizobiaceae (which contains the genus Agrobacterium), by a tri-parental mating (Ruvkin and Ausubel, supra), direct transfer of a self-mobilizable vector in a bi-parental mating, direct uptake of exogenous DNA by Agrobacterium cells ("transformation," using the conditions of Holsters, M. et al. (1978) Mol. Gen. Genet. 163:181–187), by spheroplast fusion of Agrobacterium with another bacterial cell, by uptake of liposome-encapsulated DNA, or infection with a shuttle vector that is based on a virus that is capable of being packaged in vitro. A tri-parental mating involves the mating of a strain containing a mobilizable plasmid, which carries genes for plasmid mobilization and conjugative transfer, with the strain containing the shuttle vector. If the shuttle vector is capable of being mobilized by the plasmid genes, the shuttle vector is transferred to the recipient cell containing the large genome, e.g., the Ti or Ri plasmids of Agrobacterium strains.

After the shuttle vector is introduced into the recipient cell, possible events include a double crossover with one recombinational event on either side of the marker. This event will result in transfer of a DNA segment containing the marker to the recipient genome replacing a homologous segment lacking the insert. To select for cells that have lost the original shuttle vector, the shuttle vector must be incapable of replicating in the ultimate host cell or be incompatible with an independently selectable plasmid pre-existing in the recipient cell. One common means of arranging this is to provide in the third parent another plasmid which is incompatible with the shuttle vector and which carries a different drug resistance marker. Therefore, when one selects for resistance to both drugs, the only surviving cells are those in which the marker on the shuttle vector has recombined with the recipient genome. If the shuttle vector carries an extra marker, one can then screen for and discard cells that contain plasmids resulting from a single crossover event between the shuttle vector and the recipient plasmid resulting in cointegrates in which the entire shuttle vector is integrated with the recipient plasmid. If the foreign genetic material is inserted into or adjacent to the marker that is selected for, it will also be integrated into the recipient plasmid as a result of the same double recombination. It might also be carried along when inserted into the homologous fragment at a spot not within or adjacent to the marker, but the greater the distance separating the foreign genetic material from the marker, the more likely will be a recombinational event occurring between the foreign genetic material and marker, preventing transfer of the foreign genetic material.

If the shuttle vector is used to introduce a phenotypically dominant trait (e.g., a novel expressible insecticide structural gene, but not an inactivated oncogenic T-DNA gene) one need not rely on a double homologous recombination. The cells resulting from a single cross-over event resulting in cointegrate plasmids can transfer the desired trait into plant cells. One may even use a variant shuttle vector having a single uninterrupted sequence of T-DNA. However, as the resulting T-DNA will now contain a tandem duplication, one must be vigilant regarding a possible rare deletion of the shuttle vector by a single homologous recombination event occurring between the two homologous sequences in either the Agrobacterium or plant cells.

Shuttle vectors have proved useful in manipulation of Agrobacterium plasmids: see Garfinkel, D. J. et al. (1981) Cell 27:143–153; Matzke, A. J. M. and Chilton, M-D. (1981) J. Mol. Appl. Genet. 1:39–49; and Leemans, J. et al. (1981) J. Mol. Appl. Genet. 1:149–164, who referred to shuttle vectors by the term "intermediate vectors."

A recently disclosed variation of the shuttle vector system for inserting changes into large DNA molecules is the "suicide vector." In this system, as described by Puhler, A. et al., U.S. Pat. No. 4,626,504 and Simon, R. et al. (November 1983) "A Broad Host Range Mobilization System for In Vivo Genetic Engineering: Transposon Mutagenesis in Gram negative Bacteria," Biotechnology, pp. 784–791, the shuttle vector is incapable of being maintained within the recipient cell. This property eliminates the need to introduce an incompatible plasmid into the recipient cell in order to exclude the shuttle vector as is commonly done during a triparental mating. All vectors which do not integrate into some already present DNA effectively "commit suicide" by not being replicated. As can be done with traditional types of shuttle vectors, one may distinguish between double and single homologous recombination by screening for an antibiotic resistance gene which is not between the two regions of homology. Use of a pBR322-based suicide vector to transfer DNA sequences into a Ti plasmid has been reported by Van Haute, E. et al. (1983) EMBO J. 2:411–417, and Comai, L. et al. (1982) Plant Mol. Biol. 1:291–300.

An alternative to the use of shuttle vectors for introduction of novel DNA sequences into T-DNA by means of homologous recombination involves bacterial transposons. As described in the section Agrobacterium-Genes on the TIP Plasmids, transposons can "jump" into the T-DNA of a TIP plasmid (e.g., see Garfinkel, D. J. et al. (1981) Cell 27:143–153). Should the transposon be modified in vitro by the insertion of the novel sequence, that novel DNA can be transferred into the TIP plasmid's T-DNA by the transposon. The TIP can then transfer the novel DNA/transposon/T-DNA combination to a plant cell where it will be stably integrated.

Agrobacterium-overview

Included within the gram-negative bacterial family Rhizobiaceae in the genus Agrobacterium are the species *A. tumefaciens* and *A. rhizogenes*. These species are respectively the causal agents of crown gall disease and hairy root disease of plants. Crown gall is characterized by the growth of a gall of dedifferentiated tissue. Hairy root is a teratoma characterized by inappropriate induction of roots in infected tissue. In both diseases, the inappropriately growing plant tissue usually produces one or more amino acid derivatives, known as opines, not normally produced by the plant which are catabolized by the infecting bacteria. Known opines have been classified into three main families whose type members are octopine, nopaline, and agropine. The cells of inappropriately growing tissues can be grown in culture, and, under appropriate conditions, be regenerated into whole plants that retain certain transformed phenotypes.

Virulent strains of Agrobacterium harbor large plasmids known as Ti (tumor-inducing) plasmids in *A. tumefaciens* and Ri (root-inducing) plasmids in *A. rhizogenes*. Curing a strain of these plasmids results in a loss of pathogenicity. The Ti plasmid contains a region, referred to as T-DNA (transferred-DNA), which in tumors is found to be integrated into the genome of the host plant. The T-DNA encodes several transcripts. Mutational studies have shown that some of these are involved in induction of tumorous growth. Mutants in the genes for tml, tmr, tms, respectively result in large tumors (in tobacco), a propensity to generate roots, and a tendency for shoot induction. The T-DNA also encodes the gene for at least one opine synthase, and the Ti plasmids are often classified by the opine which they caused to be synthesized. Each of the T-DNA genes is under control of a T-DNA promoter. The T-DNA promoters resemble eukaryotic promoters in structure, and they appear to function only in the transformed plant cell. The Ti plasmid also carries genes outside the T-DNA region. These genes are involved in functions which include opine catabolism, oncogenicity, agrocin sensitivity, replication, and autotransfer to bacterial cells. The Ri plasmid is organized in a fashion analogous to the Ti plasmid. The set of genes and DNA sequences responsible for transforming the plant cell are hereinafter collectively referred to as the transformation-inducing principle (TIP). The designation TIP therefore includes both Ti and Ri plasmids. The integrated segment of a TIP is termed herein "T-DNA" (transferred DNA), whether derived from a Ti plasmid or an Ri plasmid.

Chilton, M-D. (June 1983) Sci. Amer. 248(6):50–59, has recently provided an introductory article on the use of. Ti plasmids as vectors. Recent general reviews of Agrobacterium-caused disease include those by Merlo, D. J. (1982) Adv. Plant Pathol. 1:139–178; Ream, L. W. and Gordon, M. P. (1982) Science 218:854–859; and Bevan, M. W. and Chilton, M-D. (1982) Ann. Rev. Genet. 16:357–384; Kahl, G. and Schell, J. (1982) *Molecular Biology of Plant Tumors*, and Barton, K. A. and Chilton, M-D. (1983) Methods Enzymol. 101:527–539.

Agrobacterium-Infection of Plant Tissues

Plant cells can be transformed by Agrobacterium in a number of methods known in the art which include, but are not limited to, co-cultivation of plant cells in culture with Agrobacterium, direct infection of a plant, fusion of plant protoplasts with Agrobacterium spheroplasts, direct transformation by uptake of free DNA by plant cell protoplasts, transformation of protoplasts having partly regenerated cell walls with intact bacteria transformation of protoplasts by liposomes containing T-DNA, use of a virus to carry in the T-DNA, microinjection, and the like. Any method will suffice as long as the gene is reliably expressed, and is stably transmitted through mitosis and meiosis.

The infection of plant tissue by Agrobacterium is a simple technique well-known to those skilled in the art (for an example, see Butcher, D. N. et al. (1980) in *Tissue Culture Methods for Plant Pathologists*, Ingram, D. S. and Helgeson. J. P. (eds.), pp. 203–208). Typically a plant is wounded by any of a number of ways, which include cutting with a razor, puncturing with a needle, or rubbing with abrasive. The wound is then inoculated with a solution containing tumor-inducing bacteria. An alternative to the infection of intact plants is the inoculation of pieces of tissues such as potato tuber disks (Anand, D. K. and Heberlein, G. T. (1977) Amer. J. Both. 64:153–158) or segments of tobacco stems (Barton, K. A. et al. (1983) Cell 32:1033–1043). After induction, the tumors can be placed in tissue culture on media lacking phytohormones. Hormone independent growth is typical of transformed plant tissue and is in great contrast to the usual conditions of growth of such tissue in culture (Braun, A. C. (1956) Cancer Res. 16:53–56).

Agrobacterium is also capable of infecting isolated cells and cells grown in culture (Marton, L. et al. (1979) Nature 277:129–131) and isolated tobacco mesophyll protoplasts. In the latter technique, after allowing time for partial regeneration of new cell walls, Agrobacterium cells were added to the culture for a time and then killed by the addition of antibiotics. Only those cells exposed to *A. tumefaciens* cells harboring the Ti plasmid were capable of forming calli when plated on media lacking hormone. Most calli were found to contain an enzymatic activity involved in opine anabolism other workers (Horsch, R. B. and Fraley, R. T. (18 Jan. 1983) 15th Miami Winter Symposium) have reported transformations by co-cultivation, leading to a high rate (greater than 10%) of calli displaying hormone-independent growth, with 95% of those calli making opines. Davey, M. R. et al. (1980) in Ingram and Helgeson, supra, pp. 209–219, describe the infection of older cells that had been regenerated from protoplasts.

Plant protoplasts can be transformed by the direct uptake of TIP plasmids. Davey, M. R. et al. (1980) Plant Sci. Lett. 18:307–313, and Davey, M. R. et al. (1980) in Ingram and Helgeson, supra, were able to transform Petunia protoplasts with the Ti plasmid in the presence of poly-L-α-ornithine to a phenotype of opine synthesis and hormone-independent growth in culture. It was later shown (Draper, J. et al. (1982) Plant and Cell Physiol. 23:451–458; Davey, M. R. et al. (1982) in *Plant Tissue Culture*, 1982, Fujiwara, A. (ed.), pp. 515–516) that polyethylene glycol-stimulated Ti plasmid uptake and that some T-DNA sequences were integrated into the genome. Krens, F. A. et al. (1982) Nature 296:72–74, reported similar results using polyethylene glycol following by a calcium shock, though their data suggests that the integrated T-DNA included flanking Ti plasmid sequences.

An alternative method to obtain DNA uptake involves the use of liposomes. The preparation of DNA containing liposomes is taught by Papahadjopoulos in U.S. Pat. Nos. 4,078,052 and 4,235,871. Preparations for the introduction of Ti-DNA via liposomes have been reported (Nagata, T. et al. (1982) in Fujiwara, supra, pp. 509–510; and Nagata, T. (1981) Mol. Gen. Genet. 184:161–165). An analogous system involves the fusion of plant and bacterial cells after removal of their cell walls. An example of this technique is the transformation of Vinca protoplast by Agrobacterium spheroplasts reported by Hasezawa, S. et al. (1981) Mol. Gen. Genet. 182:206 210. Plant protoplasts can take up cell wall delimited Agrobacterium cells (Hasezawa, S. et al. (1982) in Fujiwara, supra pp. 517–518).

T-DNA can be transmitted to tissue regenerated from a fusion of two protoplasts, only one of which had been transformed (Wullems, G. J. et al. (1980) Theor. Appl. Genet. 56:203–208). As detailed in the section on Regeneration of Plants, T-DNA can pass through meiosis and be transmitted to progeny as a simple Mendelian trait.

Agrobacterium—Regeneration of Plants

Differentiated plant tissues with normal morphology have been obtained from crown gall tumors. Braun, A. C. and Wood, H. N. (1976) Proc. Natl. Acad. Sci. USA 73:496–500, grafted tobacco teratomas onto normal plants and were able to obtain normally appearing shoots which could flower. The shoots retained the ability to make opines and to grow independently of phytohormones when placed in culture. In the plants screened, these tumorous phenotypes were not observed to be transmitted to progeny, apparently being lost during meiosis (Turgeon, R. et al. (1976) Proc. Natl. Acad. Sci. USA 73:3562–3564). Plants which had spontaneously lost tumorous properties, or which were derived from teratoma seed, were initially shown to have lost all their T-DNA (Yang, F-M. et al. (1980) In Vitro 16:87–92; Yang, F. et al. (1980) Mol. Gen. Genet. 177:707–714; Lemmers, M. et al. (1980) J. Mol. Biol. 144:353–376). However, later work with plants that had become revertants after hormone treatment (1 mg/l kinetin) showed that plants which had gone through meiosis, though losing T-DNA genes responsible for the transformed phenotype, could retain sequences homologous to both ends of T-DNA (Yang, F. and Simpson, R. B. (1981) Proc. Natl. Acad. Sci. USA 78:4151–4155). Wullems, G. J. et al. (1981) Cell 24:719–724, further demonstrated that genes involved in opine anabolism were capable of passing through meiosis though the plants were male sterile and that seemingly unaltered T-DNA could be inherited in a Mendelian fashion (Wullems, G. J. et al. (1982) in Fujiwara, supra). Otten, L. et al. (1981) Mol. Gen. Genet. 183:209–213, used Tn7 transposon-generated Ti plasmid mutants in the tms (shoot-inducing) locus to create tumors which proliferated shoots. When these shoots were regenerated into plants, they were found to form self-fertile flowers. The resultant seeds germinated into plants which contained T-DNA and made opines. In further experiments, DeGreve, H. et al. (1982) Nature 300:752–755, have found that octopine synthase can be inherited as a single dominant Mendelian gene. However, the T-DNA had sustained extensive deletions of functions other than ocs while undergoing regeneration from callus. Similar experiments with a tmr (root-inducing) mutant showed that full-length T-DNA could be transmitted through meiosis to progeny, that in those progeny nopaline genes could be expressed, though at variable levels, and that co-transformed yeast alcohol dehydrogenase I gene was not expressed (Barton, K. A. et al. (1983) Cell 32:1033–1043). It now appears that regenerated tissues which lack T-DNA sequences are probably descended from untransformed cells which "contaminate" the tumor (Ooms, G. et al. (1982) Cell 30:589–597). Recent work by Binns, A. N. (1983) Planta 158:272–279, indicates that tumorogenic genes, in this case tmr, can be "shut off" during regeneration and "turned back on" by placing regenerated tissue in culture.

Roots resulting from transformation from A. rhizogenes have proven relatively easy to regenerate directly into plantlets (Chilton, M-D. et al. (1982) Nature 295:432–434.

Agrobacterium-Genes on the TIP Plasmids

A number of genes have been identified within the T-DNA of the TIP plasmids. About half a dozen octopine plasmid T-DNA transcripts have been mapped (Gelvin, S. B. et al. (1982) Proc. Natl. Acad. Sci. USA 79:76–80; Willmitzer, L. et al. (1982) EMBO J. 1:139–146) and some functions have been assigned (Leemans, J. et al. (1982) EMBO J. 1:147–152). Some of these transcripts, specifically those in the region encoding tmr and tms, can also be transcribed in prokaryotic cells (Schroder, G. et al. (1983) EMBO J. 2:403–409). The four genes of an octopine type plasmid that have been well defined by transposon mutagenesis include tms, tmr, and tml (Garfinkel, D. J. et al. (1981) Cell 27:143–153). Ti plasmids which carry mutations in these genes respectively incite tumorous calli of Nicotiana tabacum which generate shoots, proliferate roots, and are larger than normal. In other hosts, mutants of these genes can induce different phenotypes (see Bevan, M. W. and Chilton, M-D. (1982) Ann. Rev. Genet. 16:357–384). The phenotypes of tms and tmr are correlated with differences in the phytohormone levels present in the tumor. The differences in cytokinin:auxin ratios are similar to those which in culture induce shoot or root formation in untransformed callus tissue (Akiyoshi, D. E. et al. (1983) Proc. Natl. Acad. Sci. USA 80:407–411). T-DNA containing a functional gene for either tms or tmr alone, but not functional tml alone, can promote significant tumor growth. Promotion of shoots and roots is respectively stimulated and inhibited by functional tml (Ream, L. W. et al. (1983) Proc. Natl. Acad. Sci. USA 80:1660–1664). Mutations in T-DNA genes do not seem to affect the insertion of T-DNA into the plant genome (Leemans, et al. (1982) supra; Ream, et al. (1983) supra). The ocs gene encodes octopine synthase, which has been sequenced by De Greve, H. et al. (1982) J. Mol. Appl. Genet. 1:499–511. It does not contain introns (intervening sequences commonly found in eukaryotic genes which are post transcriptionally spliced out of the messenger precursor during maturation of the mRNA). It does have sequences that resemble a eukaryotic transcriptional signal ("TATA box") and a polyadenylation site. All of the signals necessary for expression of the ocs gene are found within 295 bp of the ocs transcriptional start site (Koncz, C. et al. (1983) EMBO J. 2:1597–1603).

Nopaline Ti plasmids encode the nopaline synthase gene (nos), which has been sequenced by Depicker, A. et al. (1982) J. Mol. Appl. Genet. 1:561–573. As was found with the ocs gene, nos is not interrupted by introns. It has two putative polyadenylation sites and a potential "TATA box." In contrast to ocs, nos is preceded by a sequence which may be a transcriptional signal known as a "CAT box." All of the signals necessary for expression of the nos gene are found within 261 bp of the nos transcriptional start site (Koncz, C. et al., supra). A gene for agrocinopine synthase and genes equivalent to tms and tmr have been identified on a nopaline-type plasmid (Joos, H. et al. (1983) Cell 32:1057–1067), and a number of transcripts have been mapped (Willmitzer, L. et al. (1983) Cell 32:1045–1056). McPhersson, J. C. et al. (1980) Proc. Natl. Acad. Sci. USA 77:2666–2670, reported the in vitro translation of T-DNA encoded mRNAs from crown gall tissues.

Transcription from hairy root T-DNA has also been detected (Willmitzer, L. et al. (1982) Mol. Gen. Genet. 186:16–22). Functionally, the hairy root syndrome appears to be equivalent of a crown gall tumor incited by a Ti plasmid mutated in tmr (White, F. F. and Nester, E. W. (1980) J. Bacteriol. 144:710–720.

In eukaryotes, methylation (especially of cytosine residues) of DNA is correlated with transcriptional inactivation; genes that are relatively under methylated are transcribed into mRNA. Gelvin, S. B. et al. (1983) Nucl. Acids Res. 11:159–174, has found that the T-DNA in crown gall tumors is always present in at least one unmethylated copy. That the same genome may contain numerous other copies of T-DNA which are methylated suggests that the copies of T-DNA in excess of one may be biologically inert. (See also Ooms, G. et al. (1982) Cell 30:589–597.)

The Ti plasmid encodes other genes which are outside of the T-DNA region and are necessary for the infection process. (See Holsters, M. et al. (1980) Plasmid 3:212–230 for nopaline plasmids, and De Greve H., et al. (1981) Plasmid 6:235–248; Garfinkel, D. J. and Nester, E. W. (1980) J. Bacteriol. 144:732–743; and Ooms, G. (1980) J. Bacteriol. 144:82–91 for octopine plasmids). Most important are the onc genes, which when mutated result in Ti plasmids incapable of oncogenicity. (These loci are also known as vir, for virulence.) Several onc genes have been accurately mapped and have been found to be located in regions conserved among various Ti plasmids (Klee, H. J. et al. (1983) J. Bacteriol. 153:878–883; Iyer, V. N. et al. (1982) Mol. Gen. Genet. 188:418–424). The onc genes function in trans, being capable of causing the transformation of plant cells with T-DNA of a different plasmid type and physically located on another plasmid (Hille, J. et al. (1982) Plasmid 7:107 118; Klee, H. J. et al. (1982) J. Bacteriol. 150:327–331; de Framond, A. J. et al. (1983) Biotechnol. 1:262–269). Nopaline Ti DNA has direct repeats of about 25 base pairs immediately adjacent to the left and right borders of the T-DNA which might be involved in either excision from the Ti plasmid or integration into the host genome (Yadav, N. S. et al. (1982) Proc. Natl. Acad. Sci. USA 79:6322–6326), and a homologous sequence has been observed adjacent to an octopine T-DNA border (Simpson, R. B. et al. (1982) Cell 29:1005–1014). Opine catabolism is specified by the occ and noc genes, respectively, of octopine- and nopaline-type plasmids. The Ti plasmid also encodes functions necessary for its own reproduction including an origin of replication. Ti plasmid transcripts have been detected in A. tumefaciens cells by Gelvin, S. B. et al. (1981) Plasmid 6:17–29, who found that T-DNA regions were weakly transcribed along with non-T-DNA sequences. Ti plasmid-determined characteristics have been reviewed by Merlo, (1082) supra (see especially Table II), and Ream and Gordon (1982) supra.

Agrobacterium-TIP Plasmid DNA

Different octopine-type Ti plasmids are nearly 100% homologous to each other when examined by DNA hybridization (Currier, T. C. and Nester, E. W. (1976) J. Bacteriol. 126:157–165) or restriction enzyme analysis (Sciaky, D. et al. (1978) Plasmid 1:238–253). Nopaline-type Ti plasmids have as little as 67% homology to each other (Currier and Nester, (1976) supra). A survey revealed that different Ri plasmids are very homologous to each other (Costantino, P. et al. (1981) Plasmid 5:170–182). Drummond, N. H. and Chilton, M-D. (1978) J. Bacteriol. 136:1178–1183, showed that proportionally small sections of octopine- and nopaline-type Ti plasmids were homologous to each other. These homologies were mapped in detail by Engler, G. et al. (1981) J. Mol. Biol. 152:183–208. They found that three of the four homologous regions were subdivided into three (overlapping the T-DNA), four (containing some onc genes), and nine (having onc genes) homologous sequences. The uninterrupted homology contains at least one tra gene (for conjugal transfer of the Ti plasmid to other bacterial cells), and genes involved in replication and incompatibility. This uninterrupted region has homology with a Sym plasmid (involved in symbiotic nitrogen fixation) from a species of Rhizobium, a different genus in the family Rhizobiaceae (Prakash, R. K. et al. (1982) Plasmid 7:271–280). The order of the four regions is not conserved, though they are all oriented in the same direction. Part of the T-DNA sequence is very highly conserved between nopaline and octopine plasmids (Chilton, M-D. et al. (1978) Nature 275:147–149; Depicker, A. et al. (1978) Nature 275:150–153). Ri plasmids have been shown to have extensive homology among themselves, and to both octopine (White, F. F. and Nester, E. W. (1980) J. Bacteriol. 144:710–720) and nopaline (Risuleo, G. et al. (1982) Plasmid 7:45–51) Ti plasmids, primarily in regions encoding onc genes. Ri T-DNA contains extensive though weak homologies to T-DNA from both types of Ti plasmid (Willmitzer, L. et al. (1982) Mol. Gen. Genet. 186:16–22). Plant DNA from uninfected Nicotiana glauca contains sequences, referred to as cT-DNA (cellular T-DNA), that show homology to a portion of the Ri T-DNA (White, F. F. et al. (1983) Nature 301:348–350; Spano, L. et al. (1982) Plant Mol. Biol. 1:291–300). Huffman, G. A. et al. (1983) J. Bacteriol., have mapped the region of cross-hybridization and have shown that Ri plasmid, pRiA4b, is more closely related to a pTiA6 (octopine-type) than pTiT37 (nopaline-type) and that this Ri plasmid appears to carry sequence homologous to tms but not tmr. Their results also suggested that Ri T-DNA may be discontinuous, analogous to the case with octopine T-DNA.

It has been shown that a portion of the Ti (Chilton, M-D. et al. (1977) Cell 11:263–271) or Ri (Chilton, M-D. (1982) Nature 295:432–434; White, F. F. et al. (1982) Proc. Natl. Acad. Sci. USA 79:3193–3197; Willmitzer, L. (1982) Mol. Gen. Genet. 186:16–22) plasmid is found in the DNA of tumorous plant cells. The transferred DNA is known as T-DNA. T-DNA is integrated into the host DNA (Thomashow, M. F. et al. (1980) Proc. Natl. Acad. Sci. USA 77:6448 6452; Yadav, N. S. et al. (1980) Nature 287:458–461) in the nucleus (Nuti, M. P. et al. (1980) Plant Sci. Lett. 18:1–6; Willmitzer, L. et al. (1980) Nature 287:359–361; Chilton, M-D. et al. (1980) Proc. Natl. Acad. Sci. USA 77:4060 4064).

Thomashow, M. F. et al. (1980) Proc. Natl. Acad. Sci. USA 77:6448–6452; and Thomashow, M. F. et al. (1980) Cell 19:729–739, found the T-DNA from octopine-type Ti plasmids to have been integrated in two separate sections, TL-DNA and TR-DNA, left and right T-DNAs respectively. The copy numbers of TR and TL can vary (Merlo, D. J. et al. (1980) Mol. Gen. Genet. 177:637–643). A core of T-DNA is highly homologous to nopaline T-DNA (Chilton et al. (1978) supra, and Depicker et al. (1978) supra), is required for tumor maintenance, is found in TL, is generally present in one copy per cell, and codes for the genes tms, tmr, and tml. On the other hand TR can be totally dispensed with (De Beuckeleer, M. et al. (1981) Mol. Gen. Genet. 183:283–288; Ooms, G. et al. (1982) Cell 30:589–597), though found in a high copy number (Merlo et al. (1980) supra). Ooms, G. et al. (1982) Plasmid 7:15–29, hypothesized that TR is involved in T-DNA integration, though they find that when TR is deleted from the Ti plasmid, *A. tumfaciens* does retain some virulence. Ooms, G. et al. (1982) Cell 30:589–597, showed that though T-DNA is occasionally deleted after integration in the plant genome, it is generally stable and that tumors containing a mixture of cells that differ in T-DNA organization are the result of multiple transformation events. The ocs is found in TL but can be deleted from the plant genome without loss of phenotypes related to tumorous growth. The left border of integrated TL has been observed to be composed of repeats of T-DNA sequences which are in either direct or inverted orientations (Simpson, R. B. et al. (1982) Cell 29:1005–1014).

In contrast to the situation in octopine-type tumors, nopaline T-DNA is integrated into the host genome in one continuous fragment (Lemmers, M. et al. (1980) J. Mol. Biol. 144:353–376; Zambryski, P. et al. (1980) Science 209:1385–1391). Direct tandem repeats were observed. T-DNA of plants regenerated from teratomas had minor modifications in the border fragments of the inserted DNA (Lemmers et al., supra). Sequence analysis of the junction between the right and left borders revealed a number of direct repeats and one inverted repeat. The latter spanned the junction (Zambryski, et al. (1980) supra). The left junction has been shown to vary by at least 70 base pairs while the right junction varies no more than a single nucleotide (Zambryski, P. et al. (1982) J. Mol. Appl. Genet. 1:361–370). Left and right borders in junctions of tandem arrays were separated by spacers which could be over 130 bp. The spacers were of unknown origin and contained some T-DNA sequences. T-DNA was found to be integrated into both repeated and low copy number host sequences. H. Joos et al. (1983) Cell 32:1057–1067, have shown that virulence is not eliminated after deletion of either of the usual nopaline T-DNA borders.

Simpson et al. (1982) supra, and Zambryski et al. (1980) supra have suggested that direct repeats in the border regions are involved in integration of T-DNA into plant DNA. That T-DNA having borders from two different Ti plasmids are less specifically integrated than are homologous borders supports this suggestion (Ooms, G. et al. (1982) Plant Mol. Biol. 1:265–276).

Yadav, N. S. et al. (1982) Proc. Natl. Acad. Sci. USA 79:6322–6326, have found a chi site, which in the bacteriophage (greek symbol) augments general recombination in the surrounding DNA as far as 10 kilobases away, in a nopaline Ti plasmid just outside the left end of the T-DNA. Simpson, R. B. et al. (1982) Cell 29:1005–1014, have not observed a chi sequence in an octopine Ti plasmid, though the possible range of action does not eliminate the possibility of one being necessary and present but outside of the region sequenced. The significance of the chi in the Ti plasmid is not known. If the chi has a function, it is probably used in Agrobacterium cells and not in the plants, as chi is not found within the T-DNA.

Agrobacterium-Manipulations of the TIP Plasmids

As de tailed in the section on Shuttle Vectors, technology has bee n developed for the introduction of altered DNA sequences into desired locations on a TIP plasmid. Transposons can be easily inserted using this technology (Garfinkel, D. J. et al. (1981) Cell 27:143–153). Hernalsteen, J-P. et al. (1980) Nature 287:654–656, have shown that a DNA sequence (here a bacterial transposon) inserted into T-DNA in the Ti plasmid is transferred and integrated into the recipient plant's genome. Though insertion of foreign DNA has been done with a number of genes from different sources, to date foreign genes have not usually been expressed under control of their own promoters. Sources of these genes include alcohol dehydrogenase (Adh) from yeast (Barton, K. A. et al. (1983) Cell 32:1033–1043), AdhI (Bennetzen, J., unpublished) and zein from corn, interferon and globin from mammals, and the mammalian virus SV40 (Schell, J., unpublished). However, when the nopaline synthase gene was inserted into octopine T-DNA and transformed into plant tissue, it was found to be fully functional (Fink, C. L. (1982) M. S. thesis, University of Wisconsin-Madison). The gene encoding phaseolin, the storage protein found in seeds of the bean *Phaseolus vulgaris* L., has been transferred into and expressed in sun flower tumors. This latter work constitutes the first example of a transferred plant gene being expressed under control of its own promoter in foreign plant tissue. Transcription started and stopped at the correct positions, and introns were post-transcriptionally processed properly (Hall, T. C. et al., U.S. application Ser. No. 485,613, which is hereby incorporated by reference). Holsters, M. et al. (1982) Mol. Gen. Genet. 185:283–289, have shown that a bacterial transposon (Tn7) inserted into T-DNA could be recovered in a fully functional and seemingly unchanged form after integration into a plant genome.

Deletions can be generated in a TIP plasmid by several methods. Shuttle vectors can be used to introduce deletions constructed by standard recombinant DNA techniques (Cohen and Boyer, U.S. Pat. No. 4,237,224). Deletions with one predetermined end can be created by the improper excision of transposons (Koekman, B. P. et al. (1979) Plasmid 2:347–357, and Ooms, G. et al. (1982) Plasmid 7:15–29). Hille, J. and Schilperoot, R. (1981) Plasmid 6:151–154, have demonstrated that deletions having both ends at predetermined positions can be generated by use of two transposons. The technique can also be used to construct "recombinant DNA" molecules in vivo.

The nopaline synthase gene has been used for insertion of DNA segments coding for drug resistance that can be used to select for transformed plant cells. In plant cells, the kanamycin resistance gene from Tn5 is not transcribed under control of its own promoter (Kemp, J. D. et al. (18 May 1982) Beltsville Symp. VII, Beltsville, Md., (1983) in *Genetic Engineering: Applications to Agriculture*, Owens, L. D. (ed.) and; Fink, C. L. (1982) supra). Bevan, M. W. et al. (1983) Nature 340:184–187 and Fraley, R. T. et al. (1983) Proc. Natl. Acad. Sci. USA 80:4803–4807, have inserted the kanamycin resistance gene (neomycin phosphotransferase II) from Tn5 behind (i.e., under control of) the nopaline promoter. The construction was used to transform plant cells which in culture displayed resistance to kanamycin and its analogs such as G418. Schell, J. et al. (18 Jan. 1983) 15th Miami Winter Symp. (see also Marx, J. L. (1983) Science 219:830), reported a similar construction, in which the methotrexate resistance gene (dihydrofolate reductase) from Tn7 was placed behind the nopaline synthase promoter. Transformed cells were resistant to methotrexate. Similarly, Herrera-Estrella, L. et al. (1983) Nature 303:209–213, have obtained expression in plant cells of enzymatic activity for octopine synthase and chloramphenicol acetyltransferase, an enzyme which in bacteria confers resistance to chloramphenicol, by placing the structural genes for these two enzymes under control of nos promoters.

Hall, T. C. et al., U.S. application Ser. No. 485,614, which is hereby incorporated by reference, have fused the ocs promoter and the 5' end of the octopine synthase structural gene to the structural gene for the bean seed protein phaseolin. A fusion protein having the amino terminus of octopine synthase and lacking the amino terminus of phaseolin was produced under control of the T-DNA promoter. The introns, which were contributed by the phaseolin sequences, were post-transcriptionally processed properly.

de Framond, A. J. et al. (1983) Biotechnol. 1:262–269, have reported on the construction a "mini-Ti plasmid." In the nopaline T-DNA there is normally only one site cut by the restriction enzyme KpnI. A mutant lacking the site was constructed and a KpnI fragment, containing the entire nopaline T-DNA, was isolated. This fragment together with a kanamycin resistance gene was inserted into pRK290, thereby resulting in a plasmid which could be maintained in *A. tumfaciens* and lacked almost all non-T-DNA Ti sequences. By itself, this plasmid was not able to transform plant cells. However when placed in an *A. tumefaciens* strain containing an octopine Ti plasmid, tumors were induced which synthesized both octopine and nopaline. The mini-Ti plasmid has also been transferred into plant cells when complemented with a Ti plasmid deleted for its own T-DNA. These results indicated that the non-T-DNA functions acted in trans with T-DNA, that the missing nopaline Ti plasmid functions were complemented by the octopine Ti plasmid, and that the nopaline "mini-Ti" was functional in the transformation of plant cells. A similar pair of complementing plasmids, each containing either octopine T-DNA or onc genes, has been constructed by Hoekema, A. et al. (1983) Nature 303:179–180.

Chilton et al. (18 Jan. 1983) 15th Miami Winter Symp., also reported on the construction of a "micro-Ti" plasmid made by resectioning the mini-Ti with SmaI to delete essentially all of T-DNA but the nopaline synthase gene and the left and right borders. The micro-Ti was inserted into a modified pRK290 plasmid that was missing its SmaI site, and was employed in a manner similar to mini-Ti, with comparable results.

SUMMARY OF THE INVENTION

One object of this invention is to confer pest resistance, specifically insect resistance, to a plant. In pursuance of this goal, other objects are to stably insert a gene coding for an insecticidal protein into the genome of the plant cell, to have this gene expressed in plant tissues, for the expression to be either regulated or constitutive, and for the plant tissues to be in a normal plant. Another object is to provide novel specialized insecticidal tissues for a plant, in particular to provide a means for producing on a normal plant, preferably a dicot a gall which contains within its tissue an insecticidal protein. Other objects and advantages will become evident from the following description.

The invention disclosed herein provides a plant comprising a genetically modified plant cell having an insecticide structural gene introduced and expressed therein under control of a plant expressible promoter. Further, the invention provides plant tissue comprising a plant cell whose genome includes T-DNA comprising an insecticide structural gene inserted in such orientation and spacing with respect to a plant expressible promoter as to be expressible in the plant cell under control of that promoter. Also provided are novel strains of bacteria containing and replicating T-DNA, as defined herein, the T-DNA being modified to contain an inserted insecticide structural gene in such orientation and spacing with respect to a plant expressible promoter as to be expressible in a plant cell under control of said promoter. Further, the invention provides novel plasmids having the ability to replicate in *E. coli* and comprising T-DNA, and further comprising an insecticide structural gene inserted within T-DNA contained within the plasmid, in such manner as to be expressible in a plant cell under control of a plant expressible promoter. Additionally, this invention discloses novel plasmids wherein the insecticide structural gene is capable of expression in *E. coli* or *Bacillus subtillis*, and furthermore discloses strains of bacteria harboring said bacterial expression plasmids.

The invention is exemplified in one of its embodiments by the insertion of the full length structural gene of *Bacillus thuringiensis* insect toxic protein into a sub-Ti plasmid so that the toxin gene is placed under the control of T-DNA plant active regulation sequences (ORF24). The sub-Ti plasmid containing the plant expressible crystal protein gene was introduced into tobacco cells. Tobacco and tomato plants regenerated from these transformed cells were found to express crystal protein at levels measurable by ELISA techniques but also the leaves of these plants were found to be toxic to insect larvae.

The present invention comprises an insecticide structural gene under control of a promoter expressible in plant cells, said promoter/gene combination being inserted into a plant cell by any means known to the art. More specifically, in its preferred embodiment the invention disclosed herein further comprises expression in plant cells of an insecticide structural gene under control of a plant expressible promoter, after introduction via T-DNA, that is to say, by inserting the insecticide structural gene into T-DNA under control of a plant expressible promoter and introducing the T-DNA containing the insert into a plant cell using known means.

The invention is useful for genetically modifying plant tissues and whole plants by inserting useful insecticide structural genes from various bacterial species or strains. Such useful insecticide structural genes include, but are not limited to, the genes coding for insecticidal proteins as defined below, especially the crystal protein of *Bacillus thuringiensis*, related proteins, and the like. Truncated and modified genes, for example as described in U.S. patent application Ser. No. 617,321 incorporated herein by reference, and synthetic genes, for example as described in U.S. patent application Ser. No. 242,482 incorporated herein by reference, may also be used. The invention is exemplified by introduction and expression of structural genes for a crystal protein from *B. thuringiensis* var. *kurstaki* HD-73 or *B. thuringiensis* var. *tenebrionis* into cotton, tobacco, potato, tomato and maize plant cells. Once plant cells expressing an insecticide structural gene under control of a plant expressible promoter are obtained, plant tissues and whole plants can be regenerated therefrom using methods and techniques well-known in the art. The regenerated plants are then reproduced by conventional means and the introduced genes can be transferred to other strains and cultivars by conventional plant breeding techniques.

The introduction and expression of the structural gene for an insecticidal protein can be used to protect a crop from infestation with insect larvae such as hornworm (*Manduca* sp.) or European corn borer (*Ostrinia nubilalis*). Other uses of the invention, exploiting the properties of other insecticide structural genes introduced into other plant species will be readily apparent to those skilled in the art. The invention in principle applies to any introduction of an insecticide structural gene into any plant species into which foreign DNA (in the preferred embodiment T-DNA) can be introduced and in which said DNA can remain stably replicated. In general these taxa presently include, but are not limited to, gymnosperms and dicotyledonous plants, such as sunflower (family Compositeae), tobacco (family Solanaceae), alfalfa, soybeans and other legumes (family Leguminoseae), cotton (family Malvaceae), and most vegetables as well as monocotyledonous plants. The useful plants produced by the method of this invention comprise tissues toxic to insects when ingested. Pests which may be controlled by means of the present invention and the crops that may be protected from them include, but are not limited to, those listed in Tables 1 and 2, respectively. Because of its susceptibility to a number of larvae, cotton is an ideal choice for the insertion of an insecticidal protein gene. Each of the following is a major cotton pest and is also susceptible to the *B. thuringiensis* insecticidal protein: *Heliothis zea* (cotton bollworm), *Pectionophora gossypiella* (pink bollworm), *Heliothis virescens* (tobacco budworm), *Trichoplusia ni*(cabbage looper). Application of insecticidal protein prepared from sporulating *B. thuringiensis* does not control insects such as the pink bollworm in the field because of their particular life cycles and feeding habits. A plant containing in its tissues insecticidal protein will control this recalcitrant type of insect, thus providing advantage over prior insecticidal uses of *B. thuringiensis*. By incorporation of the insecticidal protein into the tissues of a plant, the present invention additionally provides advantage over such prior uses by eliminating instances of nonuniform application and the costs of buying and applying insecticidal preparations to a field. Also, the present invention eliminates the need for careful timing of application of such preparations since small larvae are most sensitive to insecticidal protein and the protein is always present, minimizing crop damage that would otherwise result from preapplication larval foraging.

BRIEF DESCRIPTION OF THE FIGURES

FIG. 1 presents the sequence of the crystal protein gene of p123/58-10, described in Example 1.

DETAILED DESCRIPTION OF THE INVENTION

Figure 2:
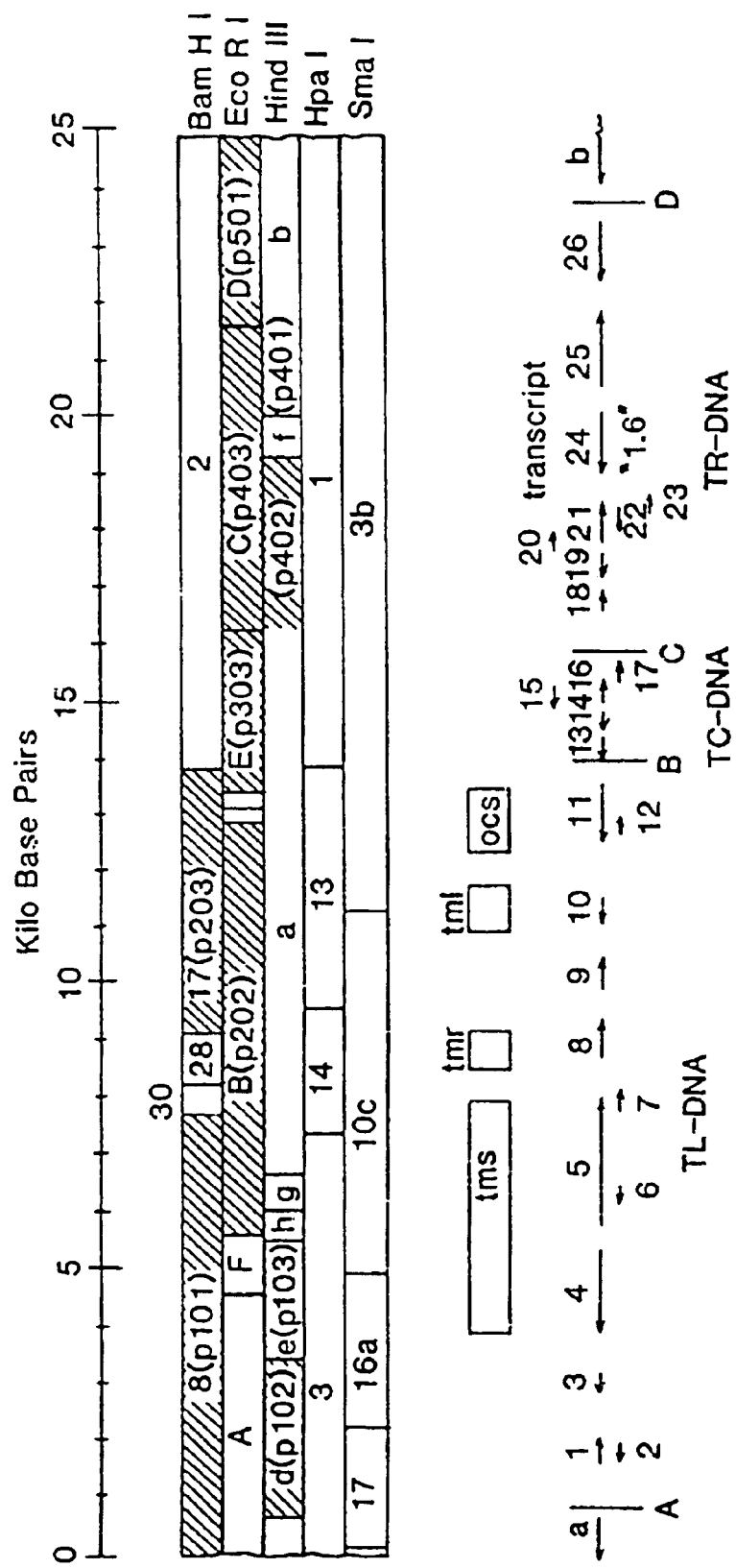
FIG. 2 presents a map of restriction sites and transcripts of the T-DNA of pTi15955.

The following definitions are provided, in order to remove ambiguities to the intent or scope of their usage in the specification and claims.

T-DNA: A segment of DNA derived from the transformation-inducing principle (TIP) which becomes integrated in the plant genome. As used herein, the term includes DNA originally derived from any tumor-inducing strain of Agrobacterium including *A. tumfaciens* and *A. rhizogenes*, the inserted segment of the latter sometimes referred to in the prior art as R-DNA. In addition, as used herein the term T-DNA includes any alterations, modifications, mutations, substitutions, insertions and deletions either naturally occurring or introduced by laboratory procedures, a principal structural requirement and limitation to such modifications being that sufficient of the right and left ends of naturally-occurring T-DNAs be present to insure the expected function of stable integration in the transformed plant cell genome which is characteristic of T-DNA. The T-DNA may itself be a composite of segments derived from a plurality of sources, naturally occurring or synthetic. In addition, the T-DNA must contain at least one plant expressible promoter, 5' or "upstream" from the site of insertion of the insecticide structural gene, in sufficiently complete form to control initiation of transcription and initiation of translation of an inserted insecticide structural gene. This promoter may be derived from a T-DNA gene, a plant gene, or any other gene having a promoter that is functional within a plant cell in at least one tissue and at least one developmental stage. Preferably, an insertion site will be provided "downstream" in the direction of transcription and translation initiated by the promoter (3' to the promoter), so located with respect to the promoter to enable an insecticide structural gene inserted therein to be expressed under control of the promoter, either directly or as a fusion protein. The T-DNA may also include a 3'-untranslated region downstream from the site of insertion of the insecticide structural gene, which may function to regulate termination of transcription, polyadenylation, and post-transcriptional RNA processing. Optionally, a fusion protein may also be formed between the insecticide structural gene and the 3' end of the structural gene donating the 3'-untranslated region. The promoter and 3'-untranslated region elements may be derived from the same, or different pre-existing genes and may be derived from the same or different plant, T-DNA, or other sources. For example, an insecticide structural gene, as exemplified herein, could be nested between a plant gene promoter and 3' sequence from the same gene, or it could be a construct comprising the 3'-untranslated region of one gene and the promoter of another, derived from the same or different plant species or T-DNA. The coding region of a plant gene, as herein defined, may include a cDNA copy of the structural portion of a plant gene. The promoter and 3'-untranslated regions may also include modifications, either naturally or artificially induced, and may include chemically synthesized segments.

Plant promoter: As used herein includes regulatory elements of a plant gene, and may further include structural elements, of a plant gene said elements being exogenous to the genes of T-DNA itself. These include, but are not limited to, promoters of the genes for phaseolin and the small subunit of ribulose-1,5-bisphosphate carboxylase. Furthermore, a plant gene promoter is a region of the gene which provides for and may regulate the initiation of transcription and the initiation of translation. Additionally, the plant structural gene sequences (the region which codes for a protein in part or in whole and which may or may not contain one or more introns) may be introduced into T-DNA. (An intron is a region of a gene transcript which is post-transcriptionally removed before the mRNA is translated.) Expression under control of a plant promoter may take the form of direct expression in which the structural gene normally controlled by the promoter is removed in part or in whole and replaced by the inserted insecticide structural gene, a start codon being provided either as a remnant of the plant structural gene or as part of the inserted insecticide structural gene, or by fusion protein expression in which part or all of the insecticide structural gene is inserted in correct reading frame phase within the existing plant structural gene. In the latter case, the expression product is referred to as a fusion protein. The promoter segment may itself be a composite of segments derived from a plurality of sources, naturally occurring or synthetic. Sources of a plant promoter include, but are not limited to, plants listed in Table 2.

T-DNA promoter: Refers to any of the naturally occurring promoters commonly associated with integrated T-DNA. These include, but are not limited to, promoters of the "1.6" transcript, octopine synthase gene (ocs), nopaline synthase gene (nos), tms, tml, and tmr genes, and may depend in part on the TIP source of the T-DNA. Expression under control of a T-DNA promoter may take the form of direct expression in which the structural gene normally controlled by the promoter is removed in part or in whole and replaced by the inserted insecticide structural gene, a start codon being provided either as a remnant of the T-DNA structural gene or as part of the inserted insecticide structural gene, or by fusion protein expression in which part or all of the plant structural gene is inserted in correct reading frame phase within the existing T-DNA structural gene. In the latter case, the expression product is referred to as a fusion protein. The promoter segment may itself be a composite of segments derived from a plurality of sources, naturally occurring or synthetic.

Plant expressible promoter: As used herein includes the definitions for T-DNA promoter and plant promoter, supra. However, an essential aspect of the promoter component of the present invention is that the insecticide structural gene be under control of a promoter expressible in a plant cell. Therefore, plant expressible promoter additionally refers to any promoter expressible in a plant cell which is expressed in at least one tissue during at least one developmental stage. Sources might include, but need not be limited to, plant viruses (e.g., the promoters for the 35S and 19S transcripts of cauliflower mosaic virus, CaMV), animal viruses, non-plant eukaryotes (e.g. animals, yeast), or plastids (e.g. a chloroplast or prokaryotic promoter if the insecticide gene is to be inserted into chloroplast DNA). Properties and components of a promoter that is derived from a source that is not a plant DNA or T-DNA (e.g., "TATA boxes," ATG translational start sites, intron splicing sites, etc.) are the same as described supra for T-DNA promoters and plant promoters are also included within the present definition. The promoter segment may itself be a composite of segments derived from a plurality of sources, naturally occur ring or synthetic.

Insecticide structural gene: As used herein includes that portion of an insecticide gene comprising a DNA segment coding for an insecticidal protein, polypeptide or portion thereof, possibly including a translational start codon, but lacking other functional elements of a bacterial gene that regulate initiation of transcription and initiation of translation, commonly referred to as the promoter region. (Note that in the present invention such bacterial functional elements may be present after transfer of the insecticide structural gene into T-DNA. However, because they are not functional within a plant cell, such elements are not referred to by the term "insecticide structural gene"). An insecticide structural gene may be derived in whole or in part from plasmid DNA, genomic DNA, cDNA and chemically synthesized DNA. It is further contemplated that an insecticide structural gene may contain one or more modifications in either the coding segments or untranslated regions which could affect the biological activity or chemical structure of the expression product, the rate of expression or the manner of expression control. Such modifications could include, but are not limited to, mutations, insertions, deletions, substitutions, and "silent" modifications that do not alter the chemical structure of the expression product but which affect intercellular localization, transport, excretion or stability of the expression product. The structural gene may constitute an uninterrupted coding sequence or it may include one or more introns, bounded by the appropriate plant functional splice junctions, which may be obtained from synthetic or a naturally occurring source. The structural gene may be a composite of segments derived from a plurality of sources, naturally occurring or synthetic, coding for a composite protein, the composite protein being insecticidal or being derived in part from an insecticidal protein.

Insecticidal protein: As used herein includes a bacterial protein toxic in any way to insects. This includes a protein or peptide that is directly or indirectly toxic or growth inhibitory under any circumstances to any insect. This also includes proteins that are toxic upon contact, ingestion, or respiration, where alone or in combination with other material, at any time within the life cycle of an insect, including egg, larva, pupa, nymph, and adult stages. This includes proteins toxic to insects, especially those of the families Lepidoptera and Diptera, and those of the genera Ostrinia, Heliothis, Pectinophora, and Trichoplusia, e.g., *M. sexta, O. nubilalis, H. zea, H. virescens, P. gossypiella*, and *T. ni*. Other taxa that might be chosen as targets include, but are not limited to, those listed in Table 1. Examples of insecticidal proteins include, but are not limited to various varieties, listed in Table 3, of *Bacillus thuringiensis*, or in other species of Bacillus, e.g., *B. cereus, B. popilliae*, and *B. sphericus*. Genes that are used to construct or otherwise encode sequences encoding proteins toxic to insects include, but are not limited to, phospholipases, hyaluronidases, phosphatases, proteases, and the various crystal proteins of *B. thuringiensis*. The term crystal protein should be understood to refer to both the full-length protoxin and toxin forms, to toxic proteins related to the protein which is found in the crystalline inclusion bodies of *Bacillus thuringiensis*, and to artificial modifications of naturally occurring crystal proteins. Related proteins might be identified by nucleic acid or protein structural or sequence homology, immunological cross-reactivity, or cross-hybridization of nucleic acids.

Plant tissue: Includes differentiated and undifferentiated tissues of plants including, but not limited to roots, shoots, pollen, seeds, tumor tissue, such as crown galls, and various forms of aggregations of plant cells in culture, such as embryos and calluses. The plant tissue may be in Planta or in organ, tissue, or cell culture, and may be derived from plants which include, but are not limited to, those listed in Table 2.

Plant cell: As used herein includes plant cells in planta and plant cells and protoplasts in culture, and may be derived from plants which include, but are not limited to those listed in Table 2.

Production of a genetically modified plant expressing an insecticide structural gene introduced via T-DNA combines the specific teachings of the present disclosure with a variety of techniques and expedients known in the art. In most instances, alternative expedients exist for each stage of the overall process. The choice of expedients depends on variables such as the choice of the basic TIP or other vector systems for the introduction and stable maintenance of the expressible insecticide structural gene, the plant species to be modified and the desired regeneration strategy, and the particular insecticide structural gene to be used, all of which present alternative process steps which those of ordinary skill are able to select and use to achieve a desired result. For instance, although the starting point for obtaining an insecticide structural gene is exemplified in the present application by DNA isolated from *B. thuringiensis* var. *kurstaki* HD-73, DNA of other insecticidal protein gene-carrying bacterial strains or recombinant DNA molecules might be substituted as long as appropriate modifications are made to the gene isolation and manipulation procedures. As novel means are developed for the controlled expression and/or stable insertion of foreign genes in plant cells, those of ordinary skill in the art will be able to select among those alternate process steps to achieve a desired result. The fundamental aspects of the invention are the nature and structure of the insecticide structural gene and its means of insertion and expression in a plant genome. The remaining steps of the preferred embodiment for obtaining a genetically modified plant include inserting the promoter/insecticide structural gene combination into T-DNA, transferring the modified T-DNA to a plant cell wherein the modified T-DNA becomes stably integrated as part of the plant cell genome, techniques for in vitro culture and eventual regeneration into whole plants, which may include steps for selecting and detecting transformed plant cells and steps of transferring the introduced gene from the originally transformed strain into commercially acceptable cultivars.

A principal feature of the present invention in its preferred embodiment is the construction of T-DNA having an inserted insecticide structural gene under control of a plant-expressible promoter, or, most preferably, a T-DNA promoter, as these terms have been defined, supra. The insecticide structural gene must be inserted in correct position and orientation with respect to the desired promoter. Position has two aspects. The first relates to the side of the promoter on which the structural gene is inserted. It is known that the majority of promoters control initiation of transcription and translation in one direction only along the DNA. The region of DNA lying under promoter control is said to lie "downstream" or alternatively "behind" or "3' to" the promoter. Therefore, to be controlled by the promoter, the correct position of plant structural gene insertion must be "downstream" from the promoter. (It is recognized that a few known promoters exert bi-directional control, in which case either side of the promoter could be considered to be "down stream" therefrom.) The second aspect of position refers to the distance, in base pairs, between known functional elements of the promoter, for example the transcription initiation site, and the translational start site of the structural gene. Substantial variation appears to exist with regard to this distance, from promoter to promoter. Therefore, the structural requirements in this regard are best described in functional terms. As a first approximation, reasonable operability can be obtained when the distance between the promoter and the inserted insecticide structural gene is similar to the distance between the promoter and the T-DNA gene it normally controls. Orientation refers to the directionality of the structural gene. That portion of a structural gene which ultimately codes for the amino terminus of the plant protein is termed the 5'-end of the structural gene, while that end which codes for amino acids near the carboxyl end of the protein is termed the 3'-end of the structural gene. Correct orientation of the insecticide structural gene is with the 5'-end thereof proximal to the promoter. An additional requirement in the case of constructions leading to fusion protein expression is that the insertion of the insecticide structural gene into the promoter-donated structural gene sequence must be such that the coding sequences of the two genes are in the same reading frame phase, a structural requirement which is well understood in the art. An exception to this requirement, of relevance to the present invention, exists in the case where an intron separates coding sequences derived from an insecticidal protein gene from the first coding segment of the insecticide structural gene. In that case, the insecticide structural gene must be provided with a splice site compatible with the upstream splice junction contributed by the noninsecticidal coding sequences, and the intron splice sites must be so positioned that the correct reading frame for the promoter-donated structural gene and the insecticide structural gene are restored in phase after the intron is removed by post-transcriptional processing. Differences in rates of expression or developmental control may be observed when a given insecticide structural gene is inserted under control of different plant expressible promoters. Different properties including, but not limited to such properties as stability, intercellular or intracellular localization or excretion, solubility, target specificity, and other functional properties of the expressed protein itself may be observed in the case of fusion proteins depending upon the insertion site, the length and properties of the segment of T-DNA protein included within the fusion protein and mutual interactions between the components of the fusion protein that effect folded configuration thereof, all of which present numerous opportunities to manipulate and control the functional properties of the insecticidal protein product, depending upon the desired physiological proper ties within the plant cell, plant tissue, and whole plant.

Location of the promoter/insecticide structural gene combination insertion site is not critical as long as the transfer function sequences immediately surrounding the T-DNA borders are not disrupted, since these regions appear from prior art studies to be essential for insertion of the modified T-DNA into the plant genome. Preferred insertion sites are those which lie in areas that are most actively transcribed, in particular the tml gene and an area designated "1.6" lying in the HindIII-f fragment, and equivalent to transcript 24, as shown in FIG. 2. The term "1.6" is used herein to designate this actively transcribed region of T-DNA. The T-DNA into which the promoter/insecticide gene combination is inserted, is obtained from any of the TIP plasmids. The insecticide gene is inserted by standard techniques well-known to those skilled in the art. The orientation of the inserted plant gene, with respect to the direction of transcription and translation of endogenous T-DNA genes is not critical, either of the two possible orientations is functional. Differences in rates of expression may be observed when a given gene is inserted at different locations within T-DNA, possibly because of such factors as DNA methylation chromatin structure. Readily detectable levels of expression of a plant promoter from the phaseolin gene have been obtained where that gene was inserted into pTi15955, an octopine-type plasmid of A. tumfaciens at a SmaI site found within the tml gene or a HpaI site found within tmr.

A convenient means for inserting a promoter/insecticide structural gene combination into T-DNA involves the use of a shuttle vector, as described supra, having segments of T-DNA (those segments between which insertion is desired) incorporated into a plasmid capable of replicating in E. coli. The T-DNA segment contains a restriction site, preferably one which is unique within the shuttle vector. The insecticide structural gene can be inserted at the unique site in the T-DNA sequences and the shuttle vector is transferred into cells of the appropriate Agrobacterium strain, preferably one whose T-DNA is homologous with the T-DNA segments of the shuttle vector. The transformed Agrobacterium strain is preferably grown under conditions which permit selection of a double-homologous recombination event which results in replacement of a pre-existing segment of the Ti plasmid with a segment of T-DNA of the shuttle vector. However, it should be noted that the present invention is not limited to the introduction of the promoter/insecticide structural gene combination into T-DNA by a double homologous recombination mechanism; a homologous recombination event with a shuttle vector (perhaps having only a single continuous region of homology with the T-DNA) at a single site or an insertion of a promoter/gene-carrying bacterial transposon will also prove an effective means for inserting that combination into T-DNA.

Following the strategy just described, the modified T-DNA can be transferred to plant cells by any technique known in the art. For example, this transfer is most conveniently accomplished either by direct infection of plants with the novel strain containing an insecticide gene incorporated within T-DNA, or by cocultivation of the Agrobacterium strain with plant cells. The former technique, direct infection, results in due course in the appearance of a tumor mass or crown gall at the site of infection. Crown gall cells can be subsequently grown in culture and, under appropriate circumstances known to those of ordinary skill in the art, regenerated into whole plants that contain the inserted T-DNA segment. Using the method of cocultivation, a certain proportion of the plant cells are transformed, that is to say have T-DNA transferred therein and inserted in the plant cell genome. In either case, the transformed cells must be selected or screened to distinguish them from untransformed cells. Selection is most readily accomplished by providing a selectable marker incorporated into the T-DNA in addition to the insecticide structural gene. Examples include either dihydrofolate reductase or neomycin phosphotransferase expressed under control of a nopaline synthase promoter. These markers are selected by growth in medium containing methotrexate or kanamycin, respectively, or their analogs. In addition, the T-DNA provides endogenous markers such as the gene or genes controlling hormone-independent growth of Ti-induced tumors in culture, the gene or genes controlling abnormal morphology of Ri-induced tumor roots, and genes that control resistance to toxic compounds such as amino acid analogs, such resistance being provided by an opine synthase. Screening methods well-known to those skilled in the art include assays for opine production, specific hybridization to characteristic RNA or T-DNA sequences, or immunological assays for specific proteins, including ELISAs (acronym for "enzyme linked immunosorbant assay"), radioimmune assays and "western" blots. Additionally the toxic properties of expressed insecticidal protein can be used to identify transformed tissue.

An alternative to the shuttle vector strategy involves the use of plasmids comprising T-DNA or modified T-DNA, into which an insecticide structural gene is inserted, said plasmids being capable of independent replication in an Agrobacterium strain. Recent evidence reviewed in the Background indicates that the T-DNA of such plasmids can be transferred from an Agrobacterium strain to a plant cell provided the Agrobacterium strain contains certain transacting genes whose function is to promote the transfer of T-DNA to a plant cell. Plasmids that contain T-DNA and are able to replicate independently in an Agrobacterium strain are herein termed "sub-TIP" plasmids. A spectrum of variations is possible in which the sub-TIP plasmids differ in the amount of T-DNA they contain. One end of the spectrum retains all of the T-DNA from the TIP plasmid, and is sometimes termed a "mini-TIP" plasmid. At the other end of the spectrum, all but the minimum amount of DNA surrounding the T-DNA border is deleted, the remaining portions being the minimum necessary to be transferable and integratable in the host cell. Such plasmids are termed "micro-TIP." Sub-TIP plasmids are advantageous in that they are small and relatively easy to manipulate directly, eliminating the need to transfer the gene to T-DNA from a shuttle vector by homologous recombination. After the desired structural gene has been inserted, they can easily be introduced directly into a plant cell containing the transacting genes that promote T-DNA transfer. Introduction into an Agrobacterium strain is conveniently accomplished either by transformation of the Agrobacterium strain or by conjugal transfer from a donor bacterial cell, the techniques for which are well-known to those of ordinary skill. For purposes of introduction of novel DNA sequences into a plant genome, TIP plasmids and sub-TIP plasmids should be considered functionally equivalent.

Although the preferred embodiment of this invention incorporates a T-DNA-based Agrobacterium-mediated system for incorporation of the insecticide gene into the genome of the plant which is to be made insect resistant, other means for transferring and incorporating the gene are also included within the scope of this invention. Other means for the stable incorporation of the insecticide gene into a plant genome additionally include, but are not limited to, use of vectors based upon viral genomes, minichromosomes, transposons, and homologous or nonhomologous recombination into plant chromosomes. Alternate forms of delivery of these vectors into a plant cell additionally include, but are not limited to, direct uptake of nucleic acid, fusion with vector-containing liposomes, microinjection, and encapsidation in viral coat protein followed by an infection-like process. Systems based on Agrobacterium cells and TIPs can be used to transform dicots and gymnosperms by transfer of DNA from a bacterium to a plant cell; systems based on alternate vectors or means for vector delivery may be used to transform all gymnosperms and all angiosperms, including both monocots and dicots.

Regeneration of transformed cells and tissues is accomplished by resort to known techniques. An object of the regeneration step is to obtain a whole plant that grows and reproduces normally but which retains integrated T-DNA. The techniques of regeneration vary somewhat according to principles known in the art, depending upon the origin of the T-DNA, the nature of any modifications thereto and the species of the transformed plant. Plant cells transformed by an Ri-type T-DNA are readily regenerated, using techniques well-known to those of ordinary skill, without undue experimentation. Plant cells transformed by Ti-type T-DNA can be regenerated, in some instances, by the proper manipulation of hormone levels in culture. Preferably, however, the Ti-transformed tissue is most easily regenerated if the T-DNA has been mutated in one or both of the tmr and tms genes. Inactivation of these genes returns the hormone balance in the transformed tissue toward normal and greatly expands the ease and manipulation of the tissue's hormone levels in culture, leading to a plant that is readily regenerated because of its more normal hormone physiology. It is important to note that if the mutations in tmr and tms are introduced into T-DNA by double homologous recombination with a shuttle vector, the incorporation of the mutations must be selected in a different manner than the incorporation of the promoter/insecticide structural gene. For example, in the former instance one might select for chloramphenicol resistance while the latter selection might be for resistance to kanamycin. The inactivation of the tms and tmr loci may be accomplished by an insertion, deletion, or substitution of one or more nucleotides within the coding regions or promoters of these genes, the mutation being designed to inactivate the promoter or disrupt the structure of the protein. (The construction of suitable mutations has been exemplified by Hall, T. C. et al., U.S. patent application Ser. Nos. 485,613 and 485,614.) In some instances, tumor cells are able to regenerate shoots which carry integrated T-DNA and express T-DNA genes, such as nopaline synthase, and which also express an inserted insecticide structural gene. The shoots can be maintained vegetatively by grafting to rooted plants and can develop fertile flowers. The shoots thus serve as parental plant material for normal progeny plants carrying T-DNA and expressing the insecticide structural gene inserted therein.

The genotype of the plant tissue transformed is often chosen for the ease with which its cells can be grown and regenerated in in vitro culture. Should a cultivar of agronomic interest be unsuitable for these manipulations, a more amenable variety is first transformed. After regeneration, the newly introduced foreign insecticidal protein gene is readily transferred to the desired agronomic cultivar by techniques well-known to those skilled in the arts of plant breeding and plant genetics. Sexual crosses of transformed plants with the agronomic cultivars yielded initial hybrids. These hybrids can then be backcrossed with plants of the desired genetic background. Progeny are continuously screened and selected for the continued presence of integrated T-DNA or for the new phenotype resulting from expression of the inserted insecticidal protein gene. In this manner, after a number of rounds of backcrossing and selection, plants can be produced having a genotype essentially identical to the agronomically desired parents with the addition of the inserted insecticidal protein gene.

In an alternative method for conferring insect resistance to a crop, one may infect plants within a field which is to be protected with an Agrobacterium cell harboring a TIP plasmid having undisabled T-DNA which carries an expressible insecticidal protein gene. We have found that larvae will feed on crown gall tissue. When insect larvae infesting the field eat transformed tissue containing an insecticide gene, they will be affected by the insecticidal protein within that tissue. The Agrobacterium and TIP might additionally encode genes for insect attractants. The presence of such attractants in transformed tissue will increase the insects' preference for such tissue as a food source relative to the rest of the crop material in the field.

EXAMPLES

The following Examples utilize many techniques well known and accessible to those skilled in the arts of molecular biology and manipulation of TIPs and Agrobacterium; such methods are fully described in one or more of the cited references if not described in detail herein. Enzymes are obtained from commercial sources and are used according to the vendor's recommendations or other variations known to the art. Reagents, buffers and culture conditions are also known to those in the art. Reference works containing such standard techniques include the following: Wu, R. (ed.) (1979) Methods Enzymol. 68; Wu, R. et al. (eds.) (1983) Methods Enzymol. 100 and 101; Grossman, L. and Moldave. K. (eds.) (1980) Methods Enzymol. 65,; Miller, J. H. (1972) *Experiments in Molecular Genetics*; Davis, R. et al. (1980) *Advanced Bacterial Genetics*; Schleif, R. F. and Wensink, P. C. (1982) *Practical Methods in Molecular Biology*; and Maniatis, T. et al. (1982) *Molecular Cloning*. Additionally, Lathe, R. F. et al. (1983) Genet. Eng. 4:1–56, make useful comments on DNA manipulations.

Textual use of the name of a restriction endonuclease in isolation, e.g., "BclI", refers to use of that enzyme in an enzymatic digestion, except in a diagram where it can refer to the site of a sequence susceptible to action of that enzyme, e.g., a restriction site. In the text, restriction sites are indicated by the additional use of the word "site," e.g., "BclI site." The additional use of the word "fragment," e.g., "BclI fragment," indicates a linear double-stranded DNA molecule having ends generated by action of the named enzyme (e.g., a restriction fragment). A phrase such as "BclI/SmaI fragment" indicates that the restriction fragment was generated by the action of two different enzymes, here BclI and SmaI, the two ends resulting from the action of different enzymes. Note that the ends will have the characteristics of being "blunt" or "sticky" (i.e. having a single-stranded protuberance capable of base-pairing with a complementary single-stranded oligonucleotide) and that the sequence of a sticky-end will be determined by the specificity of the enzyme which produces it.

In these Examples, special symbols are used to make sequences more easily understood. Sequences that code for proteins are underlined, and codons are separated with slashes (/). The positions of cuts or gaps in each strand caused by restriction endonucleases or otherwise are indicated by the placement of asterisks (*).

Plasmids, and only plasmids, are prefaced with a "p," e.g., pTi15955 or pKS-4, and strain parenthetically indicate a plasmid harbored within, e.g., *A. tumefaciens* (pTi15955) or K802(pKS-4). Table 4 provides an index useful for identifying plasmids and their interrelationships. Table 5 provides a list of deposited strains.

Example 1

The first step in developing an insect resistant crop was to clone the insecticidal protein gene of *B. thuringiensis* var. *kurstaki* HD-73, which is on deposit with the Agricultural Research Culture Collection, Northern Regional Research Laboratory, Peoria, Ill, and has NRRL number B-4488.

1.1 Cloning the *Bacillus thuringiensis* Insecticidal Protein Gene

The 50 megadalton (MD) plasmid was enriched from HD-73 using sucrose gradient centrifugation. An HD-73 library was constructed by first digesting this plasmid with HindIII. The resulting fragments were mixed with and ligated to HindIII-linearized pBR322 (Bolivar, F. et al. (1978) Gene 2:95–113) and transformed into *E. coli* HB101. Ampicillin-resistant tetracycline-sensitive transformants were screened by digesting isolated plasmid DNA with HindIII and choosing those clones with 6.6 kilobase pair (kbp) inserts. Colonies containing plasmids p123/58-3 and p123/58-10 were selected from the HD-73 library for further analysis using an insect bioassay (see Example 8). These clones were grown in L-broth and a 250 fold concentrated cell suspension was sonicated and the extract applied to the surface of insect diet. Neonatal *Manduca sexta* (tobacco hornworm) larvae were placed on the diet for one week. Insect larvae fed extracts of strains harboring p123/58-3 or p123/58-10 did not grow and all larvae died in 2 to 5 days. There was no apparent difference between the larvae fed these extracts and those fed insecticidal protein purified from cells of *B. thuringiensis*.

Restriction enzyme analysis of p123/58-3 and p123/58-10 showed that the two plasmids were identical except for having the 6.6 kbp *B. thuringiensis* DNA fragment inserted into the pBR322 vector in opposite orientations. Note that either of these two plasmids can be converted to the other by digestion with HindIII, religation, and transformation into HB101 followed by appropriate selection and screening steps.

p123/58-10 was used to further probe the transformants from the HD-73 plasmid library. Sixteen of the 572 colonies hybridized to the insert of clone p123/58-10 and all had the characteristic 6.6 kbp HindIII fragment. Further restriction enzyme analysis showed these clones to all be one of the two possible orientations in pBR322 of the same DNA fragment.

This suggested there could be a single crystal protein gene in strain HD-73. That these clones represent the only insecticidal protein gene in HD-73 was confirmed by hybridizing labeled p123/58-10 probe to Southern blots of HD-73 plasmid DNA digested with HindIII, BglII or SalI. None of these enzymes has a restriction site in our cloned crystal protein gene. Hybridization results showed a single band of *B. thuringiensis* cellular DNA hybridized with p123/58-10 and further indicated that HD-73 has a single insecticidal crystal protein gene. We have identified a number of other clones by hybridization with a probe made from p123/58-10. Restriction mapping has shown that these clones are all identical to either p123/58-3 or p123/58-10, further supporting the conclusion that the HD-73 has a single crystal protein gene.

1.2 Immunological Analysis

Analyses on the protein produced in the *E. coli* clones shows that p123/58-3 and p123/58-10 encoded protein that formed a precipitin band with antiserum to *B. thuringiensis* insecticidal protein in Ouchterlony diffusion slides. Cell extracts were analyzed on 10% SDS-poly-acrylamide gels, transferred to nitrocellulose, and immunological reactions were done with antibody and 125I-protein A (Western blots, Example 7). No band was found at 130 kD (kilodalton) where denatured protoxin is observed, however, a peptide of about 67 kD was seen that binds crystal protein antibody (Western blots done as in Example 7), and was identical in size to activated toxin. This peptide accounted for approximately 0.1% of the total *E. coli* protein.

1.3 Sequence Analysis

We compared our DNA sequence results (FIG. 1), obtained by methods well-known to those skilled in the art of DNA sequencing (e.g. see Maxam, A. M. and Gilbert, W. (1980) Methods Enzymol. 65:499–560), with published sequences (see Background). The published sequences showed only partial homology with our own sequence. An open reading frame of about 2.8 kbp was observed which was bounded at the 5'-end by a translational start signal (ATG) and did not stop before encountering the HindIII site at the junction between the *B. thuringiensis* DNA and the pBR322 vector. The size of the protein encoded by this open reading frame from the ATG to the HindIII site is greater than that of the 67 kD protein that we observed to be translated in *E. coli* cells but less than what is needed to encode the 130 kD native crystal protein. That the exact means of translational termination in the pBR322 encoded read-through peptide was not important was suggested by the finding that insecticidal activity was encoded by *B. thuringiensis* DNA inserts having either orientation within the pBR322 vector. Presumably the initially translated amino acid residues carboxy-terminal to the ultimate carboxy-terminus of the translated polypeptide were removed in *E. coli* by a proteolytic process similar to that which naturally activates the crystal protein.

Example 2

This example teaches the insertion of the Bacillus thuringiensis insecticide gene between a T-DNA gene promoter and a polyadenylation (poly(A) addition) signal, the transfer of the insecticide gene to various plant species via a Ti plasmid, and the regeneration of plants expressing this gene under control of the T-DNA promoter. A large part of the strategy used in this construction is diagrammed in FIG. 3, which represents plasmids schematically and is not necessarily drawn to scale.

2.1 Introduction of BamHI Site into the Insecticidal Protein Gene

A BamHI site is introduced into the insecticidal protein gene of p123/58-10 at a location just 5' to the start of the coding sequence. The wild type base sequence (b) and the changed bases in an oligonucleotide primer (a) are as follows:

```
                    BamHI
a)    5'AGATGGAG*GATCCTT ATG GAT AAC AAT 3'
b)    ...AGATGGAGGTAACTT/ATG/GAT/AAC/...
                            Met Asp Asn Asn
```

The changed bases are the underlined ATC sequence in (a). Note that good hybridization properties are insured because only three out of 27 base pairs are changed. p123/58-10 is digested with HindIII and is mixed with and ligated to HindIII-linearized mWB2344 RF (replicative form) DNA. The mixture is transformed into JM103 and transformed colonies are screened by plasmid isolation followed by restriction analysis for the presence of insertion of a single copy of the insecticidal protein gene-bearing fragment. Vectors containing the two possible orientations are labeled M13-Bt-A and M13-Bt-S. They have the antisense and sense strands, respectively, of the insecticide structural gene when in viral form. M13-Bt-A is hybridized with the oligonucleotide primer, 5'AGATGGAGGATCCTTATGGAT AACAAT3', previously synthesized as described in Example 10.1. The oligonucleotide: M13-Bt-A hybrid is incubated with the Klenow fragment of *E. coli* DNA polymerase I, covalently closed circular DNA (cccDNA) is enriched, and the mixture is transformed into JM103. The virions produced by transformants are isolated and used to infect cells at a low multiplicity of infection. RF DNA is isolated from a number of the infected colonies and is characterized by restriction mapping. Clones derived from the mutant oligonucleotide-primed strand are identified by the presence of a novel BamHI site at the 5'-end of the insecticide structural gene, and one such vector is designated M13-Bt-A(Bam).

M13-Bt-A(Bam) RF DNA is digested with BamHI and HindIII, and is mixed with and ligated to a linker, synthesized as described in Example 10.1, having the following structure:

```
       HindIII            BamHI
    5'AGCTAGCTGACTAG3'
       3'TCGACTGATCCTAG5'
```

Note that this linker contains translational stop signals (underlined) in all three possible reading-phases. The linkers are trimmed by digestion with BamHI and an insecticide structural gene-bearing DNA fragment is purified by agarose gel electrophoresis.

2.2 Construction and Modification of a Promoter Vehicle

The T-DNA "1.6" gene is summarized as follows:

```
              ClaI            960 bp  250 bp  ClaI  60 bp   50 bp
5'...TACACCAAAT*CG/ATG/GAC/ATG/.../TGA/....AT*CGAT....AAATAA...AAATAA...3'
   promoter         Met Asp Met ....stop         polyadenylation signals
```

By removing the ClaI fragment, the promoter region of the "1.6" gene can be brought next to the 3'-downstream region of the gene. This 3' region includes polyadenylation signals. The resulting structure is summarized as follows:

```
              ClaI               60 bp                50 bp
5'...ATACACCAAAT*CGATAGT.......AAATAA........AAATAAAA...3'
    promoter              polyadenylation signals
``` pKS111, which is a pRK290 clone corresponding to the T-DNA clone p403 (which encodes the "1.6" gene which was described in the Detailed Description, transcript 24 in FIG. 2, see also Fink, C. F. (1982) M.S. thesis, University of Wisconsin-Madison), is digested with ClaI and then religated. The ligation mix is transformed into *E. coli* K802 (Wood, W. B. (1966) J. Mol. Biol. 16:118) and selected for tetracycline resistance. Plasmids are isolated by doing. "minipreps" (Plasmid preparations from small volume cell cultures) and restriction maps are obtained to prove the structure. The new vehicle, pKS-proI (see Hall, T. C. et al., U.S. application Ser. No. 485,614), can be linearized by ClaI.

pKS-proI grown in K802 was cut with ClaI. After converting sticky-ends to blunt-end with the Klenow fragment of *E. coli* DNA polymerase I, the DNA was mixed with and ligated to a BamHI linker. The resulting mixture was digested with ClaI to remove religated pKS-proI, and transformed into K802. Plasmids from tetracycline resistant transformants are screened by restriction analysis and a plasmid having the ClaI site at the ATG translational start replaced with a BamHI site is designated pKS-proI(Bam).

2.3 Introduction of a Kanamycin Resistance Gene into pKS-proI(Bam)

It is advantageous to have a kanamycin resistance (kan) gene inserted next to the promoter/insecticide gene combination so as to allow selection of double homologous recombinants after a triparental mating. The source of kan was pKS-4 (Example 2.5). In pKS-4 the kan gene is flanked on one side by a ClaI site. In order to remove a kan gene bearing fragment from pKS-4 with ClaI (i.e. on a ClaI/kan" fragment) it is necessary to introduce a ClaI site into that plasmid on the opposite side of kan from the existing ClaI site. This is accomplished by converting a conveniently positioned BamHI site (5' . . . G*GATCC . . . 3') to the specificity of ClaI (5' . . . AT*CGAT . . . 3').

pKS-4 is linearized by digestion with BamHI, thereby generating sticky-ends having the following structures:

```
         5'...G              GATCC...3'
         3'...CCTAG               C...5
```

The recessed ends of this structure is filled in by incubation with the Klenow fragment of *E. coli* DNA polymerase I, forming the following blunt-ends:

```
         ...GGATC          GATCC...
         ...CCTAG          CTAGG...
```

When these ends were blunt end ligated together, the resulting suture has the following sequence:

```
                   ClaI
             ...GGAT*CG ATCC...
             ...CCTA GC*TAGG...
```

Note that the resulting structure is susceptible to the action of ClaI but not to that of BamHI.

Alternatively to the above construction, one may convert the BamHI site, or another conveniently located restriction site, into a ClaI site by use of the appropriate linkers. pKS-4 was digested with SmaI mixed with and ligated to ClaI/blunt-ended linkers having the sequence 5' CATCGATG3', digested with ClaI religated, and transformed into K802. Plasmids isolated from transformants resistant to kanamycin were screened for presence of a novel ClaI site in the position formally occupied by a SmaI site. A ClaI/kan fragment can be isolated from such a plasmid. The plasmid is designated pkS4.2.

Figure 3:
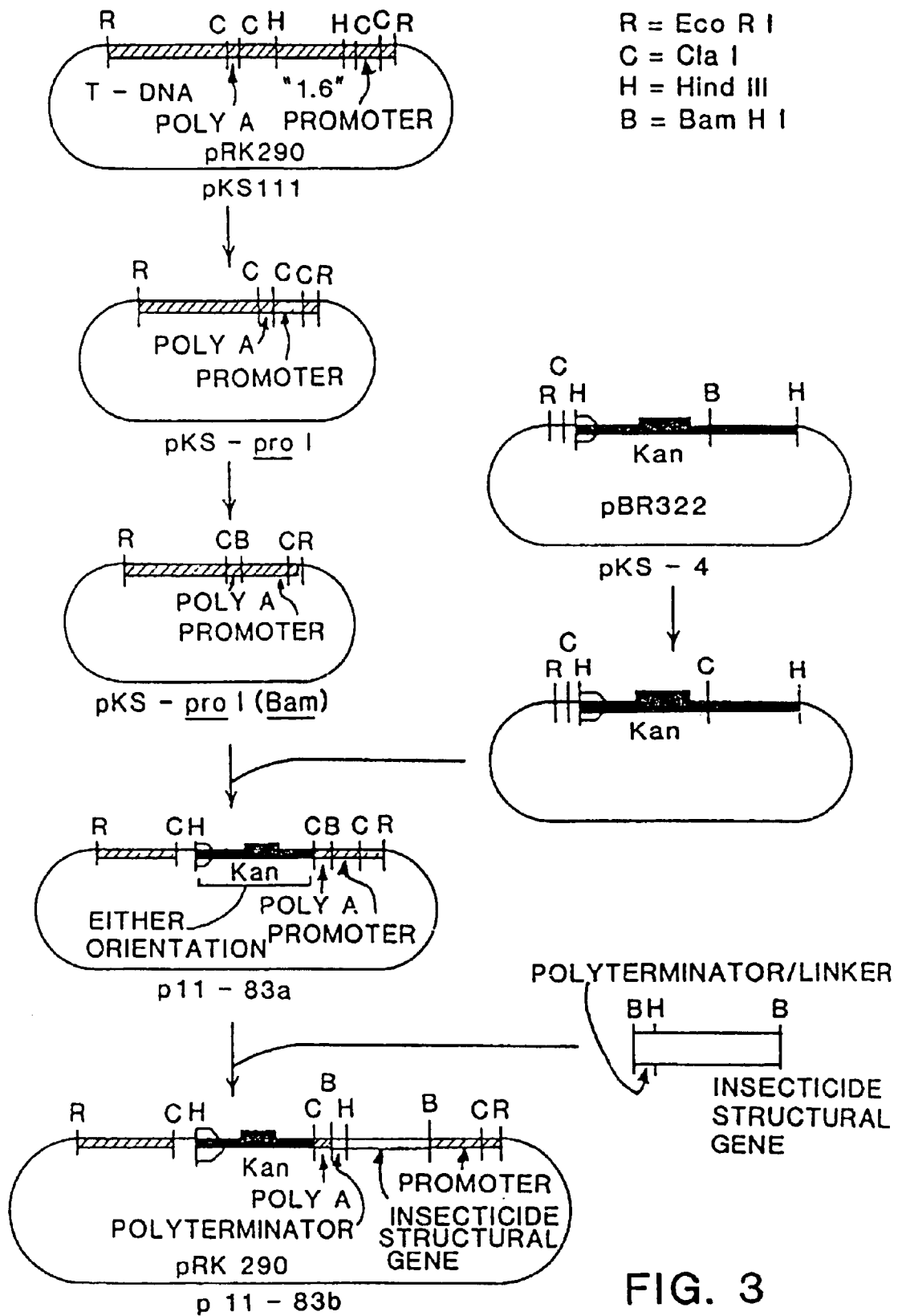
FIG. 3 is a diagram of a construction described in Example 2 of a recombinant DNA vector carrying an insecticide structural gene under control of a plant expressible promoter.

When grown in *E. coli* K802, pKS-proI(Bam) is methylated at two remaining ClaI sites: one is about 145 bases from the promoter-polyadenylation junction (this is about 30 bases past the second polyadenylation site), the other is about 200 bases from the right hand p403 EcoRI site (see FIG. 2). Methylation blocks cutting by the ClaI restriction endonuclease at an otherwise susceptible site. Therefore, these methylations protect these sites and effectively direct action of the ClaI enzyme to other sites. pKS-proI(Bam) is transferred to and grown in *E. coli* GM33, a strain that does not methylate adenosine residues in DNA, so that the otherwise methylated ClaI sites can be cut. After purification of that plasmid from GM33 (pKS-proI(Bam)), a partial digestion is done with ClaI and the resulting mixture is ligated-with the ClaI/kan fragment described above. After transformation into *E. coli* K802, transformants are selected on tetracycline and kanamycin containing media. After plasmid isolation and restriction mapping, a clone having the desired construction is identified and the plasmid found in this clone is labeled p11-83a (FIG. 3).

p11-83a has a kan gene-bearing fragment ligated into the "middle" ClaI site about 30 bp past the second polyadenylation site. The BamHI fragment of the insecticide gene, isolated from the modified vector constructed in Example 2.1, is now ligated into the BamHI site of BamHI-linearized p11-83a that has been transferred to and grown in K802 and is methylated. After transformation into K802, tetracycline and kanamycin selection, plasmid isolation, and restriction enzyme mapping, the desired construction having the insecticide structural gene inserted between the pTi15955 "1.6" promoter and polyadenylation site is identified, and the plasmid harbored therein is labeled p11-83b (FIG. 3).

2.4 Introduction of p11-83b into Ti Plasmids p11-83b is introduced into pTi15955, pTiA66 (equivalent to pTi15955 but having a nonfunctional tms gene), and mutants deleted in gene affecting regeneration by homologous recombination (Example 10). Tobacco plants are transformed by a system described in Example 6, and transformants are identified by Southern and Northern blots (techniques well-known to those skilled in the art) with appropriate probes and by the presence of octopine and crystal protein. Transformed tobacco tissue is lethal to tobacco hornworms. Tobacco plants are regenerated from transformed cells as described in Example 6, and entered into breeding programs. Fields of regenerated plants and their insecticidal protein-containing descendants are resistant to infestation by larvae of insects such as tobacco hornworm by virtue of the toxic effect such larvae experience when eating tissue from such plants.

2.5 Cloning and Isolation of a Kanamycin Resistance Gene pRZ102 (Jorgenson, R. A. et al. (1979) Mol. Gen. Genet. 177:65–72), a ColE1 plasmid carrying a copy of the transposon Tn5, was digested with BamHI and HindIII, mixed with pBR322 previously linearized with the same two enzymes, ligated, and transformed into K802. Plasmids, isolated from transformants selected for resistance to both ampicillin and kanamycin were restriction mapped and one having the structure shown in FIG. 3 was labeled pKS-4. pkS-4 DNA may be isolated from *E. coli* C600 (pKS-4) which has been deposited as NRRL B-15394.

Example 3

This example teaches another method of inserting an expressible gene for the *B. thuringiensis* insecticidal protein into a plant genome. The shuttle vector is similar to that used by Fink, C. L. (1982) M.S. thesis, University of Wisconsin-Madison, to put the nos gene into an octopine Ti plasmid. In the present invention, the protein coding sequences for nos are removed and replaced with an insecticidal gene before insertion into the Ti plasmid. The eventual result is an octopine-type Ti plasmid carrying an insecticide gene expressible in plant cells under control of a nopaline synthase promoter.

3.1 Moving the Nos Gene into M13mp7 pCF44 DNA (Fink, supra) was digested with XhaI, religated to itself, and transformed back into K802. Plasmid DNA isolated from ampicillin-resistant transformants was analyzed with restriction enzymes. A plasmid having a single XhoI site within its Ti plasmid-derived DNA sequences was designated pCF44A. The single XhoI site was the result of the deletion of a DNA fragment between the two pCF44 XhoI sites. Deletion of this XhoI fragment resulted in the complete removal of two inconvenient ClaI sites.

pCF44A DNA was digested with HindIII and BamHI, mixed with and ligated to pBR322 which had been digested with the same two restriction enzymes and transformed into K802. Ampicillin resistant transformants were selected and screened by restriction enzyme analysis of plasmid DNA and a colony was identified which contained a nos gene-containing plasmid, labeled pNS5.

pNS5 DNA, having been isolated from a nonmethylating host, was digested with BclI and BamHI and was mixed with and ligated to a double-stranded circular replicative form (RF) of the single-stranded DNA vector M13mp7 which had been linearized with BamHI. After transformation of the mixture into JM103 and selection of white plaques, two colonies were identified by restriction mapping after RF isolation, designated M13-1 and M13-3, contained the sense and antisense strands, respectively, when in single-stranded form.

3.2 Placement of an NcoI Site Behind the Nos Promoter

An oligonucleotide primer having the sequence 5'AGTCTCATACTCACTCTCAATCCAAATAATCTGCCATGGAT3' was synthesized as described in Example 10.1. This oligonucleotide was changed at the underlined base from the naturally occurring sequence at the 5'-end of the nos structural gene. The change resulted in the introduction of an NcoI site, 5' . . . C*CATGG . . . 3', at the ATG translational start of the nos gene. The oligonucleotide was hybridized to circular single-stranded M13-3 DNA isolated from virions which had been sedimented out of culture medium. The oligonucleotide:M13-3 hybrid was incubated with DNA ligase and the Klenow fragment of *E. coli* DNA polymerase I, covalently closed circular DNA (cccDNA) was enriched, and the mixture was transformed into JM103. The virions produced by transformants were isolated and used to infect cells at a low multiplicity of infection. RF DNA was isolated from a number of these infected colonies and characterized by restriction mapping. Clones derived from the mutant oligonucleotide-primed strand were identified by the presence of a single NcoI site, which allowed them to be linearized by that enzyme. The mutated clones were further characterized to localize the NcoI site by digestion with ClaI, BamHI (to identify linearized molecules), and ClaI together with NcoI. The mutated M13-3 vector was labeled M13-3A/B18a.

3.3 Moving the Insecticide Gene into M13mp8 p123/58-10 DNA (Example 1.1) was digested with EcoRI and mixed with and ligated to EcoRI-linearized M13mp8 RF DNA. After transformation of the mixture into JM103 and selection of white plaques, two colonies having the insecticide gene-carrying fragment inserted in opposite orientations, were identified by restriction mapping. They were labeled MBT14 and MBT3 and respectively had the sense and antisense strands when in single stranded form.

3.4 Placement of an NcoI Site at the Insecticide Gene Translation Start

An oligonucleotide primer having the sequence 5'GAGGTAACCCATGGATAACAAT3' is synthesized as described in Example 10.1. This oligonucleotide is changed at the two underlined bases from the naturally occurring sequence at the 5'-end of the insecticide structural gene. The change results in the introduction of an NcoI site, 5' . . . C*CATGG . . . 3', at the ATG translational start of the insecticide gene. The oligonucleotide is hybridized to circular single-stranded MBT3 DNA isolated from virions which had been sedimented out of culture medium. The oligonucleotide:MBT3 hybrid is incubated with DNA ligase and the Klenow fragment of *E. coli* DNA polymerase II, cccDNA is enriched, and the mixture is transformed into JM103. The virions produced by the transformants are isolated and used to infect cells at a low multiplicity of infection. RF DNA is isolated from a number of these infected colonies and characterized by restriction mapping. Clones derived from the mutant oligonucleotide-primed strand are identified by the presence of a single NcoI site which allows them to be linearized by that enzyme. The mutated clone is further characterized by restriction enzyme analysis and the presence of the mutant sequence is confirmed by sequencing. The plasmid having the desired sequence is labeled MBT3(Nco).

3.5 Assembly of a Plant Expressible Insecticide Gene in a Shuttle Vector

NcoI- and HindIII-digested MBT3(Nco) RF DNA is mixed with and ligated to a linker, synthesized as described in Example 11.1, having the following structure:

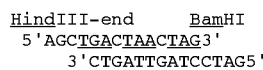

```
HindIII-end    BamHI
5'AGCTGACTAACTAG3'
    3'CTGATTGATCCTAG5'
```

This linker encodes stop codons (underlined) in all three reading phases, and is ended by a functional BamHI site and a HindIII compatible sticky-end incapable of reconstructing a HindIII site. The insecticide gene-bearing DNA fragment is then trimmed by digestion with NcoI and BamHI and is isolated by agarose gel electrophoresis.

pKS111-N (Fink, supra) is a plasmid having a nos gene inserted in Tn5 DNA (from pKS-4) which has a functional kan gene, which is itself inserted in the T-DNA of pKS111. pKS111-N is linearized with SstII and digested to completion with BamHI. M13-3A/B18a is digested with NcoI and SstII and the SstII/NcoI promoter fragment is isolated by agarose gel electrophoresis. The SstII/NcoI promoter and NcoI/BamHI gene fragments are mixed with and ligated to the pKS111-N SstII/BamHI reaction products. The ligation mixture is then transformed into *E. coli* K802. Plasmids isolated from transformants resistant to kanamycin and tetracycline are subjected to restriction enzyme analysis and colonies harboring plasmids identical to pKS111-N except for replacement of a 5'-portion of the nos gene with an insecticide structural gene are identified. Such a plasmid is designated pKS111-NpBt.

3.6 Insertion into TIP Plasmids, Plant Infection and Regeneration

*E. coli* K802(pKS111-NpBt) is mated with *A. tumefaciens* as described in Example 9. The Agrobacterium strains chosen harbor TIP plasmids, based on pTi15955, containing mutations, such as those described in the Background, which facilitate regeneration. Homologous recombinants are selected as described in Example 9 and characterized by restriction mapping. The efficacy of the construction is quickly tested by infection of sunflower stems. The resulting galls are assayed by ELISA and Western blots as described in Example 7 and by bioassay as described in Example 8. As described in Example 6, the Agrobacterium strains are used to infect tobacco cells which are then regenerated. The resulting plants are used as breeding stock to be crossed with various commercial varieties for which insect resistance properties are desired. Regenerated plants and fields of their insecticidal protein-containing descendants are resistant to infestation by larvae of insects such as tobacco hornworm by virtue of the toxic effect such larvae experience when eating tissue from such plants.

Example 4

This example teaches another method of inserting an expressible gene for the *B. thuringiensis* insecticidal protein into a plant genome. The strategy is similar to that described in Example 3 but differs in that a plant promoter is used instead of a T-DNA promoter. The plant gene providing the promoter is phaseolin, which has been shown to be active in species other than its source, the bean *Phaseolus vulgaris* L.

4.1 Moving the Phaseolin Gene into M13mp7

BamHI linkers, having the sequence 5'GGATCC3', are annealed to form double-stranded structures, and blunt-end ligated to form concatamers. These concatamers are partially digested with BamHI to expose 5'GATC . . . 3' sticky-ends, which are compatible with sticky-ends generated by the enzymes BamHI, BclI, BglII, MboI, Sau3AI, and XhoII (5'GATC . . . 3'). A Charon 24A phage clone of phaseolin, 177.4 (Sun, S. M. et al. (1981) Nature 289:37–41; Slightom, J. L. et al. (1983) Proc. Natl. Acad. Sci. USA 80:1897–1901, also designated AG-PVPh177.4) is digested with BglII and BamHI, mixed with and ligated to the concatenated linkers, and completely digested with BamHI to trim the linkers and expose the BamHI sticky-ends, a 3.8 kbp fragment containing the phaseolin gene and 5'- and 3'-flanking sequences is isolated by agarose gel electrophoresis followed by elution. This fragment has BamHI sites at either end as the BamHI/BglII linkage site is not susceptible to the action of either enzyme. The 3.8 kbp BglII/BamHI fragment can also be obtained from p8.8, a pBR322-based subclone of 177.4.

The 3.8 kbp fragment is mixed with and ligated to BamHI-linearized M13mp7 RF. After transformation of the mixture into JM103 and selection of white plaques, two colonies are selected after characterization by restriction and hybridization analysis of RFs and phage DNA. The viral forms of M13-3.8A and M13-3.8S are respectively found to be carrying the antisense and sense strands of the phaseolin gene.

4.2 Placement of an NcoI Site Behind the Phaseolin Promoter

The Phaseolus DNA of M13-3.8A has an NcoI site about 450 bp upstream from the phaseolin transcriptional start. The presence of this site will be inconvenient when one wishes to cleave the plasmid at the NcoI site to be introduced at the phaseolin translational start. Isolated M13-3.8A RF DNA is linearized with NcoI and the 5'-protruding ends are filled in by the action of the Klenow fragment of *E. coli* DNA polymerase I. After blunt-end ligation and transformation into JM103, RF DNAs are isolated and characterized by restriction mapping. A colony is chosen which harbors a vector, labeled M13-3.8Ac, which is lacking the NcoI site of the Phaseolus DNA but is otherwise unchanged from M13-3.8A.

An oligonucleotide primer having the sequence 5 'ATACTACTCTACCATGGTGAGAGCAAGGG3' is synthesized as described in Example 10.1. This oligonucleotide is changed at the underlined bases from the naturally occurring sequence at the 5'-end of the phaseolin gene. The oligonucleotide is hybridized to circular single-stranded M13-3.8Ac DNA isolated from virions which had been sedimented out of culture medium. The oligonucleotide:Mi3–3.8Ac hybrid is incubated with DNA ligase and the Klenow fragment of *E. coli* DNA polymerase I, cccDNA is enriched, and the mixture is transformed into JM103. The virions produced by transformants are isolated and used to infect cells at a low multiplicity of infection. RF DNA is isolated from a number of these infected colonies and characterized by restriction mapping. Clones derived from the mutant oligonucleotide-primed strand are identified by the presence of a novel NcoI site positioned at the 5'-end of the coding sequence. The mutated clones are further characterized to localize the NcoI site by digestion with ClaI and ClaI together with NcoI. The mutated M13-3.8Ac vector is labeled M13-3.8Aa.

4.3 Placement of a HindIII Site at the 3'-end of the Phaseolin Gene

To conveniently introduce the insecticide gene into the phaseolin gene, two additional changes must be made to that phaseolin gene. The first change involves addition of HindIII site (5' . . . A*AGCTT . . . 3') 5' to the polyadenylation site and near the 3'-end of the phaseolin gene. The other important change involves placing translational stop codons (e.g. TAA, TAG, or TGA, underlined below) in all three reading frames. When the oligonucleotide 5'AGGGTG-CATTTGAAGCTTGAATAAGTAAGAACTAAAATGC3' (a) is compared with the 3'-end of the phaseolin gene coding sequence (b), it can be seen to have the desired properties as follows:

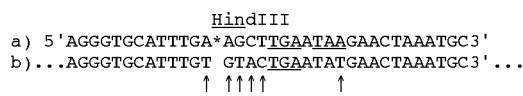
```
                     HindIII
a) 5'AGGGTGCATTTGA*AGCTTGAATAAGAACTAAATGC3'
b)...AGGGTGCATTTGT GTACTGAATATGAACTAAATGC3'...
              ↑ ↑↑↑↑      ↑
```

Note also that this 38-mer has only 6 mismatches, thus insuring good hybridization properties during priming.

The oligonucleotide 5'AGGGTGCATTTGAA GCTTGAATAAGTAAGAACTAAAATGC3', synthesized as described in Example 10.1, is hybridized to single-strand circular M13-3.8Aa DNA purified from virions isolated by centrifugation of culture medium. The oligonucleotide:M13-3.8Aa hybrid is incubated with DNA ligase and the Klenow fragment of *E. coli* DNA polymerase I, cccDNA is enriched, and the mixture is transformed into JM103. The virions produced by the transformants are isolated and used to infect cells at a low multiplicity of infection. RF DNA is isolated from a number of the infected colonies and characterized by restriction enzyme analysis. Clones derived from the mutant oligonucleotide-primed strand are identified by the presence of a HindIII site mapping at the 3'-end of the phaseolin gene, and the presence of mutant sequences at both ends of the structural gene is confirmed by sequencing. A vector containing the desired sequences is labeled M13-3.8Ab.

4.4 Inserting the Insecticide Gene

MBT3(Nco) RF DNA is digested with NcoI and HindIII and is mixed with and ligated to NcoI-and HindIII-digested M13-3.8Ab DNA. The mixture is transformed into K802 and plasmid DNA from kanamycin and/or tetracycline resistant transformants is isolated and characterized by restriction enzyme analysis. A plasmid having the insecticide structural gene inserted between the phaseolin promoter and polyadenylation site is labeled M13-PpBt, and a colony harboring it is chosen.

4.5 Moving the Modified Phaseolin Gene into a Shuttle Vector pKS111-K (Fink, supra) has the Tn5 kan gene from pKS-4 inserted between the HindIII sites of pKS111 T-DNA. M13-PpBt/RF DNA is digested with BamHI and mixed with and ligated to BamHI-linearized pKS111-K (Fink, supra). Plasmids from K802 transformants resistant to kanamycin and/or tetracycline are isolated and characterized by restriction mapping. A colony is selected which harbors a plasmid, labeled pKS111-PpBt, which contains the phaseolin promoter/insecticide structural gene/polyadenylation site combination which, together with a kan gene, is surrounded by octopine T-DNA.

4.6 Insertion into TIP Plasmids, Plant Infection and Regeneration

*E. coli* K802(pKS111-PpBt) is mated with *A. tumefaciens* as described in Example 9. The Agrobacterium strains chosen harbor TIP plasmids, based on pTi15955, containing mutations, such as those described in the Background, which facilitate regeneration. Homologous recombinants are selected as described in Example 9 and characterized by restriction mapping. The efficacy of the construction is quickly tested by infection of sunflower stems. The resulting galls are assayed by ELISA and Western blots as described in Example 7 and by bioassay as described in Example 8. As described in Example 6, the Agrobacterium strains are used to infect tobacco cells which are then regenerated. The resulting plants are used as breeding stock to be crossed with various commercial varieties for which insect resistance properties are desired. Fields of regenerated plants and their insecticidal protein-containing descendants are resistant to infestation by larvae of insects such as tobacco hornworm by virtue of the toxic effect such larvae experience when eating tissue from such plants.

Example 5

Regeneration in this Example involves carrot tumors incited by Ri-based TIP plasmids and is effected essentially as described by Chilton, M-D. et al. (1982) Nature 295:432–434.

5.1 Infection with Hairy Root

Carrot disks are inoculated with about 109 bacteria in 0.1 ml of water. One to 1.5 cm segments of the ends of the roots obtained are cut off, placed on solid (1–1.5% agar) Monier medium lacking hormones (Tepfer, D. A. and Tempe, J. C. (1981) Cr. Hebd. Seanc. Acad. Sci., Paris 295:153–156), and grown at 25° C. to 27° C. in the dark. Cultures uncontaminated by bacteria are transferred every 2 to 3 weeks and are subcultured in Monier medium lacking hormones and agar. Transformed roots can be recognized by their aberrant morphology and selected.

5.2 Regeneration of Roots to Plants

The cultured root tissue described in Example 5.1 is placed on solidified (0.8% Agar) Monier medium supplemented with 0.36 $\mu$M 2,4-D and 0.72 $\mu$M kinetin. After 4 weeks, the resulting callus tissue is placed in liquid Monier medium lacking hormones. During incubation at 22 to 25° C. on a shaker (150 rpm) for one month, the callus disassociates into a suspension culture from which embryos differentiate, which, when placed in Petri dishes containing Monier medium lacking hormone, develop into plantlets. These plantlets are grown in culture, and after "hardening" by exposure to atmospheres of progressively decreasing humidity, are transferred to soil in either a greenhouse or field plot.

5.3 Use of Non-hairy Root Vectors

Ti-based vectors which do not have functional tmr genes are used instead of the Ri-based vectors as described by Hall, T. C. et al., U.S. applications, Ser. Nos. 485,613 and 485,614. Construction of suitable mutants can be done by those skilled in the art, and is reviewed in the Background.

Example 6

Regeneration in this Example involves tobacco tumors incited by a Ti-based TIP plasmid and is effected essentially as described by Barton, K. A. et al. (1983) Cell 32:1033–1043.

6.1 Infection with Crown Gall

Tobacco tissue is transformed using an approach utilizing inverted stem segments first described by Braun, A. C. (1956) Canc. Res. 16:53–56. Stems are surface sterilized with a solution that was 7% commercial Clorox and 80% ethanol, rinsed with sterile distilled water, cut into 1 cm segments, placed basal end up in Petri dishes containing agar-solidified MS medium (Murashige, T. and Skoog, F. (1962) Physiol. Plant. 15:473–497) lacking hormones. Inoculation is effected by puncturing the cut basal surface of the stem with a syringe needle and injecting bacteria. Stems are cultured at 25° C. with 16 hours of light per day. The calli which develop are removed from the upper surface of the stem segments, are placed on solidified MS medium containing 0.2 mg/ml carbenicillin and lacking hormones, are transferred to fresh MS-carbenicillin medium three times at intervals of about a month, and are tested to ascertain whether the cultures had been rid of bacteria. The axenic tissues are maintained on solidified MS media lacking supplements under the culture conditions (25° C.; 16 hr.:8 hr. light:dark) described above.

6.2 Culture of Transformed Tissue

Clones are obtained from the transformed axenic tissues as described by Binns, A. and Meins, F. (1979) Planta 145:365–369. Calli are converted into suspensions of cells by culturing in liquid MS having 0.02 mg/l naphthalene acetic acid (NAA) at 25° C. for 2 or 3 days while being shaken at 135 rpm, and filtering in turn through 543 and 213 $\mu$m stainless steel meshes. The passed filtrate is concentrated, plated in 5 ml of MS medium containing 0.5% melted agar, 2.0 mg/l NAA, 0.3 mg/l kinetin and 0.4 g/l Difco yeast extract at a density of about $8\times10^3$ cells/ml. Colonies reaching a diameter of about 1 mm are picked by scalpel point, placed onto and grown on solidified MS medium having 2.0 mg/l NAA, 0.3 mg/l kinetin and about 10 $\mu$g/ml S-(2-aminoethyl)-L-cysteine (AEC). (A range of concentrations of AEC, between about 2 $\mu$g/ml and about 30 $\mu$g/ml, is tried as the exact concentration effective for selection will depend on the variety of tobacco used and the growth conditions to which the source plant and tissues derived from it are subjected.) AEC has been shown to be an agent capable of selecting tissue containing octopine synthase (Dahl, G. A. and Tempe, J. (1983) Theor. Appl. Genet. 66:233–239). Alternatively, the filtrate is plated at low density (several hundred cells per ml) on a filter paper overlaying a feeder layer of tobacco cells growing on the solidified MS/NAA/kinetin/yeast extract medium. When 1 mm colonies have formed the entire filter paper is transferred to a petri dish containing the solidified MS/NAA/kinetin/AEC medium. The resulting calli which do not show the effects of AEC toxicity are selected, split into pieces, and tested for other transformed phenotypes such as production of octopine and hormone independent growth.

6.3 Regenerator of Plants

Transformed clones are placed onto solidified MS medium having 0.3 mg/l kinetin, and cultured as described in Example 6.1. The shoots which form are rooted by putting them on a solid (1.0% agar) medium containing ⅒ strength MS medium salts, 0.4 mg/l thiamine, lacking sucrose and hormones, and having a pH of 7.0. Rooted plantlets are grown in culture, hardened as described in Example 5.2, and are transferred to soil in either a greenhouse or field plot. Plants are screened for retention of the transformed phenotype by methods, well-known to those skilled in the art, such as Southern, Northern and dot blots with appropriate probes, octopine assays, immunological (see Example 7) or biological (Example 8) assays for presence of crystal protein.

6.4 Vectors Used

Constructions described by Hall, T. C. et al., U.S. application Ser. Nos. 485,613 and 485,614 are suitable Ti-based vectors lacking functional tmr genes. The method described in Example 6.1 for infection of inverted stem segments is often useful for the establishment of TIP-transformed plant cell lines.

Example 7

Anti-insecticidal protein antibody was produced by methods well-known to those skilled in the art of immunology. "Western" blots, to detect antigens after SDS-polyacrylamide gel electrophoresis, were done essentially as described by Legocki, R. P. and Verma, D. P. S. (1981) Anal. Biochem 111:385–392.

Micro-ELISA (enzyme-linked immuno-sorbant assay) assays are done using Immulon-2 type plates having 96 wells by the following steps:

7.1 Binding Antibody to Plates

On day one, the wells are coated with 1:1000 dilution of antibody (rabbit anti-insecticidal protein IgG) in coating buffer. 200 $\mu$l/well is incubated at 37° C. for 2–4 hours. The plates are covered with Saran Wrap during this incubation. Afterwards the plates are rinsed three times with phosphate buffered saline-Tween (PBS-Tween) allowing a five-minute waiting period between each rinse step. Then 1% borine serum albumin (BSA) is added to rinse and, after addition to the well, left to sit for 20 minutes before discarding. Rinsing is repeated five times more with PBS-Tween.

7.2 Tissue Homogenization

The tissue is sliced up into small pieces and then homogenized with a polytron using 1 gm of tissue/ml. phosphate buffered saline-Tween-2% poly vinyl pyrrolidone-40 (PBS-Tween-2% PVP-40). All samples are kept on ice before and after grinding and standard curves were obtained. One standard curve is done in tissue homogenates and one standard curve is also done in buffer to check the recovery of insecticidal protein from homogenized tissue or cells. Following centrifugation of the homogenized samples, 100 $\mu$l of each sample is placed in a well and left overnight at 4° C. To avoid errors, duplicates of each sample are done. The plates are sealed during incubation.

7.3 Binding Enzyme

After the overnight incubation, the antigen is discarded and the wells are washed five times with PBS-Tween allowing 5 minutes between each rinse.

A conjugate (rabbit anti-insecticidal protein IgG alkaline phosphatase-linked) is the diluted 1:3000 in PBS-Tween-2% PVP containing 0.2% BSA and 150 is added to each well; followed by incubation for 3–6 hours at 37° C. After the incubation, the conjugate is discarded and the wells are rinsed five times with PBS-Tween, allowing five minutes between each rinse as before.

7.4 Assay

Immediately before running the assay, a 5 mg tablet of p-nitrophenyl phosphate (obtained from Sigma and stored frozen in the dark) is added per 10 ml substrate and vortexed until the tablet is dissolved. 200 $\mu$l of the room temperature solution is quickly added to each well. The reaction is measured at various times, e.g. t=0, 10, 20, 40, 60, 90 and 120 minutes, using a Dynatech Micro-ELISA reader. When p-nitrophenyl phosphate, which is colorless, is hydrolysed by alkaline phosphatase to inorganic phosphate and p-nitrophenol, the latter compound gives the solution a yellow color, which can be spectrophoto-metrically read at 410 nm.

Example 8

Insects were obtained from commercial sources and kept essentially as described by Bell, R. A. and Joachim, F. G. (1976) Ann. Entomol. Soc. Amer. 69:365–373, or Yamamoto, R. T. (1969) J. Econ. Entomol. 62:1427–1431. Bioassays for insecticidal protein were done by feeding extracts to larvae of Manduca sexta essentially as described by Schesser, J. H. et al. (1977) Appl. Environ. Microbiol. 33:878–880.

Example 9

Triparental matings were generally accomplished as described below; other variations known to those skilled in the art are also acceptable. E coli K802 (pRK290-based shuttle vector) was mated with E. coli (pRK2013) and a TIP plasmid harboring A. tumefaciens strain resistant to streptomycin. The pRK2013 transferred to the shuttle vector carrying strain and mobilized the shuttle vector for transfer to the Agrobacterium. Growth on a medium containing both streptomycin and the drug to which the shuttle vector is resistant, often either kanamycin or chloramphenicol, resulted in the selection of Agrobacterium cells containing shuttle vector sequences. A mating of these cells with E. coli (pPH1J1) resulted in the transfer of pPH1J1 to the Agrobacterium cells. PpH1J1 and pRK290-based shuttle vectors cannot coexist for long in the same cell. Growth on gentamycin, to which pPH1J1 carries a resistance gene, resulted in selection of cells having lost the pRK290 sequences. The only cells resistant to streptomycin, gentamycin, and kanamycin are those which have Ti plasmids that have undergone double-homologous recombination with the shuttle vector and now carry the desired construction. pRK290 and pRK2013 were disclosed by Ditta, G. et al. (1980) Proc. Natl. Acad. Sci. USA 77:7347–7357, and pPH1J1 by Hirsh, P. R. (1978) Thesis, Univ. E. Anglia.

Example 10

This Example describes techniques for the synthesis and use of synthetic oligonucleotides. Other useful references can be found in the list of works cited in the section introductory to these Examples.

10.1 Oligonucleotide Synthesis

The techniques for chemical synthesis of DNA fragments used in these Examples utilize a number of techniques well-known to those skilled in the art of DNA synthesis. The modification of nucleosides is described by Schaller, H. et al. (1963) J. Amer. Chem. Soc. 85:3821–3827. The preparation of deoxynucleoside phosphoramidites is described by Beaucage, S. L. and Caruthers, M. H. (1981) Tetrahedron Lett. 22:1859. Preparation of solid phase resin is described by Adams, S. P. et al. (1983) J. Amer. Chem. Soc. Hybridization procedures useful during the formation of double-stranded synthetic linkers are described by Rossi, J. J. et al. (1982) J. Biol. Chem. 257:9226–9229.

10.2 Use for Oligonucleotides

Use of synthetic oligonucleotides to reconstruct a deleted segment of a gene has been exemplified by Hall, et al., U.S. application Ser. No. 485,614. Use of synthetic oligonucleotides to link otherwise incompatible restriction site sticky-ends has been exemplified by Hall et al., U.S. application Ser. No. 485,614 and is well-known to those skilled in the art of recombinant DNA manipulations.

10.3 Oligonucleotide-directed Mutagenesis

General methods of directed mutagenesis have been reviewed recently by Shortle, D. et al. (1981) Ann. Rev. Genet. 15:265–294. Of special utility in manipulation of genes is oligonucleotide-directed site-specific mutagenesis, reviewed recently by Zoller, M. J. and Smith, M. (1983) Methods Enzymol. 100:468–500 and Smith, M. and Gillam, S .(1981) in Genetic Engineering; Principles and Methods, Vol. 3, Setlow, J. K. and Hollaender, A. (eds.); and Smith, M. (1982) Trends in Biochem. 7:440–442. This technique permits the change of one or more base pairs in a DNA sequence or the introduction of small insertions or deletions. Recent examples of use of oligonucleotide-directed mutagenesis include Zoller, M. J. and Smith, M. (1983) supra; Zoller, M. J. and Smith, M. (1982) Nucl. Acids Res. 10:6487–6500; Dalbadie-McFarland, G. et al. (1982) Proc. Natl. Acad. Sci. USA 79:6409–6413; Simons, G. F. M. et al. (1982) Nucl. Acids Res. 10:821–832; and Hutchison, C. A., III et al. (1978) J. Biol. Chem. 253:6551–6560. Useful M13-based vectors (e.g. mWB2344) have been reported by Barnes, W. M. et al. (1983) Methods Enzymol. 101:98–122; and Barnes, W. M. and Bevan, M. (1983) Nucl. Acids Res. 11:349–368.

The sequence to be modified usually is moved into a single-stranded bacteriophage vector, here one derived from M13, by standard techniques well-known to those in the art. The vector DNA is generally in the double-stranded replicative form (RF), as the single-stranded viral form cannot ordinarily be "cut and spliced" by restriction enzymes and ligases. After in vitro ligation of the fragment into the RF, transformation into a suitable host, and production of single-stranded DNA (ssDNA) as part of the life cycle of the vector the ssDNA is isolated from phage particles and hybridized to an oligonucleotide having sufficient length and sequence homology to hybridize to the vector in the appropriate location. The oligonucleotide should have the sequence desired as an end product and otherwise differ in no way from the sequence to be changed. Once a hybrid is formed comprising a ssDNA circle base paired to the oligonucleotide carrying the mutant sequence, the oligonucleotide primes synthesis- of a complementary strand of DNA by the Klenow fragment of E. coli DNA polymerase I, a polymerase lacking a 5'-to-3' exonuclease activity. The vector is optionally incubated with DNA ligase and the polymerase and ligase reactions may be done simultaneously. Preferentially covalently closed-circular double-stranded DNA (cccDNA) molecules can be selected before transformation by techniques which include alkaline sucrose gradient centrifugation, extraction with phenol under alkaline conditions, and incubation with S1 nuclease. The vector can now be transformed into an appropriate bacterial host cell. Virus particles from this initial infection are isolated and used to form plaques by infecting a lawn of bacteria. In cases where one is changing a restriction site, one may readily screen RFs by restriction enzyme analysis. One may also screen by hybridization under carefully selected conditions using the synthetic mutant oligonucleotide primer as a probe, or by DNA sequencing. When a clone containing the desired change has been isolated, one may manipulate the now mutant DNA as desired using techniques well-known to those skilled in the art.

Example 11

This Example teaches isolation of a clone having the 3'-end of the insecticide gene carried by p123/58-10, and the reconstruction of a full-length HD-73 crystal protein gene.

11.1 Cloning of an Insecticide Gene 3'-end

Immunodetection of electrophoretically separated peptides on protein blots and DNA sequencing showed that p123/58-10 and p123/58-3 each contained a partial protoxin gene. To reconstruct a complete protoxin gene, flanking DNA restriction sites were identified by Southern blots of restriction digests, a well-known technique, and overlapping clones were selected from a PstI library made from 50 MD plasmid-enriched DNA as follows. 50 MD plasmid DNA, enriched by sucrose gradient centrifugation as above, was digested to completion with PstI, mixed with and ligated to PstI-linearized pBR322, and transformed into HB101. Tetracycline-resistant transformants were screened essentially as described by Benton, W. D. and Davis, R. W. (1977) Science 196:180–182, using a probe nick-translated from the 6.7 kbp HindIII insert of p123/58-10. Plasmid DNAs isolated from strains which bound the probe were characterized by restriction enzyme analysis. A strain chosen for further work harbored pBt73-161, which contains the 3'-end of a crystal protein gene.

11.2 Construction of a Full-length Insecticide Gene

The 5'- and 3'-ends of the protoxin gene were fused together at the unique HindIII site to form a complete protoxin gene. p123/58-10 DNA was digested with BamHI, ligated to itself, and transformed into HB101. Plasmid DNAs from ampicillin-resistant transformants were characterized by restriction enzyme analysis and a strain was identified that harbored a plasmid, designated pBt73-10 (Bam), having single BamHI and HindIII sites due to deletion of a small HindIII site-bearing BamHI fragment. A 5 kbp HindIII fragment of pBt73-161, isolated by agarose gel electrophoresis, was mixed with and ligated to HindIII-digested dephosphorylated (by bacterial alkaline phosphatase) pBt73-10(Bam) DNA. After the ligation mixture was transformed into HB101, plasmid DNA isolated from ampicillin-resistant tetracycline-sensitive transformants was characterized by restriction enzyme analysis. A transformant was identified that harbored a plasmid, designated pBt73-16, carrying a complete protoxin gene. *E. coli* HB101 (pBt73-16) is on deposit at the Northern Regional Research Center, 1815 N. University St., Peoria, Ill. 61604 USA, as NRRL B-15759.

Example 12

This Example teaches the insertion of the full-length *Bacillus thuringiensis* insecticide gene between a T-DNA gene promoter and a polyadenylation (poly(A) addition) signal, the transfer of the insecticide gene to tobacco via a sub-Ti plasmid, the regeneration of plants containing the gene, and the expression of this gene under control of the T-DNA promoter in plant cells.

12.1 Preparation of pH400, a Sub-Ti Plasmid pH4-1 DNA can be isolated from *E. coli* K802 (pH4-1), which has been deposited as NRRL B-18009. pH4-1 is a sub-Ti plasmid based on pSUP106 (Priefer, U. B. et al. (1985) J. Bacteriol. 163:324–330; *E. coli* CSH52 (pSUP106) is deposited as NRRL B-15486). Inserted into pSUP106's HindIII site is pTi15955 DNA having border A (the left border of $T_L$) a plant-expressible selectable marker, the 5'-end of tml, a complete ocs gene, and border B (the right border of $T_L$). The plant-expressible selectable marker is sutured to the adjoining pTi15955 sequences at BglII sites made up of a Tn5 neomycin phosphotransferase II (NPT2) structural gene capable of detoxifying kanamycin and related antibiotics (a kan gene). The NPT2 structural gene is transcribed in plant cells under control of a cauliflower mosaic virus (CaMV; for a review of CaMV see Hohn, T. et al. (1982) Curr. Top. Microbiol. Immunol. 96:193–236) 19S transcript promoter and a pTi15955 ORF26 (as defined by Barker, R. F. et al. (1983) Plant Mol. Biol. 2:335–350) polyadenylation site. The NPT2 structural gene is oriented so that it is transcribed in the same direction as the ocs gene. In other words, the T-DNA of pH4-1 is essentially identical to $T_L$-DNA of pTi15955 except for substitution of a CaMV 19S promoter/NPT2 structural gene/ORF26 polyadenylation site combination for T-DNA between the position 1617 BglII site and the position 11207 SmaI site, T-DNA positions being defined by Barker et al., supra.

pH4-1 has two BglII sites, both of which flank the kan selectable marker. One of the BglII sites was removed, thereby leaving a unique BglII site useful for insertion of extraneous coding DNA. pH4-1 DNA was linearized by being partially digested with BglII and full-length, linear DNA was electrophoretically isolated. The BglII sticky-ends were then removed by incubation with the Klenow fragment of *E. coli* DNA polymerase I. The resulting blunt-ended DNA was ligated to itself and transformed into *E. coli*. Plasmid DNAs isolated from transformants resistant to chloramphenicol were screened by restriction analysis and a colony was identified which harbored a plasmid designated pH400. pH400 is identical to pH4-1 except for the absence of the BglII site between the kan gene and the ORF1 promoter, the unique pH400 BglII site being located between the kan gene and the ocs gene. The single BglII site is a convenient place to insert DNA, in particular if that DNA has compatible 5'GATC . . . 3' sticky-ends resulting from the action of BglII, BclI, or BamHI.

12.2 Preparation of pDOB513 pDOB512, carrying cauliflower mosaic virus (CaMV) transcription controlling sequences (obtained from Dr. Ken Richards, Centre National de la Recherche Scientifique, Institute de Biologie Moleculaire et Cellulaire, 15, rue Descartes, F-67084 Strasbourg, France) was constructed as follows: A HindIII fragment carrying the CaMV 19S RNA promoter region (CaMV nucleotides 5376–5851) was inserted into pBR322 and was trimmed back to within one base pair of the 19S transcript cap site. An adapter molecule having both a SmaI site and a BamHI (the structure being 5'CCCGGGGATCCGG3':5'CCGGATCCCCGGG3', see below) was then ligated to the trimmed DNA. A HincII fragment carrying the CaMV 19S transcript terminator (CaMV nucleotides 7018–7794) to which BamHI linkers had been added was then inserted behind the 19S promoter, the promoter and terminator being separated by the SmaI/BamHI linker. The resulting plasmid is designated pDOB412. pDOB412 DNA was digested with BglII and SalI, filled in by incubation with the Klenow fragment of *E. coli* DNA polymerase I, and religated, thereby deleting DNA, which includes BamHI and HindIII sites, between the CaMV position 7644 BglII site and the pBR322 position 650 SalI site and regenerating a BglII site. The resultant plasmid was designated pDOB512.

The sticky-ends of HindIII-linearized pDOB512 DNA were converted to blunt-ends. The blunt-ended pDOB512 DNA was mixed with and ligated to commercially available BglII linkers. The ligation mix was transformed into *E. coli* K802 and an ampicillin-resistant transformant was isolated which harbored a plasmid, designated pDOB513 (FIG. 3). pDOB513 has CaMV 19S transcription controlling sequences on a BglII fragment. SmaI and BamHI sites are found between the DNA segments having the promoter and the polyadenylation site in both pDOB412, pDOB512, and pDOB513, thereby providing a convenient location for insertion of foreign DNA that is to be a template for a transcript. The sequence of this suture is as follows:

```
                    BamHI
               SmaI
5'...GAGAAAATCAGCCCGGGGATCCGGAACA...3'
```

The first underlined base, an A, corresponds to the first base of the 19S mRNA, transcription being towards the right, and the second and third underlined bases, respectively a G and an A, are derived from CaMV sequences at positions 5765 and 7018, respectively, as defined by Hohn et al., supra.

12.3 Preparation of T-DNA ORF24 Transcription Controlling Sequences pKS-proI was prepared essentially as described in Example 2.2. pKS111 is a recombinant plasmid having Ti15955 T-DNA which spans the sequence between EcoRI sites at positions 16,202 and 21,631 (as defined by Barker, et al., (1983) supra) inserted into the EcoRI site of pRK290 (Ditta, G. et al. (1980) Proc. Natl. Acad. Sci. USA 77:7347–7351). *E. coli* K802 (Wood, W. B. (1966) J. Mol. Biol. 16:118) methylates DNA at many, but not all, ClaI sites, thereby specifically protecting certain sites from the action of ClaI. The only susceptible ClaI sites of pKS111 are the sites at T-DNA positions 18,892 and 20,128. These sites define a DNA fragment which includes the ORF24 (as defined by Barker, et al., (1983) supra) structural gene but does not include the ORF24 promoter or polyadenylation site. ORF24 is associated with mannopine synthesis. Plasmid DNA isolated from *E. coli* K802 (pKS111) was digested with ClaI, ligated to itself, and transformed into K802. A tetracycline-resistant transformant was identified by restriction analysis which harbored a plasmid, designated pKS-proI (or alternatively, pTR-proI), identical to pKS111 except for deletion of a fragment which spanned the ClaI sites at positions 18,892 and 20,128.

pTR-proI DNA was isolated and cleaved at its single ClaI site (the suture between the sites at positions 18,892 and 20,128) by incubation with ClaI. After the ClaI sticky-ends were then removed by incubation with the Klenow fragment of *E. coli* DNA polymerase I, the blunt-ended DNA was mixed with and ligated to commercially available BamHI linkers having the self-complementary sequence 5' CGGATCCG3'. After digestion of the BamHI-linked DNA with BamHI, religation to itself, and transformation of the resulting DNA into K802, plasmid DNAs were isolated from transformants resistant to tetracycline and were characterized by restriction mapping. A colony was identified which harbored a plasmid, designated pTR-proI(Bam), lacking a ClaI site at t he T-DNA positions 18,892/20,128 suture but, instead, having a BamHI site at the former location of that ClaI site.

pBR322 has a BamHI site which is inconvenient for later manipulations. Therefore, the T-DNA of the ClaI-deleted pKS111-derivative was transferred to a pBR325 derivative which was lacking a BamHI site. pBR325 DNA, isolated from *E. coli* GM33 (pBR325), was digested with both BamHI and BclI, was ligated to itself and was transformed into *E. coli*. GM33 (Marinus, M. G. and Morris, R. N. (1974) J. Mol. Biol. 85:309–322) does not methylate adenine residues of DNA. Plasmid DNA isolated from transformants sensitive to tetracycline and resistant to chloramphenicol and ampicillin were characterized by restriction mapping and a colony was identified which harbored a plasmid, designated pBR325aBB, which could not be cleaved with either BamHI or BclI. pTR-proI DNA was digested with EcoRI and was mixed with and ligated to EcoRI-linearized, dephosphorylated pBR325aBB DNA. After transformation into *E. coli*, plasmid DNAs isolated from transformants resistant to ampicillin and sensitive to both chloramphenicol and tetracycline were characterized by restriction mapping. A colony was identified which harbored a plasmid, designated p403B, having the ClaI-deleted T-DNA with BamHI linkers in the former ClaI site, recombined with the pBR325aBB vector.

pKS4.2 DNA (Example 2.3) was digested with ClaI and a fragment carrying the kan gene was electrophoretically isolated. This fragment was mixed with and ligated to ClaI-linearized pBR322 and transformed into *E. coli*. Plasmid DNAs isolated from transformants resistant to ampicillin and kanamycin were screened by restriction analysis and a colony was identified which harbored a plasmid designated pKS4.3. The pKS4.3 kan gene was oriented with its 5'-end and 3'-end respectively proximal to the pBR322 EcoRI and BamHI sites. In this orientation, the kan gene may be removed on a HindIII fragment.

BamI-linearized pBR322 DNA was mixed with and ligated to BglII-digested bacteriophage lambda DNA. Transformation into *E coli* cells was followed by selection for resistance to ampicillin and screening for sensitivity to tetracycline. Plasmid DNAs were then isolated and screened by restriction analysis and a colony was identified which harbored a plasmid, designated pBR322Bam-, which could not be cleaved with BamHI.

pKS4.3 DNA was digested with HindIII and the kan gene-bearing fragment was electrophoretically isolated. The kan fragment was then mixed with and ligated to HindIII-linearized pBR322Bam-DNA. The ligation mixture was then transformed into *E. coli*. Plasmid DNAs isolated from transformants resistant to both kanamycin and ampicillin were screened by restriction analysis and a colony was identified which harbored a plasmid, designated p11-83c, having the kan fragment inserted into pBR322 Bam-'s HindIII site. In p11-83c the kan gene was oriented so that the kan gene was transcribed in the same direction as the ampicillin resistance (amp) gene.

pTR-proI(Bam) was digested with EcoRV and an approximately 2.26 kbp fragment bearing the ORF24 ("1.6" transcript) promoter and polyadenylation site, but lacking the ORF24 structural gene, was electrophoretically isolated. The EcoRV sticky-ends were then converted to blunt-ends by the action of the Klenow fragment of *E. coli* DNA polymerase I. The blunt-ended fragment was then mixed with and ligated to commercially available BglII linkers. After trimming off excess linkers by digestion with BglII, the fragment was mixed with and ligated to BglII-linearize p11-83c DNA. The ligation mixture was then transformed into *E. coli*. Plasmid DNAs isolated from ampicillin-resistant, kanamycin-sensitive transformants were restriction mapped and a colony was identified which harbored a plasmid, designated pCG116, having a BglII fragment bearing the ORF24 promoter and polyadenylation site inserted into Tn5 DNA between the kan promoter and kan structural gene.

pDOB513 DNA was digested with BglII, religated to itself, and transformed into K802. Colonies which harbored a plasmid, designated pDOB514, deleted for CaMV transcription controlling sequences were identified by restriction mapping of the harbored plasmids.

pCG116 DNA, which had, on a 2.26 kbp BglII fragment, a BamHI site between the ORF24 promoter, and transcript terminator, was then digested with BglII, which cleaves at sites which in T-DNA correspond to positions 18,027 and 21,522 EcoRI sites. The restriction digested DNA was mixed with and ligated to BglII-linearized pDOB514 DNA. Plasmid DNAs of ampicillin-resistant transformants were characterized by restriction mapping, and a colony was identified which harbored a plasmid, designated pMAN514, having a 2.29 kbp BglII fragment carrying an ORF24 promoter and polyadenylation site separated by a BamHI site.

12.4 Preparation of the Insecticide Gene

After pBt73-16 DNA was digested with NdeI, resulting NdeI sticky-ends were filled in by incubating the mixture with T4 DNA polymerase and all four dNTPs. The blunt-ended Bacillus DNA was mixed with and ligated to double-stranded, SmaI-linearized, M13mp19 RF DNA (Norrander, J. et al. (1983) Gene 26:101–106). The ligation mixture was transformed into *E. coli* JM105. DNAs isolated from plaques that were "clear" when plated on indicator plates were characterized by restriction analysis and a plaque was identified which harbored a vector, designated 1.6.4, having a 3.6 kbp Bacillus DNA oriented such that single-stranded form was complementary to crystal protein mRNA (i.e. the phage carried the antisense strand).

A BamHI site was introduced into the Bacillus DNA immediately 5'- to the crystal protein translational start site essentially as described in Example 10. Sequences of the unmutated Bacillus DNA and the oligonucleotide primer are as follows:

```
Bacillus:   5'...GAGATGGAGGTAACTTA^H_T^H_G^H_GATAAC...3'
Primer:        5'GAGATGGAGGATCCTTATGGATAAC3'
                        BamHI   MetTyrHis...
```

Putative mutant DNAs were screened for hybridization under stringent conditions to a 32P-label derivative of the oligonucleotide primer and for the presence of a novel BamHI site. A plaque was identified harboring a vector designated 1.6.4B–3.8.3, having a BamHI site immediately 5'- to the translational start. Fidelity of the in vitro mutation was confirmed by DNA sequencing. The insecticidal protein structural gene may be removed from double-stranded 1.6.4B–3.8.3 RF DNA on a 3.75 kbp BamHI fragment resulting from cleavage at the novel site in the Bacillus sequence and a BamHI site which is 3'-to the structural gene in the M13mp19 polylinker.

12.5 Combination of an Insecticidal Protein Structural Gene with ORF24 Transcription Controlling Sequences Double-stranded 1.6.4B–3.8.3 RF DNA and pCG116 DNA, both having been digested with BamHI, were mixed with each other and ligated together. After the ligation mixture was transformed into *E. coli*, plasmid DNAs isolated from ampicillin-resistant transformants were characterized by restriction analysis. A colony was identified which harbored a plasmid, designated pCJ161, having a full-length insecticidal protein structural gene placed between the ORF24 promoter and ORF24 polyadenylation site in an orientation such that the mRNA transcribed under control of the ORF24 promoter encodes the insecticidal protein.

12.6 Insertion of a Plant-expressible Insecticide Gene into a Sub-Ti Plasmid pCJ161 and pH400 DNAs, having been digested with BglII, were mixed with each other and ligated together. After the ligation mixture was transformed into *E. coli*, plasmid DNAs isolated from ampicillin-resistant transformants were characterized by restriction analysis. A colony was identified which harbored a plasmid, designated pH450, having the ORF24 promoter/crystal protein structural gene/ORF24 polyadenylation site combination inserted into the pH400 BglII site, which is located between the ocs gene and the plant-expressible kan gene. The plant-expressible crystal protein gene of pH450 is oriented so that it is transcribed in the same direction, i.e., off of the same DNA stand, as both the ocs gene and the kan gene.

12.7 Plant Transformation pH450 was transferred into *A. tumfaciens* LBA4404 (Ooms, G. et al. (1981) Gene 14:33–50), a vir gene-bearing, micro-Ti-mobilizing strain, by the triparental mating technique. Tobacco leaf tissues was inoculated using a modification of the method of Horsch, R. B. et al. (1985) Science 227:1229–1231. Leaf segments were dipped in the inoculating suspension of bacteria for 1–3 min. The inoculating bacterial suspensions had titres of 107–108 ml-1; the exact concentration was found to be unimportant. The medium was a tobacco regenerating medium having MS salts, a mixture well-known to the art, supplemented with 0.1 mg/l p-chlorophenoxyacetic acid (pCPA), 7.5 mg/l 6-(2,2-dimethylallylamino)-purine (2iP), 300 mg/l kanamycin, and 125 mg/l cloxacillin, mefoxin and 500 mg/l carbenicillin. Generally 75–80% of the shoots were able to root in a kanamycin-containing medium and all were transformed. Some kanamycin-resistant shoots did not make measurable quantities of octopine.

12.8 Expression in Plant Tissue: Immunoassay

Micro-ELISA double antibody sandwich assays were performed using a modification of the method of Example 7.

Antibodies were prepared by well-known methods. Coating antibody was partially purified mouse polyclonal antisera which was raised to *B. thuringiensis* HD73 crystal protein. The mouse antisera was partially purified by precipitation with 50% (w/v) saturated ammonium sulfate at pH 7.4. The milky precipitate that forms during 30 min. on ice was pelleted by centrifugation (20 min., 10,000 rpm). The pellet was then resuspended in phosphate buffered saline (PBS, pH 7.4) containing 137 mM NaCl, 1.5 mM $KH_2PO_4$, 2.7 mM KCl and 8 mM $NaHPO_4$. The resulting coating antibody sample was then dialyzed overnight in PBS at 4° C.

Primary antibody was partially purified rabbit polyclonal antisera raised to *B. thuringiensis* HD73 crystal protein. This antisera was cleared of antibodies that react with tobacco leaf protein. Tobacco leaf protein was bound to CNBr activated Sepharose 4B (Pharmacia, Upsalla, Sweden) (10 mg protein/ml gel). Rabbit serum was diluted 1:4 (v/v) with PBS and added to the swollen Sepharose gel to which the leaf protein was bound. About 2–3 ml of gel was used for 4 ml of diluted serum. The serum-gel mixture was incubated with gentle shaking for about 1 hr. at room temperature. Antibodies that react with leaf protein remain bound to the gel. The liquid containing unbound antibodies was removed from the gel matrix by aspiration. The antibody solution was then partially purified by precipitation with 50% saturated ammonium sulfate followed by overnight dialysis against PBS at 4° C.

Secondary antibody was commercial goat anti-rabbit IgG (H+L) labelled with alkaline phosphatase (Kirkegaard and Perry, Gaithersburg, Md.). Sterile, distilled water (1 ml) was added to 0.5 mg of lyophilized pellet. The wells of disposable flexible 96-well/flat-bottom microtitration plates (Dynatech, Alexandria, Va.) were coated (100 $\mu$l/well) with coating antibody (1:2000 dilution of coating antibody in coating buffer). Coating buffer contained 5 mM $Na_2HCO_3$ and 35 mM $NaHCO_3$ at pH 9.6. After addition of the coating antibody solution, the plates were covered and stored at 4° C. for at least 12 hours. The contents of the wells were then discarded and the entire plate was rinsed about 3–4 times with a wash buffer of PBS containing 0.05% polyoxyethylenesorbitan monolaurate (Tween-20). Plates were then filled with wash buffer and placed on a shaker for 5 min. followed by a final rinse. The plates were then drained for 30 seconds. It is important that at no point in the assay the wells dry for a prolonged period. In between assay steps the wells were filled with wash buffer.

The plates were next treated with blocking solution to prevent non-specific binding of proteins. Plate wells were filled with blocking solution containing 1% (w/v) BSA (bovine serum albumin); 1% (w/v) casein, acid hydrolysate, type 1; and 0.05% (v/v) polyoxyethylenesorbitan monolaurate (Tween-20) and allowed to stand at room temperature for 30 min. to 1 hr.

Tobacco plant tissue samples were prepared from leaf material. Generally, 1 or 2 leaves from the apex of the plant were combined with 4 or 5 leaf disks (7 mm) from the basal and marginal regions of the next youngest leaves. Tissue samples of about 100 mg were used. After weighing, tissue samples were quick frozen in liquid nitrogen and ground in a tissue grinder. The sample was allowed to warm to room temperature during grinding. After the tissue is completely ground, PBS was added to make a solution containing 0.3 mg fresh weight/µl (for a 100 mg sample, 500 µl of PBS was added). Callus tissue samples were prepared in the same manner, except that PBS was added to ground tissue to give a solution of 0.5 mg fresh weight/µl. Samples were then mixed thoroughly and allowed to stand at 4° C. (about 20 min.) for tissue to settle out. Samples (10–15 µl) of the supernatant were taken for total protein assays. Samples were then diluted with an equal volume of a 2× concentration of sample buffer. Sample buffer (1×) contained PBS (pH 7.4) with 2% (v/v) polyethylene glycol, 1% (v/v) polyvinyl pyrolidone, 0.1% (w/v) BSA, 0.1% (w/v) Casein, acid hydrolysate, 10 µg/ml Aprotinin (Sigma), a protease inhibitor, 0.05% (v/v) polyoxyethylenesorbitan monolaurate and 0.006% (v/v) β-mercaptoethanol. Control tissue (non-transformed) samples were prepared in a similar manner. Samples were spun in a microfuge for 1 min. before loading into wells of the prepared microtitre plates. Sample supernatant was loaded (100 µl/well) in replicates (3 or 4). Plates containing samples are incubated for 2–3 hrs. at room temperature. For quantitation, standards of *B. thuringiensis* crystal protein can be included.

After incubation the contents of the wells were removed and the plate was rinsed carefully with wash buffer (4–5 times). The plate was filled with wash buffer and agitated for 5 min. Care should be taken in this step to avoid cross-contamination of samples, controls and standards.

A 1:2000 dilution of the primary antibody in antibody buffer was then loaded into the wells (100 μl/well). Plates were covered and stored at 4° C. overnight (about 12 hours). Antibody buffer contained PBS (pH 7.4) with 1% (v/v) goat serum and 0.05% polyoxyethylenesorbitan monolaurate. Plates were then washed (3–4 times) with wash buffer (as above). Plates were then blotted dry.

A 1:2500 dilution of labelled secondary antibody (goat anti-rabbit IgG (H+L)-alkalinephosphatase-labelled) was then loaded into wells (100 μl/well). Plates were incubated for 1–2 hours at room temperature and thoroughly washed. Plates were washed 4–5 times with wash buffer. Plates were filled with wash buffer and placed on a shaker for at least 10 minutes. Plates were rinsed again and blotted dry.

An NADH substrate was then employed to detect bound labelled antibody. NADP (β-Nicotinamide Adenine Dinucleotide Phosphate) 0.25 mg/ml in 0.50 mM $MgCl_2$) 0.05 mM diethanolamine (pH 9.5) was loaded into the assay wells (100 μl/well). Plates were covered and stored at 4° C. for about 1½ hours.

Reagent solution was prepared by dissolving p-iodonitrotetrazolium violet (0.31 mg/ml) in 0.05 M sodium phosphate buffer (pH 7.2) containing 1.9% (v/v) ethanol. To this solution diaphorase "NADH/dye oxidoreductase" (Boehringer Mannheim, Mannheim, West Germany) to 0.035 mg/ml and alcohol dehydrogenase (baker's yeast) to 0.035 mg/ml were added. The reagent solution was incubated at 4° C. for 45 minutes after which it was added to the NADP solution in each assay well (150 μl/well).

The color reaction (red) began immediately. Optical density measurements were read at 492 nm.

Adjusted ELISA values of crystal protein in leaf tissue, expressed as absorbance at 492 nm, are reported in Table 7. The values were adjusted by subtracting from each measurement the value obtained for a Nicotiana tabacum var. "Xanthi" control. Many plants were observed to contain measurable amounts of antigen which bound anti-crystal protein antibody.

12.9 Expression in Plant Tissues: Bioassays

Tobacco tissue transformed by pH450 was cloned and maintained in a growth chamber. For bioassay, leaves were cut off with a razor blade and placed in a 9 cm petri dish lined with moist filter paper. Newly hatched tobacco hornworm larvae (*Manduca sexta*) were put on the leaves. Mortality was recorded.

In trial 1, three clones from each type were sampled with five larvae per dish (Table 8). The data can be summarized as follows:

| Clone | Total | Dead | % Dead |
|---|---|---|---|
| 100 | 14 | 5 | 36 |
| 103 | 15 | 1 | 7 |
| 106 | 15 | 0 | 0 |
| 109 | 15 | 5 | 33 |
| 111 | 15 | 3 | 20 |

Trial 2 was essentially done as described for trial 1, but here two larvae were placed in each dish. The data are reported in Table 9 and can be summarized as follows:

| Clone | Total | Dead | % Dead |
|---|---|---|---|
| 100 | 14 | 9 | 64 |
| 103 | 18 | 4 | 22 |
| 106 | 24 | 12 | 50 |
| 109 | 26 | 7 | 27 |
| 111 | 18 | 8 | 44 |

Leaves that had killed both larvae by day 2 were then reinfested with three newly hatched larvae. While the numbers were not large enough to make comparisons between treatments, it was clear that these leaves are still toxic. For example, three dishes from clone 100 received a total of 9 larvae, 6 of which were dead 2 days later.

As protein concentration is highest in small leaves, expression might vary with the size of the leaf, i.e., with the degree of expansion of the cells. Therefore in trial 3 leaves were measured before bioassay. For this test, only plants that had not been sampled before of clones 100 and 103 were sampled. The data were ranked from smallest to largest leaves, (1 for smallest and 10 for largest) but the sizes for the two clones were not aligned. Different numbers of dishes were set up for each plant because the plant of clone 100 had fewer leaves. Three larvae were placed in each dish. Number of dead larvae per dish are reported below.

| Rank | Clone 100 | Clone 103 |
|------|-----------|-----------|
| 1    | 1         | 0         |
| 2    | 3         | 0         |
| 3    | 1         | 0         |
| 4    | 1         | 0         |
| 5    | 1         | 0         |
| 6    | 3         | 0         |
| 7    | 3         | 0         |
| 8    |           | 0         |
| 9    |           | 2         |
| 10   |           | 1         |

It is clear that both small and large leaves are able to kill the larvae. Furthermore, the difference between different plant clones, i.e., 100 and 103, is apparent: 62% vs. 10% mortality, at day 2.

In trial 4, randomly assigned labels were used to avoid biases. Five petri dishes from each clone were prepared with three larvae per dish. In addition, a Xanthi plant that originated in tissue culture was used as a control. The data can be summarized as follows:

| Summary | Dead/Total | % Mortality |
|---------|-----------|-------------|
| control | 2/15      | 13          |
| 100     | 11/15     | 73          |
| 103     | 8/15      | 53          |
| 106     | 2/15      | 13          |
| 109     | 1/15      | 7           |
| 111     | 3/15      | 20          |

Clone 100 gave consistently high mortality. Clone 103 also gave high mortality explained by the subsequently discovered fact that "clone" 103 was not in fact a clone; the original transformed plant has now been shown to have been a chimeric plant. It has not proven to be particularly insecticidal in any other of the five trials.

After the trial 4 leaves had been fed on for two days, ELISAs were performed on some of the lethal and nonlethal leaves. No crystal protein antigen was detected because of the low levels of protein in these leaves.

In trial 5, four plants were propagated from clone 100 and five from clone 103. Five leaves were sampled from each of these plants. Each leaf was placed in an individual petri dish with three newly hatched larvae. The data can be summarized as follows:

| Summary | Dead/Total | % Mortality |
|---------|-----------|-------------|
| 100     | 8/14      | 57          |
| 100     | 3/14      | 21          |
| 100     | 10/15     | 67          |
| 100     | 5/14      | 36          |
| 103     | 3/15      | 20          |
| 103     | 1/15      | 7           |
| 103     | 2/15      | 13          |
| 103     | 2/15      | 13          |

Thus, clone 100 is consistently more toxic than clone 103.

Southern blot analysis of DNA isolated from presumptive transformants showed that cloned plant tissue having insecticidal activity in bioassays and containing crystal protein antigen generally had pH450's T-DNA. Northern blot analysis of RNA generally demonstrated the presence of mRNA having crystal protein sequences. These mRNA molecules were not the expected size of about 3.8 kbp, but were about 1.7 kbp in size. This was sufficient to encode the toxic portion of the crystal protein. As predicted from the fact that crystal protein levels in leaves as estimated by ELISA were below the limit of detection on western blots, western blot analysis of proteins extracted from transformed tissues did not reveal any antigens that cross-reacted with anti-crystal protein antibodies. Polypeptides that bind anti-crystal protein antibodies have been detected by western blot analysis of both transformed callus and young shoot tissues.

Example 13

This Example teaches more DNA constructions useful for transformation of a number of species of plants.

13.1 Plant Transformation Vectors pH450 was described in Example 12.6. pH575 was disclosed by Sutton et al. (1987) European Patent Publication 0 223 417 (priority document: U.S. patent application Ser. No. 788,984, filed Oct. 21, 1985, which is hereby incorporated by reference). pH576, pH577, pH578, pH582, and pH585 are derivative of pH575, having various promoter/insecticide structural gene/polyadenylation site combinations, all oriented parallel to the ocs gene and the plant-selectable kan gene and inserted into the BglII site of pH575 between those two genes.

13.2 Modification of an Insecticide Gene's 5'-end

Construction, isolation, and characterization of pNSBP544 was disclosed by Sekar et al. (1987) Proc. Natl. Acad. Sci. USA 84:7036:7040; and Sekar and Adang, U.S. patent application Ser. No. 108,285, which is hereby incorporated by reference. A 3.0 kbp HindIII fragment carrying the crystal protein gene of pNSBP544 was inserted into the HindIII site of pIC-20H (Marsh et al. (1984) Gene 32:481–485), thereby yielding a plasmid designated p544-HindIII, which is on deposit. 73 kDa crystal protein may be expressed in E. coli. The 73 kDa species is processed to form the 65 kDa species by removal of 49 amino acids at the amino-terminus of the 73 kDa species, leaving alanine at the amino-terminus of the 65 kDa species.

A 5.9 kbp BamHI fragment carrying the crystal protein gene was removed from pNSBP544 and inserted into BamHI-linearized pIC-20H DNA. The resulting plasmid, p405/44-7, was digested with BglII and religated, thereby removing Bacillus sequences flanking the 3'-end of the crystal protein gene. The resulting plasmid, p405/54-12, was digested with PstI and religated, thereby removing Bacillus sequences flanking the 5'-end of the crystal protein and about 150 bp from the 5'-end of the crystal protein structural gene. The resulting plasmid, p405/81-4, was digested with SphI and PstI and was mixed with and ligated to a synthetic linker having the following structure:

```
           SD        MetThrAla
    5'CAGGATCCAACAATGACTGCA3'
    3'GTACGTCCTAGGTTGTTACTG5'
     SphI                 PstI
```

(SD indicates the location of a Shine-Dalgarno prokaryotic ribosome binding site.) The resulting plasmid, p544Pst-Met5, contains a structural gene encoding a protein identical to one encoded by pNSBP544 except for a deletion of the amino-terminal 47 amino acid residues. The protein encoded by p544Pst-Met5 is 2 amino acids longer than the 65 kDa toxic polypeptide processed from the 75 kDa crystal protein encoded by pNSBG544 (data not shown; see also McPherson et al. (1988) Biotechnol. 6:61–66). In bioassays, the proteins encoded by pNSBP544 and p544Pst-Met5 were shown to be equally toxic. All of the plasmids mentioned above have their crystal protein genes in the same orientation as the lacZ gene of the vector.

13.3 Modification of an Insecticide Gene's 3'-end

A HindIII site and a XmaI site were removed from the kanamycin resistance gene (kan), which encodes neomycin phosphotransferase I (NPT1), of pUC4K (Vieira and Messing (1982) Gene 19:259–268) by the method of Merlo and Thompson (1987) Anal. Biochem. 163:79–87. The kan gene was removed from the resulting plasmid on a HincII fragment, and the ends were filled in by T4 DNA polymerase to make sure that they were blunt. pIC-20R (Marsh et al., (1984) supra) DNA was digested with NdeI and ScaI and the ends were filled in by T4 polymerase. The resulting DNA, lacking the 5'-end of the ampicillin-resistance gene (amp) was mixed with and ligated to the NPT1-encoding HincII fragment. A plasmid having kan in the same orientation as amp was identified and labeled pIC-20RXmn⁻Kan$^r$.

A HindIII fragment carrying the crystal protein gene was removed form p544Pst-Met5 and inserted into the HindIII site of pIC-20RXmn⁻Kan$^r$. A plasmid having the crystal protein gene oriented antiparallel to the pIC-20R lacZ gene was identified and designated p461/80-159. p461/80-159 DNA was digested with BglII and XmnI which opened it at the BglII site of the pIC-20R polylinker and just after nucleotide 1778 (XmnI) of the crystal protein gene. The opened plasmid was mixed with and ligated to a synthetic DNA linker having the following structure:

```
          PheIleProValAsnLeuArgSer
       5'TATCCCAGTGAATTTAA3'
       3'ATAGGGTCACTTAAATTCTAG5'
                              BglII
```

(The underlined base pair indicates a mutation that eliminates the XmnI site present in the wild-type gene.) The resulting plasmid was designated p461/97-14.

13.4 Fusion of an Insecticide Gene with NPT2 Sequences

The kan gene of TN5 was modified as follows (see Merlo et al. European Patent Application Publication No. 0 233 417, priority U.S. patent application Ser. No. 788,984, continued by Ser. No. 144,016). Coordinates refer to the sequence published by Beck et al. (1982) Gene 19:327–336. The G at position 144 was changed to a C, thereby introducing a BamHI site. The C at position 148 was changed to an A, thereby improving the efficiency of eukaryotic translational initiation at the AUG at position 151 to 153. THe SmaI site that cuts after position 1118 was changed to a BglII site by digestion with SmaI followed by ligation to BglII linkers. The NPT2 gene is carried by a 0.98 kbp DNA fragment after digestion with BamHI and BglII.

The 0.98 kbp fragment was mixed with and ligated to BglII-digested p461-97-14 DNA (Example 13.3). A plasmid, p461/151–174, was identified having the NPT2 sequence oriented with its 5'-end BamHI site fused with the BglII site proximal to the truncated Btt crystal protein gene of p461/97–14. The suture of p461/151–174 between the Tn5 and *B. thuringiensis* sequences was sequenced to confirm conservation of reading frame.

13.5 Construction of Transcription Vectors

An 833 base pair (bp) fragment was cut out of the pUC13 clone carrying the "−343" deletion (Odell et al. (1985) Nature 313:810–812) by digestion with SmaI and HindIII. This fragment carries a functional 35S promoter and the 5'-end of the CaMV 35S transcript, spanning from position −343 to position +9 relative to the transcriptional start site. This fragment was ligated into pIC19R (Marsh et al. (1984) Gene 32:481–485) which had been digested with NruI and HindIII. The ORF25 polyadenylation site was contributed by a pTi15955 fragment spanning HincII sites at positions 21,727 and 22,440, as disclosed by Barker et al. (1983) Plant Mol. Biol. 2:335–350, ligated into the SmaI site of pIC19H (Marsh et al., (1984) supra), the ORG25 polyadenylation site being proximal to the BamHI site in the pIC19H polylinker. The T-DNA was then removed from the pIC19H vector on a BamHI/ BglII fragment which was then inserted into the BamHI site of the pIC19R/35S promoter combination, the T-DNA being oriented so that the ORF25 polyadenylation site was proximal to the 35S promoter, a functional BamHI site was between the CaMV and T-DNA sequences, and a BamHI/BglII fusion was between the T-DNA and pIC19R sequences. This plasmid was then opened at the SmaI site between the fused BamHI/BglII site and the pIC19R vector sequences. Plural BglII linkers were ligated into the SmaI site, resulting in formation of a PstI site between the linkers. The resulting plasmid was designated pIC35/A.

A DNA linker encoding the tobacco mosaic virus (TMV) 5'-leader sequence was synthesized. The linker had the structure of

```
  (BglII)                           Tth111II
5' GATCTATTTTTACAACAATTACCAACAACAACAAACAA...
3'      ATAAAAATGTTGTTAATGGTTGTTGTTGTTTGTT...
                                                  (BamHI)
              ...CAAAACAACATTACAATTACTATTTACAATTACG      3'
              ...GTTTTGTTGTAATGTTAATGATAAATGTTAATGCCTAG 5',
``` the horizontal lines indicating the location of sites recognized or partially recognized (partial recognition is indicated by parentheses) by the indicated restriction enzymes. This linker was inserted into pIC35/A's BamHI site. The resulting plasmid, designated pIC35/A-TL 4, had a BamHI site between the TMV leader and the ORF25 polyadenylation site.

An NPT2 expression vector was constructed having the same CaMV DNA fragment carrying the 35S promoter as pIC35, the same NPT2 structural gene as used in Example 14.2.2 to construct p461/151–174, and the same T-DNA ORF25 polyadenylation site as used in pIC35/A. A 3.0 kbp HindIII fragment carrying the truncated Btt crystal protein gene of pNSBP544 was inserted into pIC19R-Kan or p35S-Kan.

13.6 Assembly of Direct Transformation Vectors

The insecticide structural gene/fusion linker combination of p461/97–14 was removed by digestion with BglII and BamHI and inserted into BamHI-linearized pIC35/A-TL4 DNA. A plasmid, designated p461:151–193, was identified which had the insecticide structural gene oriented so that the 5'-end of the insecticide structural gene was proximal to the 35× promoter and the 3'-end of the linker was proximal to the ORF25 polyadenylation site.

The insecticide structural gene/fusion linker/NPT2 structural gene combination of p461/151–174 was removed by digestion with BglII and BamHI and inserted into BamHI-linearized pIC35/A-TL4 DNA. A plasmid, designated p461:162–191, was identified which had the insecticide structural gene oriented so that the 5'-end of the insecticide structural gene was proximal to the 35S promoter and the 3'-end of the NPT2 structural gene was proximal to the ORF25 polyadenylation site.

13.7 Fusion of an Insecticide Gene with Hygromycin Sequences

An insecticide structural gene was derived from a 5.3-class gene (Kronstad and Whiteley (1986) Gene 43:29–40) from *B. thuringiensis* HD-1 (pBT1-106A, disclosed by Adang et al. (1987) in *Biotechnology in Invertebrate Pathology and Cell Culture* (K. Maramorosch, ed.), pp. 85–99). The 3'-end of this gene was removed by digestion with Bal31 and a linker having the structure

```
5' TAATTGAATAGATCT 3'
   3' ATTAACTTATCTAGA
``` was ligated onto the end. This linker encoded stop codons in all three reading frames and a BglII site at its 3'-end. The resulting structural gene had 1820 bp from the 5'-end of the structural gene, encoding 607 amino acids and an extra asparagine residue, encoded by the linker at the carboxy terminus. The 3'-end of the structural gene, therefore, had the structure

```
     IleAspArgIleGluPheValProAlaAsnEnd BglII
5' ...ATAGATCGAATTGAATTTGTTCCGGC
TAATTGAATAGATCT...3'
``` where the underlined sequence at the left indicates the sequence which in other experiments was shown to be insufficient to be insecticidal.

A hygromycin gene (hyg) (Gritz and Davies (1983) Gene 25:179–188) was modified by a G residue at position −3 relative to the translation start codon, and by insertion of a BamHI site 5' to the translational start codon, 8 bp separating the BamHI site and the start codon. Having a G at −3 is thought to enhance translational initiation in eukaryotes. This hyg gene was ligated to the BglII site of the truncated Dipel gene, thereby forming a DNA sequence which can encode a dicistronic mRNA. The polypeptide encoded by the truncated Dipel gene was shown to be as toxic as the protein encoded by the full-length Dipel gene.

13.8 Description of Binary Vectors pH576 was a pH575 derivative carrying an ORF24 promoter/insecticide structural gene/ORF24 polyadenylation site combination identical to that carried by pH450.

pH577 was a pH575 derivative carrying a CaMV19S promoter/insecticide structural gene/CaMV polyadenylation site combination, the promoter and polyadenylation being carried by the same fragments which contributed them to the plant-selectable kan genes of pH450 and pH575. pH577 had the same *Bacillus thuringiensis* HD-73 insecticide structural gene as pH450.

pH578 was a pH575 derivative carrying a CaMV 35S promoter/insecticide structural gene/T-DNA ORF25 polyadenylation site combination. pH578 had the same *Bacillus thuringiensis* HD-73 insecticide structural gene as pH450 and the same promoter and polyadenylation site as carried by pIC35/A.

pH582 was a pH575 derivative carrying a CaMV 35S promoter/insecticide structural gene/T-DNA ORF25 polyadenylation site combination. The promoter and polyadenylation site were the same as used in pH578. The insecticide structural gene was derived from a 5.3-class gene (Kronstad and Whiteley (1986) Gene 43:29–40) from *B. thuringiensis* HD-1 and included about the 1.83 kbp 5' from the structural gene (pBT1-106A, disclosed by Adang et al. (1987) in *Biotechnology in Invertebrate Pathology and Cell Culture*, K. Maramorosch, ed., pp. 85–99). The portion utilized encodes essentially only the toxic region of the insecticidal protein.

pH585 was a pH575 derivative carrying an ORF24 promoter/insecticide structural gene/ORF24 polyadenylation site combination, the insecticide structural gene being the same as contained by pH582. The promoter and polyadenylation site was the same as used in pH450 and pH576.

pH591 was a pH575 derivative carrying an ORF24 promoter dicistronic gene/ORF24 polyadenylation site. The dicistronic gene was the truncated Dipel structural gene/hyg structural gene combination described in Example 13.7.

pH610 was a binary vector based on a pTJS75 replicon (Klee et al. (1985) Biotechnol. 3:637–642), previously used herein to make pH450 and pH575. The tetracycline resistance gene (tet) of pTJS75 had been replaced with an erythromycin resistance gene (ery) derived from pR29 (Morrison et al. (1984) J. Bacteriol. 159:870–876). From "left" to "right", the T-DNA of pH610 consisted of a pTi15955 (numbering scheme as in Barker et al. (1983) Plant Mol. Biol. 2:335–350) fragment spanning positions 602 to 1186 and carrying the left $T_L$-DNA border repeat; a neomycin phosphotransferase I (NPT1) gene, expressed in bacteria, originally from Tn903 (excised on a 1.45 kbp BamHI fragment from pUC4K, Vieira and Messing (1982) Gene 19:259–268), oriented to transcribe from left to right; a plant-expressible hygromycin-resistance gene, transcribed from right to left, under control of the CaMV 35S promoter and the T-DNA ORF25 polyadenylation site from pIC35/A, the hygromycin resistance structural gene being derived from pLG62 (Gritz and Davies (1983) Gene 25:179–188); a dicistronic plant-expressible gene transcribed from right to left under control of the ORF24 promoter and either the ORF25 or ORF26 polyadenylation site (Barker et al., (1983) supra), the dicistronic gene having an insecticide structural gene from HD-1 (Dipel) (a 4.5 kb-class gene (Kronstad and Whiteley (1986) Gene 43:29–40)) at its 5'-end and a NPT2 structural gene (kan) at its 3' end; and a T-DNA fragment spanning positions 12,070 to 14,710, carrying an octopine synthase gene (ocs) transcribed to the left and the right $T_L$-DNA border repeat.

pH615 was identical to pH610 with some exceptions. There was no NPT1 gene. In the plant-expressible selectable marker, a TN5 NPT2 structural gene (the "double mutant" of Sutton et al., European Patent Publication No. 0 223 417) and an ORF26 polyadenylation site (from the same HincII fragment as contributed the ORF25 site) substituted from the hygromycin resistance structural gene and the ORF25 polyadenylation site of pH610. The plant-expressible insecticide gene was terminated by an ORF25 polyadenylation site. The insecticide structural gene was from HD-1 (Dipel) (a 4.5 kbp-class gene (Kronstad and Whiteley, (1986) supra) ), and was preceded by a slightly modified alfalfa mosaic virus (AMV) $RNA_4$ 5'-leader sequence. This leader was encoded by a synthetic linker having a structure of

```
(HindIII)                              HpaI        (NcoI)
5' AGCTTGTTTTTATTTTTAATTTTCTTTCAGTTAACTTCCAC    3'
3'    ACAAAAATAAAAATTAAAAGAAAGTCAATTGAAGGTGGTAC 5'
``` the horizontal lines indicating the location of sites recognized or partially recognized (partial recognition is indicated by parentheses) by the indicated restriction enzymes. This linker could be ligated to the HindIII site ate the 3' end of the 35S promoter, the resulting transcripts having 9 bp of the CaMB 35S transcript as its 5' end. The NcoI sticky-end could be ligated to the 5' end of a structural gene by use of appropriately-tailed linkers.

pH619 was essentially identical to pH615 excect for the insecticide structural gene and the polyadenylation site 3' therefrom. The insecticide structural gene of pH615 was the same as that carried by p544Pst-Met5, but lacking almost totally Bacillus sequences 3' from the translational stop codon. The polyadenylation site 3' from the structural gene was from T-DNA ORF25 and was carried, as described elsewhere herein, on a HincII fragment. Additionally, a TMV 5'-leader sequence (Example 13.5) was present between the 35S promoter and the p544Pst-met5 structural gene.

pH623 was essentially identical to pH610 except for the presence of the TMV5'-leader (Example 13.5) at the 5'-end of the structural gene and for the substitution of the insecticide structural gene carried by p461/97–14 for the insecticide structural gene of pH610. The 3'-extension of the coding sequence beyond the natural position of the translational termination site did not affect toxicity of the encoded insecticidal protein.

pH624 was essentially identical to pH619 except for substitution of the insecticide/NPT2 structural gene of p461/151–174 for the insecticide structural gene of pH619.

pH627 was identical to pH615 with the exception of the presence of an inserted phaseolin third intron in the AMV $RNA_4$ 5'-leader sequence. A fragment of a phaseolin gene, carrying the third intron and flanking coding sequences, and spanning from the XbaI site at position 904 to the Sau3AI site at position 1061 (as numbered by Slightom et al., supra). This fragment could be inserted into the HpaI site of the AMV $RNA_4$ leader linker with the aid of appropriate linkers to adapt XbaI and Sau3A sticky ends to the blunt ends of HpaI.

13.9 Deposited Strains

The following strains were deposited with the Patent Culture Collection, Northern Regional Research Center, 1815 N. University Street, Peoria, Ill. 61604:

| Strain | Deposit Date | Accession # |
|---|---|---|
| E. coli MC1061 (p544-HindIII) | 10/06/87 | NRRL B-18257 |
| E. coli MC1061 (p544Pst-Met5) | 10/06/87 | NRRL B-18258 |

The deposited strains are provided for the convenience of those in the art, and are not necessary to practice the present invention, which may be practiced with the present disclosure in combination with publicly available protocols, information and materials. E. coli MC1061, a good host for plasmid transformations, was disclosed by Casadaban and Cohen (1980) J. Mol. Biol. 138:179–207.

Example 14

This Example teaches expression in Zea mays of a coleopteran-active insecticidal protein gene from Bacillus thuringiensis var. tenebrionis.

14.1 Maize Protoplast Transformation

A suspension culture of Black Mexican Sweet (BMS) corn cells was digested in 2% cellulase, 0.25% pectinase (both from Worthington Biochemical Corp., Freehold, N.J.), 0.2 M mannitol, and 80 mM $CaCl_2$ for about 4 hr at a concentration of about 1 g fr. wt. cells in 10 ml enzyme solution. The protoplast solution was filtered through a 46μ mesh sieve to remove undigested cell clumps. Protoplasts were obtained from 8.5 g fr. wt. of cells. After washing, the protoplasts were resuspended in MaMg (0.4 M mannitol, 15 mM $MgCl_2$, 0.1% MES, pH 5.6) at a concentration of $2.5 \times 10^6$ ml$^-$. Half ml aliquots of protoplasts were placed into 15 ml disposable round-bottom centrifuge tubes. Appropriate DNA solutions were added to each tube, followed by the addition of 300 μl of a 40% (w/v) polyethylene glycol (PEG) solution (ave. PEG molecular weight=6000–7500; source: EM Science, Gibbstown, N.J.; dissolved in NaMg; final pH about 6.0; filter-sterilized). DNA solutions were as follows:

|  | BTT | Fusion-High | Fusion-Low | Control |
|---|---|---|---|---|
| μg p461:162–191 DNA | — | 10 | 2.5 | — |
| μg p461:151–193 DNA | 25 | — | — | — |
| μg pIC19R-35S-Kan DNA | 2.5 | — | — | — |
| μg salmon sperm carrier DNA | 22.5 | 40 | 47.5 | 50 |
| Total DNA conc. (μg/ml) | 100 | 100 | 100 | 100 |

[1] See Section 13–6, page 132 for a description of the plasmid construction.

The tubes were incubated for 30 min at room temperature with occasional gentle mixing. The incubations were then diluted by addition of and mixing with 1 ml of MS4D+8M (MS salts, 4 mg/l 2,4-D, 8% mannitol, 2% sucrose, 0.75 mg/l thiamine.HCl, 7.7 mg/l glycine, 1.3 mg/l nicotinic acid, 0.25 mg/l pyridoxine.HCl, 0.25 mg/l calcium pantothenate, and 1 mM asparagine). After a further 5 min, two further dilutions of 2 ml MS4D+8M were done at 5 min intervals. The protoplasts were centrifuged at low speed, resuspended at a concentration of $2 \times 10^5$ m$^{-1}$ in CM+8% mannitol (CM=conditioned medium=filter-sterilized medium that BMS suspension cells had been growing in), poured into a 100×20 mm Petri plate, diluted with an equal volume of MS4D+8M, 2.4% SP (Sea Plaque agarose (FMC BioProducts, Rockland Me.) at about 37° C., and swirled to evenly disperse protoplasts. After the medium had solidified, the Petri plates were sealed with parafilm, placed in plastic storage boxes and incubated in very dim light at about 26° C.

After 12 days, 12.5 ml of MS4D+4% mannitol+100 mg/l kanamycin was added to the plates, resulting in a final selective kanamycin concentration of about 50 mg/l. Nine days later, agarose slabs containing developing protoplast-derived colonies were replated onto Gel-rite-solidified MS4D+100 mg/l kanamycin in 100×15 mm Petri plates. Kanamycin-resistant calli developed within 3 weeks from cell treatments except the "Control." The kanamycin-resistant calli were transferred individually to fresh Gel-rite-solidified MS4D+100 mg/l kanamycin, and were subsequently maintained by transferring every 2 to 3 weeks onto medium of the same composition.

After selection on kanamycin, no "Control" calli remained, and 3 "Fusion-Low" calli, 7 "Fusion-High" calli, and 169 "BTT" calli had survived.

14.2 Assay of Insecticidal Protein

Presence of the introduced DNA sequences was analyzed by Southern blot hybridization, using nick-translated NPT2 and insecticide gene DNA fragments (IG) as probes. Expression of the introduced genes was assayed by ELISA, using anti-NPT2 and anti-*B. thuringiensis* var. *tenebrionis* crystal protein antisera (CP). Separate tissue samples from each cell line were used for each assay. The results of the ELISA assays and Southern blots on the "Fusion" calli are summarized in Table 10.

ELISA positive were obtained only from calli whose DNA had regions of homology to both the NPT2 and IG probes. The lack of complete correspondence between the NPT2 and CP ELISAs could be due to reasons such as differential sensitivity of the assays, occasional problems with protein extraction or protein stability, or chimeric cell lines.

Twenty-eight of the 169 "BTT" calli were assayed by ELISA on two different days (separate tissue samples), using the anti-insecticidal protein antiserum. The results are shown in Table 11. Nine out of 28 (32%) of the calli tested positive in at least one of the two assays. There were only three discrepancies between the two assays (calli 6–21, 6–32 and 21-12). In each case, the callus tested positive in Experiment 1 and negative in Experiment 2. The most likely explanation is lower sensitivity of the Experiment 1 assay compared to the Experiment 2 assay.

Example 15

This Example teaches the expression in tomato (*Lycopersicum esculentum*) of the full-length *Bacillus thuringiensis* insecticide gene under control of both viral and T-DNA promoters.

15.1 Leaf Tissue Transformation

The leaf tissue transformation protocol combined and modified the procedures of Bevan, M. et al. (1985) EMBO J. 4:1921–1926, and Horsch, R. F. et al. (1985) Science 227:1229–1231. Leaves from three- to five-week-old greenhouse-grown seedlings were used. These leaves were washed, surface-sterilized, brushed, cut into 5 mm sections, and placed on agar-solidified regeneration medium (MS salts (Murashige, T. and Skoog, F. (1962) Physiol. Plant. 15:473–497), 30 g/l sucrose, 100 mg/l thiamine, 50 mg/l nicotinic acid, 50 mg/l pyridoxine, 5 $\mu$M zeatin riboside, 3 $\mu$M 3-indole-acetyl-DL-aspartic acid, 9 g/l agar, pH5.65–5.8) or moistened filter paper for 1 day before bacterial inoculation. It was important to keep leaves moist. There were noticeable increases in survival with the 24-hour culture period prior to bacterial inoculation. Overnight cultures of bacteria were grown in L broth on selective antibiotics and diluted about 1/10 (an OD at 595 nm of about 0.250) prior to use. Bacteria were applied to each leaf disc with a sterile paint brush and then plates were placed at 25° C. for 2–3 days. After the 2 days, leaf discs were rinsed in antibiotic-containing regeneration media, and then placed on antibiotic-containing regeneration agar plates. (All plates had an antibiotic-containing medium, containing 50 mg/l cefotoxin, or 250 mg/l carbenicillin and 50 mg/l vancomycin).

Leaves transformed by bacterial strains containing the kanamycin resistance genes were grown under selection pressure using three procedures (Colbere-Garapin, F. et al. (1981) J. Mol. Biol. 15:1–14): (1) placement of inoculated explant on antibiotic-containing medium with 20 mg/l G418; (2) placement of explants on antibiotic medium with 5 mg/l G418; and (3) placement of explants on antibiotic medium with no G418. All treatments were transferred to plates containing about 15 to 20 mg/l G418 after approximately 5–7 days. An additional transfer two weeks later helped to eliminate further escapes. Tissues were then tested for opines.

15.2 Hypocotyl Transformation

The use of inverted stem segments for in vitro transformation of tobacco tissues was first developed by Braun, A. C. (1956) Cancer Res. 16:53–56. The key to success using this method appears to be the fact that wound cell divisions and callus formation occur at the basal end of the stem or hypocotyl segment. These divisions are important for two reasons. First, wound responses are known requirement for transformation by *Agrobacterium tumefaciens*. Second, and more important, is that the subsequent cell divisions increase the numbers of transformed cells to a point where they can be screened for by opine analysis and survive heavy kanamycin selection pressure. The standard protocol used was to isolate hypocotyl segments (from sterile plants grown in growth incubator), to invert these so that the basal end was up, and then to inoculate with 2 $\mu$l bacteria applied with a micropipet (Pipetman). Bacteria were grown in L broth of MSSP medium supplemented with 50 AM acetosyrigone (Stachel, S. E. et al. (1985) Nature 318:624–629). After 1 to 2 days, the segment was washed thoroughly with liquid medium containing antibiotic and transferred to solidified antibiotic-containing medium. After visible callus was observed, it was excised, and cut into small pieces (about 3 mm) and subcultured on agar-solidified medium containing antibiotics. (These antibiotics included carbenicillin 260 mg/l and vancomycin 50 mg/l and G418 for selection pressure.) After tissues were grown to a large enough size (about 50 to 100 mg), they were subcultured and analyzed for opine content.

15.3 Transformations with Agrobacterium Strains

Strains used for transformation of tomato were *A. tumefaciens* LBA4404 (Ooms, G. et al. (1981) Gene 14:33–50) containing the binary vectors pH450, pH575, pH576, pH578, pH582, and pH585. Transformations were made as described above on both leaf and hypocotyl tissues of UC82, LA14, V7 (LA14×LA159) and V7R (LA159×LA14) hybrids (carrying several marked genes in a heterozygous state and proprietary hybrids 6–16, 6t0016, and 6t60045 M. Hypocotyl transformations generally yielded higher efficiency of transformation as detected by octopine production and kanamycin resistance. Efficiency of leaf transformations varied in the range of about 0.5% to about 5.0% depending on the particular Agrobacterium strains while hypocotyl transformations ranged in efficiency from about 5 to about 40% (Table 12).

Tomato plants were regenerated as described by Tatchell, S. and Bins, A. (1986) Tomato Genet. Coop. Rept. No. 36, pp. 35–36.

15.4 ELISAs

ELISA protocols were based on those described in Example 12.8. Techniques for preparing tissue samples were modified to enhance detection of insecticidal protein in plant tissues. Since in plant extracts, solubilization can be incomplete, this centrifugation step was eliminated. Leaf tissue was harvested from greenhouse plants, weighed and placed in Eppendorf tubes on ice. Samples were quickly frozen in liquid nitrogen, thawed briefly, ground with a glass rod, and resuspended in 5× W/V PBS with 0.1 mM phenylmethysulfonyl flouride (PMSF). These samples are placed in the cold for about twenty minutes before taking aliquots for protein assays. Modified double antibody sandwich ELISAs with NADP-enhanced alkaline phosphatase were performed on tissue extracts containing 0.02 to 0.5 mg/ml protein (Clark, M. F. and Bar-Joseph, M. (1984) Meth. Virol. 7:51–85). Polystyrene microtiter plates were coated with mouse polyclonal antisera in 15 mM sodium carbonate buffer, 35 mM sodium bicarbonate, and pH9.6 (0.1 ml/well)

and stored at 4° C. for 1 day to 2 weeks. Between each step, plates were washed 3 times with PBS-Tween (PBS+0.05% Tween). Plates were blocked with blocking solution (PBS-Tween+1% bovine serum albumin (BSA) fraction V (Sigma) and 1% casein acid hydrolysate (Sigma)). Plates were washed again and 0.1 ml/well antigen solution was added and incubated for about 2 to 3 hr at 25° C. Primary rabbit antisera against *B. thuringiensis* insecticidal protein were added to washed plates and incubated overnight at 4° C. The following morning, plates were washed and a 1:2500 dilution of alkaline phosphatase-labelled goat anti-rabbit ahtibody (Kirkegaard Perry Laboratories, Inc.) was added for about 2 hr. Plates were developed with modified nicotinamide adenine dinucleotide phosphate (NADP) enhancement (Johansson, A. et al. (1986) J. Immun. Meth. 87:7–11; Stanley, C. J. et al. (1985) J. Immun. Meth. 83:89–95; Self, C. H. (1985) J. Immun. Meth. 76:389–393). This involved addition of 0.1 ml/well of 300 mM NADP in diethanolamine substrate buffer (50 mM diethanolamine HCl pH9.5, 1 mM $MgCl_2$) followed 25 min later by addition of amplifier buffer (0.05 M sodium phosphate buffer, pH7.2, containing 5 mg/ml BSA and 4% ethanol) with 0.55 mM p-iodonitrotetrazolium (Sigma), 1.5 mg/ml Diaphorase (Boehringer Mannheim), and 2 mg/ml alcohol dehydrogenase (Sigma). The reaction was stopped by the addition of 0.2 M $H_2SO_4$. Absorbances were read at 492 nm. Alternate development used was conventional p-nitrophenyl-phosphate development.

15.5 Western Blots

*Bacillus thuringiensis* insecticidal protein was detected in transformed tomato plants using protein immunoblot procedures ("westerns"). The basic protocol involved preparation of leaf tissue by freezing in liquid nitrogen, grinding with mortar and pestle and precipitating protein with 10% trichloroacetic acid. The samples were incubated on ice for at least 30 min. and then spun at approximately 9000 rpm for 10 minutes. The pellet was resuspended in phosphate-buffered saline (PBS: 10 mM sodium phosphate, 0.15 M NaCl, pH7.4) and then insecticidal protein was precipitated in 20% ammonium sulfate, saturated ammonium sulfate being added slowly to samples at 4° C. Samples were then spun for 10 min. at 9000 rpm, pellets were resuspended in modified PBS (PBS, 1% polyvinyl pyrrolidone, 0.006% 2-mercaptoethanol (2ME), 0.01% phenylmethylsulfonyl fluoride) and then dialyzed in PBS overnight at 4° C. Samples were cleared through glass wool and frozen at −20° C. in cracking buffer (5% SDS, 6 M urea, 20 mM $NaH_2PO_4$, 0.02% bromophenol blue, 20% glycerol, and 0.3% 2ME). Tissue samples were then loaded on 8.5% acrylamide running gels (1 mm) with a 4.5% acrylamide stacking gel (Laemmli, U.K. (1970) Nature 227:680–685). The stacking gel was run at 60 volts for about 1 hr and the running gel at 120 volts for 2 hrs. Proteins were transferred to nitrocellulose (BA85) in Towbin's buffer (Towbin, H. et al. (1979) Proc. Natl. Acad. Sci. USA 76:4350–4354) in an IDEA Scientific GENIE Blotter at about 1 A and about 24 V for about 1 to 2 hr at 4° C. The nitrocellulose was briefly fixed in Towbin's buffer and then blocked for 1 hr at room temperature in Tris-buffered saline (TBS: 50 mM Tris.HCl, 0.15 M NaCl, pH7.5) with 5% nonfat, dry milk (NFDM; Carnation). After blocking, it was washed 3 times (20 min. each) with TBS+0.5% NFDM+0.5% Nonidet P-40 (detergent) before incubating overnight 4° C. with anti-insecticidal protein antibodies. After primary antibody incubation, the nitrocellulose was again washed 3 times (20 min. each) with TBS+0.5% NFDM+0.5% sodium dodecyl sulfate (SDS). It was then incubated with goat anti-rabbit antibody alkaline phosphatase labelled (1:4000) for 2 hr at room temperature. Again, the nitrocellulose was washed for 20 min. in TBS+0.5% NFDM+0.5% SDS, followed by 2 additional washes (10 min. each) with TBS+0.5% NFDM+ and 0.05% Tween. The nitrocellulose was rinsed quickly three times in $MgCl_2$ buffer (0.1 M Tris HCl, pH8.8, 0.1 M NaCl, and 5 mM $MgCl_2$) and then developed with 0.15 mg/ml 5-bromo-4-chloroinoxylphosphate/nitrobluetetrazolium substrate (Knecht, D. A. and Dimond, R. L. (1984) Anal. Biochem. 136:180–184; Blake, M. S. et al. (1984) Anal. Biochem. 136:175–179). Extracts of control tissues were spiked with protoxin and/or toxin during extraction to estimate recovery during the western procedure. This showed that often insecticidal protein did not completely solubilize. As little as 0.01 ng of toxin was routinely detected on the blot. In 'spiked' samples, about 10 ng of standard was added to typical UC82 extract (from 100 mg tissue); the resultant signal on the blot represented about 30% recovery.

15.6 Bioassays

Bioassays were the most sensitive assay for the detection of *Bacillus thuringiensis* insecticidal protein. Two types of bioassays were conducted on putative transgenic plants. In the first, leaves were excised and placed in petri plates containing moistened filter paper. A predetermined number of first instar *Manduca sexta* (tobacco hornworm) larva were then added. This assay facilitated observations on Manduca and enabled larger numbers of samples to be tested. Substantial differences were observed between some varieties. However, results on a given $R_0$ or $R_1$ plant were not always consistent, due to either instability of insecticidal protein in excised leaves, or possible feeding of worms on moistened filter paper. In the second type of bioassay, first instar or, preferably, neonatal hornworms just hatched form eggs (eggs from Carolina Biological Supply) were placed on plants in the greenhouse, and checked daily for growth and mortality after 7 to 9 days. Problems with this assay included worms leaving tomato plants and dying of desiccation due to high greenhouse temperatures ("wandering worms") and difficulties in finding hornworms on the tomato plants. These problems were adjusted for with control plant data, in which less than 20% mortality was consistently observed. "Wandering worms" were further controlled by placing the plants and worms in netted cages.

15.7 Nucleic Acid Analysis

Southern and Northern blot analyses were done using standard techniques well-known to the art.

15.8 Results $R_0$ plants were regenerated from pH450, pH576, pH577, pH578, pH582, and pH585 transformations and $R_1$ plants from pH450, pH576, and pH578 transformations (see Table 13). Kanamycin-resistant tissues were obtained from all transformations. Bud initials existed on transformations of most vectors (Table 12). $R_0$ plants from both pH578 and pH577 transformations that have been selected on 40 mg/l geneticin (equivalent to 400 mg/l kanamycin) gave high octopine signals.

Initially, many $R_0$ plants from transformations with pH450 were infertile due to long-term tissue culture. This was evident from increased flowering and fruit set was observed in $R_0$ plants from pH578 and pH577 transformations, which were cultured for less time. In addition, cuttings from some older $R_0$ plants from pH450 transformations also showed improved fruit set. This improvement may also be in response to improved greenhouse conditions.

Two independent pH450 hypocotyl transformants yielded octopine-positive, G418-resistant tissues that regenerated plants containing octopine and *B. thuringiensis* insecticidal protein. Results from ELISA assays indicated insecticidal protein at levels ranging from 0.6 μg/g to 2.1 μg/g total protein. A substantial decrease in both total protein in the leaf and in insecticidal protein (μg/g total protein) was associated with plant age. Substantial degradation occurred, and in Western blots all ELISA-positive samples show smearing starting at about 110 kd.

ELISAs were used to screen putative transformants for high expression of *Bacillus thuringiensis* insecticidal protein. Detectable levels (greater than 5 ng insecticidal protein per g leaf tissue) were observed in transformed plants from pH450, pH577, and pH578, and $R_1$ plants of pH577 and pH582 transformations. All ELISA-positive plants tested killed some *Manduca sexta* larvae in bioassays (Table 13).

Western blots were used to determine the form of insecticidal protein expressed (protoxin or toxin) and to quantify the level of expression more precisely. In pH450 transformants, which contain the full-length *Bacillus thuringiensis* insecticidal protein structural gene, both protoxin and toxin was observed in leaf tissues. Tissues from pH577 and pH578 transformed plants also had both forms of the insecticidal protein. Different forms of insecticidal protein (protoxin and toxin) was also observed in different regenerated plants from what initially appeared to be a single transformation event.

Results for many of the plants assayed by bioassay are listed in Table 13. Further analysis (not shown) by analysis of variance (ANOV) and Duncan's multiple range test showed significant differences at the 1% level. Transformed plants from pH450 and pH577 gave the best biological activity. Decreases in biological activity of transformed plants as a function of plant and leaf age were also observed. Control plants (UC82 $R_0$ plants and UC82 plants grown from seed) all gave low rates of mortality (less than 25%). It was significant that on several of the $R_1$ plants with lower Manduca mortality, the worm weights were significantly lower than controls. In addition, *M. sexta* larvae that failed to die immediately on *B. thuringiensis* insecticidal protein-containing plants also failed to grow at normal growth rates. These differences were clearly apparent after 2 weeks.

Southern analysis showed that insertions of T-DNA containing the plant-expressible insecticide gene were present in the expected organization, and are usually present in low copy number (about 1 to 2 copies/haploid genome). In all plants positive for protein and in bioassays positive plants tested, insecticidal protein sequences were observed in Northern blots of polyadenylated RNA. However, most of this mRNA was shorter than expected.

The $R_0$ regenerated plants transformed by pH450 were marginally fertile. Southern, northern, octopine (Aeerts, M. et al. (1979) Plant Sci. Lett. 17:43–50) and protein analysis indicated that the insecticide gene and flanking vector sequences were inherited in mendelian fashion. Moreover, $R_1$ progeny plants gave positive results in bioassay, demonstrating that the capacity of the transformed plants to affect *Manduca sexta* is not restricted to regenerated plants.

Both bioassays and ELISAs of kanamycin-resistant pH577 and pH578 transformants indicated presence of insecticidal protein (Table 11). The pH578 regenerates were clearly transgenic plants, as indicated by octopine assays as well as kanamycin or G418 resistance. However, the inability to detect insecticidal protein in some transformants could be due to several reasons, e.g., a lack of assay sensitivity.

Example 16

Potato Transformation Procedure 16.1 Plant Material

Virus-free in vitro potato (*Solanum tuberosum*) plantlets of cultivars Kennebec, Superior, Atlantic, centennial Russet and Russet Norkotah were obtained from the University of Wisconsin, Department of Plant Pathology, Madison, Wis. Russet Burbank Virus-free plantlets were obtained from the Potato Virus Research laboratory at Colorado State University, Ft. Collins, Colo. Hybrid Homestead seeds were purchased from Park Seed Company, Greenwood, S.C. Russet Norkotah tubers were purchased from Deircks and Sons Inc., White Lake, Wis.

16.2 Bacterial Strains

Agrobacterium tumefaciens LBA4404, EHA101s and Z707s strains were used for potato tissue infection. Gene constructs in these strains were pH615, pH619, pH623, pH624, and pH627. Bacteria was grown on YEP media with 250 mg/l streptomycin and 200 mg/l erythromycin for 24 hours at 28° C. then suspended in MS liquid media prior to tissue inoculation.

16.3 Tissue Culture Media

Shoot induction medium consisted of MS salts (Murashige, T. and Skoog, F. (1962) Physiol. Plant 15:478–497), 1.0 mg/l thiamine, 0.5 mg/l nicotinic acid, 0.5 mg/l pyridoxine, 100 mg/l myo-inositol and 3% sucrose supplemented with 0.87 mg/l IAA aspartic acid (Research Organics) and 1.76 mg/l zeatin riboside (Sigma). Hormones were added prior to autoclaving. The pH was adjusted to 5.8 with 0.1 M KOH and the media was solidified with 7 g/l Tonomeko agar. Shoot induction media containing carbenicillin at 500 mg/l and kanamycin at 25 mg/l was used for selection of transformed shoots. Stock plantlets were grown on MS basal media without hormones in magenta GA7 containers (Magenta Corp.) and subcultured every 4 weeks. Shoot elongation and rooting media consisted of MS basal media with 25 mg/l kanamycin.

16.4 Procedure

Both stem and tuber tissue were used for transformation. Tubers were peeled and surface sterilized in 10% liquid bleach for 15 min under constant agitation. A 0.7 cm in diameter cork borer was used to make cores through the tuber. These cores were then sectioned into 2 to 3 mm thick discs and then inoculated (Sheerman, S. and Bevan, M. B. (1988) Plant Cell Rep. 7:13–16). Stem sections approximately 0.5 cm were made from in vitro grown stock plants 2 to 3 weeks after subculture. All sections containing axillary buds were discarded. Stem or tuber tissues were immediately soaked in $10^6$, $10^7$, or $10^8$ $ml^{-1}$ *Agrobacterium tumefaciens* cells for 5 to 10 minutes. They were then placed on sterile filter paper discs over *Nicotiana tabacum* feeder layers (Horsch, R. B. et al. (1985) Science 227:1229–1231) over shoot induction medium without antibiotics. They were cocultivated for 2 days then rinsed in liquid MS media containing 500 mg/l carbenicillin, blotted on sterile cardboard and transferred to shoot induction media with carbenicillin 500 mg/l. After 4 to 5 days the stem segments or tuber discs were placed on shoot induction media containing 25 mg/l kanamycin and 500 mg/l carbenicillin. Cultures were transferred every 3 weeks. Buds began to appear in 4 to 6 weeks and continued to form for several weeks thereafter. Shoots were excised and rooted on MS media with 25 mg/l kanamycin, then tested for gene expression.

16.5 Results

Thirty-three Russet Burbank plants regenerated from tissues inoculated with *A. tumfaciens* (pH615) were selected on 25 mg/l kanamycin. Three of these plants were tested for expression of *B. thuringiensis* insecticidal protein by ELISA; two were negative and one was positive. The insecticidal protein was expressed at a level of 5 ng/mg total protein. This plant also tested positive for NPT2 by ELISA. The plant DNA was then assayed by Southern analysis and tested positive for both insecticidal protein and NPT2. The DNA was also probed with a small section of the bacterial DNA (vir) to test for Agrobacterium contamination; none was present. A total of 7 Hybrid Homestead plants resulting from inoculations with pH624 and 4 Russet Burbank plants from inoculations with the pH627 have now been selected on kanamycin. Nine Kennebec plants regenerated after inoculations with the pH623 construct have also been selected.

Example 17

Cotton Transformation

*Agrobacterium tumefaciens* strain LBA4404 (Hoekema, A. et al. (1983) Nature 303:179–180) carrying a binary vector (either pH576, pH577, pH578, pH582, or pH585) was cultured on YEP (10 m/l yeast extract, 10 g/l peptone, 5 g/l NaCl) medium containing 250 µg/ml streptomycin and 25 µg/ml kanamycin (both from Sigma) for selection and solidified with agar. Bacteria were scraped off the agar medium, suspended in a $G_2$ medium (MS salts (Bibco) (Murashige, T. and Skoog, F. (1962) Plant Physiol. 15:474–497), 100 mg/l myo-inositol, 0.4 mg/l thiamine.HCL, 5 mg/l 2iP, 0.1 mg/l NAA (all from Sigma), 30 g/l glucose, pH 5.9) to a concentration of about $10^8$ cells/ml and were used for inoculation of cotyledon segments.

Cotton was transformed essentially as disclosed by Firoozabady, E. et al. (1987) Plant Mol. Biol. 10:105–116, and Firoozabady, E. U.S. patent application Ser. No. 076,339. Cotyledon pieces (approximately 0.5 $cm^2$ surface area) from sterile 12 to 14-day old coker 201 seedlings were dipped in *A. tumfaciens* liquid cultures in Petri dishes and gently shaken for a few seconds to ensure contact of all cotyledon edges with the bacterial cultures. The cotyledon pieces were then blotted dry and plated on Whatman #1 filter paper on a callus initiation $G_2$ medium containing 0.2% Gel-rite (Kelco). After three days cocultivation at low temperature (25° C.) and 16 h/day photoperiod at 90 $\mu E \cdot m^{-2} \cdot s^{-1}$ light, cotyledon pieces were transferred to Petri plates without the filter paper containing the same medium supplemented with 500 mg/l carbenicillin and 25 mg/l kanamycin sulphate (both from U.S. Biochemicals).

After 7–10 days of incubation, cotyledon pieces initiated transformed kanamycin-resistant microcalli (0.5 mm) at wound sites, while no callus from control untreated tissues or from tissues treated with LBA4404 grew on kanamycin. Two to three weeks later, 2–4 mm calli were excised from original explants and transferred to fresh medium and incubated at 10 $\mu E \cdot m^{-2} \cdot s^{-1}$ light. Most calli (90–95%) were kanamycin-resistant and most kanamycin-resistant calli (75–90%) were positive when tested for octopine. Calli were placed on embryogenic callus induction medium $G_3$ ($G_3 = G_2$ but with 0.1 mg/l 2iP and 5 mg/l NAA) for two weeks and then placed and maintained on embryogenic medium $G_0$ (same as $G_2$ with no hormones) under selection. Mature somatic embryos were transferred to lower ionic strength medium, GRMgn (modified from the medium of Stewart, J. M. and Hsu, C. L. (1977) Planta 137:113–177, by the addition of 0.01 mg/l NAA, and 0.1 mg/l GA, and use of 5 g/l glucose instead of sucrose). Plants were shown to be transformed by their resistance to kanamycin by production of callus from leaf tissue in the presence of kanamycin, production of octopine, ELISA for NPT2 and by DNA hybridization, and western immunoblot and analyses. Plants were transferred to soil for further analysis. The whole process from infection until transgenic plants were transferred to soil took about 6 to 8 months.

TABLE 1

Insects susceptible to *B. thuringiensis* insecticidal protein

COLEOPTERA

*Popillia japonica* (Japanese beetle)
*Sitophilus granarius* (granary weevil)
DIPTERA

*Aedes aegypti* (yellow-fever mosquito)
*A. atlanticus*
*A. cantans*
*A. capsius*
*A. cinereus*
*A. communis*
*A. detritus*
*A. dorsalis*
*A. dupreei*
*A. melanimon*
*A. nigromaculis* (pasture mosquito)
*A. punctor*
*A. sierrensis* (western treehole mosquito)
*A. sollicitans* (brown salt marsh mosquito)
Aedes sp.
*A. taeniorhynchus* (black. salt marsh mosquito)
*A. tarsalis*
*A. tormentor*
*A. triseriatus*
*A. vexans* (inland floodwater mosquito)
*Anopheles crucians*
*A. freeborni*
*A. quadrimaculatus* (common malaria mosquito)
*A. sergentii*
*A. stephensi*
Anopheles sp.
*Chironomus plumosus* (Chironomus: midges, biting)
Chironomus sp.
*C. tummi*
*Culex erraticus*
*C. inornata*
*C. nigripalus*
*C. peus*
*C. pipiens* (northern house mosquito)
*C. quinquefasciatus* (*C. pipiens fatigans*) (southern house mosquito)
*C. restuans*
Culex sp.
*C. tritaeniorhynchus*
*C. tarsalis* (western encephalitis mosquito)
*C. territans*
*C. univittatus*
*Culiseta incidens* (Culiseta: mosquitos)
*C. inornata*
Diamessa sp.
Dixa sp. (Dixa: midges)
*Eusimulium* (Simulium) *latipes* (Eusimulium: gnats)
*Goeldichironomus holoprasinus*
*Haematobia irritans* (horn fly)
*Hippelates collusor*
*Odagmia ornata*
*Pales pavida*
Polpomyia sp. (Polpomyia: midges, biting)
Polypedilum sp. (Polypedilum: midges)
*Psorophora ciliata*
*P. columiae* (confinnis) (Florida Glades mosquito, dark rice field mosquito)
*P. ferox*
*Simulium alcocki* (Simulium: black flies)
*S. argus*
*S. cervicornutum*
*S. damnosum*

TABLE 1-continued

Insects susceptible to *B. thuringiensis* insecticidal protein

*S. jenningsi*
*S. piperi*
*S. tescorum*
*S. tuberosum*
*S. unicornutum*
*S. venustum*
*S. verecundum*
*S. vittatum*
*Uranotaenia inguiculata*
*U. lowii*
*Wyeomyia mitchellii* (Wyeomyia: mosquitos)
*W. vanduzeei*
HYMENOPTERA

*Athalia rosae* (as colibri)
*Nematus* (Pteronidea) *ribesii* (imported currantworm)
*Neodiprion banksianae* (jack-pine sawfly)
*Priophorus tristis*
*Pristiphora erichsonii* (larch sawfly)
LEPIDOPTERA

*Achaea janata*
*Achroia grisella* (lesser wax moth)
*Achyra rantalis*
*Acleris variana* (black-headed budworm)
Acrobasis sp.
*Acrolepia alliella*
*Acrolepiopsis* (Acrolepia) *assectella*
*Adoxophyes orana* (apple leaf roller)
*Aegeria* (Sanninoidea) *exitiosa* (peach tree borer)
*Aglais urticae*
*Agriopsis* (Erannis) *aurantiaria* (Erannis: loopers)
*A.* (E.) *leucophaearia*
*A. marginaria*
*Agrotis ipsilon* (as ypsilon) (black cutworm)
*A. segetum*
*Alabama argillacea* (cotton leafworm)
*Alsophila aescularia*
*A. pometaria* (fall cankerworm)
*Amorbia essigana*
*Anadevidia* (Plusia) *peponis*
*Anisota senatoria* (orange-striped oakworm)
*Anomis flava*
*A.* (Cosmophila) *sabulifera*
*Antheraea pernyi*
*Anticarsia gemmatalis* (velvetbean caterpillar)
*Apocheima* (Biston) *hispidaria*
*A. pilosaria* (pedaria)
*Aporia crataegi* (black-veined whitemoth)
*Archips argyrospilus* (fruit-tree leaf roller)
*A. cerasivoranus* (ugly-nest caterpillar)
*A. crataegana*
*A. podana*
*A.* (Cacoecia) *rosana*
*A. xylosteana*
*Arctia caja*
*Argyrotaenia mariana* (gray-banded leaf roller)
*A. velutinana* (red-banded leaf roller)
*Ascia* (Pieris) *monuste orseis*
*Ascotis selenaria*
*Atteva aurea* (alianthus webworm)
*Autographa californica* (alfalfa looper)
*A.* (Plusia) *gamma*
*A. nigrisigna*
*Autoplusia egena* (bean leaf skeletonizer)
*Azochis gripusalis*
*Bissetia steniella*
*Bombyx mori* (silkworm)
*Brachionycha sphinx*
*Bucculatrix thurberiella* (cotton leaf perforator)
*Bupolus piniarius* (Bupolus: looper)
*Cacoecimorpha pronubana*
*Cactoblastis cactorum*
*Caloptilia* (Gracillaria) *invariabilis*
*C.* (G) *syringella* (lilac leaf miner)
*C.* (G.) *theivora*

TABLE 1-continued

Insects susceptible to *B. thuringiensis* insecticidal protein

*Canephora asiatica*
*Carposina niponensis*
Ceramidia sp.
*Cerapteryx graminis*
*Chilo auricilius*
*C. sacchariphagus indicus*
*C. suppressalis* (rice stem borer)
*Choristoneura fumiferana* (spruce budworm)
*C. murinana* (fir-shoot roller)
*Chrysodeixis* (Plusia) *chalcites*
*Clepsis spectrana*
*Cnaphalocrocis medinalis*
*Coleotechnites* (Recurvaria) *milleri* (lodgepole needle miner)
*C. nanella*
*Colias eurytheme* (alfalfa caterpillar)
*C. lesbia*
*Colotois pennaria*
*Crambus bonifatellus* (fawn-colored lawn moth, sod webworm)
*C. sperryellus*
Crambus spp.
*Cryptoblabes gnidiella*
*Cydia funebrana*
*C.* (Grapholitha) *molesta* (oriental fruit moth)
*C.* (Laspeyresta) *pomonella* (codling moth)
*Datana integerrima* (walnut caterpillar)
*D. ministra* (yellow-necked caterpillar)
*Dendrolimus pini*
*D. sibiricus*
*Depressaria marcella* (a webworm)
*Desmia funeralis* (grape leaf folder)
*Diachrysia* (Plusia) *orichalcea* (a semilooper)
*Diacrisia virginica* (yellow woollybear)
*Diaphania* (Margaronia) *indica*
*D. nitidalis* (pickleworm)
*Diaphora mendica*
*Diatraea grandiosella* (southwestern corn borer)
*D. saccharalis* (sugarcane borer)
*Dichomeris marginella* (juniper webworm)
*Drymonia ruficornis* (as chaonia)
Drymonia sp.
*Dryocampa rubicunda*
*Earias insulana*
*Ectropis* (Boarmia) *crepuscularia*
*Ennomos subsignarius* (elm spanworm)
*Elphestia* (Cardra) *cautella* (almond moth)
*E. elutella* (tobacco moth)
*E.* (Anagasta) *kuehniella* (Mediterranean flour moth)
*Elpinotia tsugana* (a skeletonizer)
*Epiphyas postvittana*
*Erannis defoliaria* (mottled umber moth)
*E. tiliaria* (linden looper)
*Erinnysis ello*
*Eriogaster henkei*
*E. lanestris*
*Estigmene acrea* (salt marsh caterpillar)
*Eublemma amabilis*
*Euphydryas chalcedona*
*Eupoecilia ambiguella*
*Euproctis chrysorrhoea* (*Nygmi phaeorrhoea*) (brown tail moth)
*E. fraterna*
*E. pseudoconspersa*
*Eupterote fabia*
*Eutromula* (Simaethis) *pariana*
*Euxoa messoria* (dark-sided cutworm)
*Galleria mellonella* (greater wax moth)
*Gastropacha quercifolia*
*Halisdota argentata*
*H. caryae* (hickory tussock moth)
*Harrisina brillians* (western grape skeletonizer)
*Hedya nubiferana* (fruit tree tortrix moth)
*Heliothis* (Helicoverpa) *armigera* (Heliothis = Chloridea) (gram pod borer)
*H.* (H.) *assulta*
*Heliothis peltigera*

TABLE 1-continued

Insects susceptible to *B. thuringiensis* insecticidal protein

*H. virescens* (tobacco budworm)
*H. viriplaca*
*H. zea* (cotton bollworm, corn earworm, soybean podworm, tomato fruitworm, sorghum headworm, etc.)
*Hellula undalis* (cabbage webworm)
*Herpetogramma phaeopteralis*
*Heterocampa guttivitta* (saddled prominent)
*H. manteo* (variable oak leaf caterpillar)
*Holcocera pulverea*
*Homoeosoma electellum* (sunflower moth)
*Homona magnanima*
*Hyloicus pinastri*
*Hypeuryntis coricopa*
*Hyphantria cunea* (fall webworm)
*Hypogymna morio Itame* (Thamnonoma) *wauaria* (a spanworm)
*Junonia coenia* (buckeye caterpillars)
*Kakivoria flavofasciata*
*Keiferia* (Gnorimoschema) *lycopersicella* (tomato pinworm)
*Lacanobia* (Polia) *oleracea*
*Lamdina athasaria pellucidaria*
*L. fiscellaria fiscellaria* (hemlock looper)
*L. fisellaria lugubrosa*
*L. fiscellaria somniaria*
*Lampides boeticus*
*Leucoma* (Stilpnotia) *salicis* (satin moth)
*L. wiltshirei*
*Lobesia* (=Polychrosis) *botrana*
*Loxostege commixtalis* (alfalfa webworm)
*L. sticticalis* (beet webworm)
*Lymantria* (Porthetria) *dispar* (gypsy moth) (Lymantria: tussock moths)
*L. monacha* (nun-moth caterpillar)
*Malacosoma americana* (eastern tent caterpillar)
*M. disstria* (forest tent caterpillar)
*M. fragilis* (=fragile) (Great Basin tent caterpillar)
*M. neustria* (tent caterpillar, lackey moth)
*M. neustria* var. *testacea*
*M. pluviale* (western tent caterpillar)
*Mamerstra brassicae* (cabbage moth)
*Manduca* (Inotoparce) *quinquemaculata* (tomato hornworm)
*M. (I.) sexta* (tobacco hornworm)
*Maruca testulalis*
*Melanolophia imitata*
*Mesographe forficalis*
*Mocis repanda* (Mocis: semilooper)
*Molippa sabina*
*Monema flavescens*
*Mythimna* (Pseudaletia) *unipuncta* (armyworm)
*Nephantis serinopa*
*Noctua* (Triphaena) *pronuba*
*Nomophila noctuella* (lucerne moth)
*Nymphalis antiopa* (mourning-cloak butterfly)
*Oiketicus moyanoi*
*Ommatopteryx texana*
*Operophtera brumata* (winter moth)
*Opsophanes* sp.
*O. fagata*
*Orgyia* (Hemerocampa) *antiqua*
*O. leucostigma* (white-marked tussock moth)
*O. (H.) pseudotsugata* (Douglas-fir tussock moth)
*O. thyellina*
*Orthosia gothica*
*Ostrinia* (Pyrausta) *nubilaiis* (European corn borer)
*Paleacrita vernata* (spring cankerworm)
*Pammene juliana*
*Pandemis dumetana*
*P. pyrusana*
*panolis flammea*
*Papilio cresphontes* (orange dog)
*P. demoleus*
*P. philenor*
*Paralipsa* (Aphemia) *gularis*
*Paralobesia viteana*
*Paramyelois transitella*
*Parnara guttata*
*Pectinophora gossypiella* (pink bollworm)
*Pericallia ricini*
*Peridroma saucia* (variegated cutworm)
*Phalera bucephala*
*Phlogophora meticulosa*
*Phryganidia californica* (California oakworm)
*Phthorimaea* (=Gnorimoschema) *operculella* (potato tuberworms)
*Phyllonorycter* (Lithocolletis) *blancardella*
*Pieris brassicae* (large white butterfly)
*P. canidia sordida*
*P. rapae* (imported cabbageworm, small white butterfly)
*Plathypena scabra* (green cloverworm)
*Platynota* sp.
*P. stultana*
*Platyptilia carduidactyla* (artichoke plume moth)
*Plodia interpunctella* (Indian-meal moth)
*Plutella xylostella* as *maculipennis* (diamondback moth)
*Prays citri* (citrus flower moth)
*P. oleae* (olive moth)
*Pseudoplusia includens* (soybean looper)
*Pygaera anastomosis*
*Rachiplusia ou*
*Rhyacionia buoliana* (European pine shoot moth)
*Sabulodes caberata*
*Samia cynthia*
*Saturnia pavonia*
*Schizura concinna* (red-humped caterpillar)
*Schoenobius bipunctifer*
*Selenephera lunigera*
*Sesamia inferens*
*Sibine apicalis*
*Sitotroga cerealella* (Angoumois grain moth)
*Sparganothis pilleriana*
*Spilonota* (Tmeocera) *ocellana* (eye-spotted budmoth)
*Spilosoma lubricipeda* (as menthastri)
*S. virginica*
*Spilosoma* sp.
*Spodoptera* (Prodenia) *eridania* (southern armyworm)
*S. exigua* (beet armyworm, lucerne caterpillar)
*S. frugiperda*
*S. littoralis*
*S. litura*
*S. mauritia*
*S. (P.) ornithogalli* (yellow-striped armyworm)
*S. (P.) praefica*
*Syllepte derogata*
*S. silicalis*
*Symmerista canicosta*
*Thaumetopoea pityocampa* (pine processionary caterpillar)
*T. processionea*
*T. wauaria* (currant webworm)
*T. wilkinsoni*
*Thymelicus lineola* (European skipper)
*Thyridopteryx ephemeraeformis* (bagworm)
*Tineola bisselliella* (webbing clothes moth)
*Tortrix viridana* (oak tortricid)
*Trichoplusia ni* (cabbage looper)
*Udea profundalis* (celery leaf tier)
*U. rubigalis*
*Vanessa cardui* (painted-lady)
*V. io*
*Xanthopastis timais*
*Xestia* (Amathes, Agrotis) *c-nigrum* (spotted cutworm)
*Yponomeuta cognatella* (= *Y. evonymi*) (Yponomeuta = Hyponomeuta)
*Y. evonymella*
*Y. mahalebella*
*Y. malinella* (small ermine moth)
*Y. padella* (small ermine moth)
*Y. rorrella*
*Zeiraphera diniana*
MALLOPHAGA

*Bovicola bovis* (cattle biting louse)
*B. crassipes*
*B. limbata*

TABLE 1-continued

Insects susceptible to *B. thuringiensis* insecticidal protein

*B. ovis*
*Lipeurus caponis* (wing louse)
*Menacnathus stramineus*
*Menopon gallinae* (shaft louse)
TRICHOPTERA

*Hydropsyche pellucida*
*Potamophylax rotundipennis*

TABLE 2

Plants recommended for protection by *B. thuringiensis* insecticidal protein

| | | |
|---|---|---|
| alfalfa | escarole | potatoes |
| almonds | field corn | radishes |
| apples | filberts | rangeland |
| artichokes | flowers | raspberries |
| avocados | forage crops | safflower |
| bananas | forest trees | shade trees |
| beans | fruit trees | shingiku |
| beets | garlic | small grains |
| blackberries | grapes | soybeans |
| blueberries | hay | spinach |
| broccoli | kale | squash |
| brussels sprouts | kiwi | stonefruits |
| cabbage | kohlrabi | stored corn |
| caneberries | lentils | stored grains |
| carrots | lettuce | stored oilseeds |
| cauliflower | melons | stored peanuts |
| celery | mint | stored soybeans |
| chard | mustard greens | stored tobacco |
| cherries | nectarines | strawberries |
| chinese cabbage | onions | sugarbeets |
| chrysanthemums | oranges | sugar maple |
| citrus | ornamental trees | sunflower |
| collards | parsley | sweet corn |
| cos lettuce | pasture | sweet potatoes |
| cotton | peaches | tobacco |
| cranberries | peanuts | tomatoes |
| crop seed | pears | turf |
| cucumbers | peas | turnip greens |
| currants | pecans | walnuts |
| dewberries | peppers | watermelons |
| eggplant | pome fruit endive | |
| pomegranite | | |

TABLE 3

Varieties of *B. thuringiensis* alesti
aizawai
canadensis
dakota
darmstadiensis
dendrolimus
entomocidus
finitimus
fowleri
galleriae
indiana
israelensis
kenyae
kurstaki
kyushuensis
morrisoni
ostriniae
pakistani
sotto
thompsoni

TABLE 3-continued

Varieties of *B. thuringiensis* thuringiensis
tolworthi
toumanoffi
wuhanensis

TABLE 4

Index of plasmids and strains

| Strain or Plasmid | Constructed or used in Example | See Figure | Made From (α Comments) |
|---|---|---|---|
| *A. tumefaciens* | 6 | | (ubiquitous) |
| *A. rhizogenes* | 5 | | (also see background) |
| *B. thuringiensis* var. *kurstaki* HD-73 | 1.1 | 1 | |
| ColE1 | 2.5 | | |
| *E. coli* GM33 | 2.3 | | |
| *E. coli* HB101 | 1.1 | | |
| *E. coli* JM103 | 2.1 | | |
| *E. coli* K802 | 2.2 | | |
| MBT3 | 3.3 | | M13mp8, p123/58-10 |
| MBT3 (Nco) | 3.4 | | MBT3 |
| MBT14 | 3.3 | | M13mp8, p123/58-10 |
| mWB2344 | 2.1 | | |
| M13-Bt-A | 2.1 | | mWB2344, p123/58-10 |
| M13-Bt-A (Bam) | 2.1 | | M13-Bt-A |
| M13-Bt-S | 2.1 | | mWB2344, p123/58-10 |
| M13mp7 | 3.1 | | |
| M13mp8 | 3.3 | | |
| M13-PpBt | 4.4 | | MBT3(Nco), M13-3.8Ab |
| M13-1 | 3.1 | | M13mp7, pNS5 |
| M13-3 | 3.1 | | M13mp7, pNS5 |
| M13-3A/B18a | 3.2 | | M13-3 |
| M13-3.8A | 4.1 | | M13mp7, 177.4 |
| M13-3.8Aa | 4.2 | | M13-3.8Ac |
| M13-3.8Ab | 4.3 | | M13-3.8Aa |
| M13-3.8Ac | 4.2 | | M13-3.8A |
| M13-3.8S | 4.1 | | M13mp7, 177.4 |
| pBR322 | 1.1 | | M13mp7, 177.4 |
| PCF44 | 3.1 | | pBR322, pTiC58 |
| pCF44A | 3.1 | | pCF44 |
| pKS-proI | 2.2 | 3 | pKS111, = pTR-proI |
| pKS-proI | 2.2 | 2.2 | pKS-proI |
| pKS-4 | 2.5 | 2 | pBR322, pRZ102 |
| pKS111 | 2.2, 12.3 | 2, 3 | pRK290, pTi15955 |
| pKS111-K | 4.5 | | pKS4(pRZ102), pKS111 |
| pKS111-N | 3.5 | | pCF44, pKS111-K |
| pKS111-NpBt | 3.5 | | MBT3(Nco), M13-3A/B18a |
| pKS111-N pKS111-PpBt | 4.5 | | M13-PpBt, pKS111-K |
| pNS5 | 3.1 | | pBr322, pCF44A |
| pPH1J1 | 9 | | |
| pRK290 | 2.2, 9 | | |
| pRK2013 | 9 | | |
| pRZ102 | 2.5 | | ColE1, Tn5 |
| pTiA66 | 2.4 | | |
| pTi15955 | 2.4 | 2 | |
| p8.8 | 4.1 | | pBR322, 177.4 |
| p11-83a | 2.3 | 3 | pKSK-proI(Bam) |

TABLE 4-continued

Index of plasmids and strains

| Strain or Plasmid | Constructed or used in Example | See Figure | Made From (α Comments) |
|---|---|---|---|
| p11-83b | 2.3 | 3 | pKS-4 p11-83a, M13-Bt-A (Bam) |
| p123/58-3 | 1.1 | 1 | B. thuringiensis var. kurstaki HD-73 pBR322 |
| p123/58-10 | 1.1 | 1 | B. thuringiensis var. kurstaki HD-73 pBR322 |
| p403 | 2.2 | 2 | pBR322, pTi15955 |
| "1.6" | 2.2 | 2 | (= transcript 24, see also Detailed Description) |
| 177.4 | 4.1 | | Charon 24A, P. vulparis cv. Tendergreen |
| pBt73-161 | 11.1 | | B. thuringiensis var. kurstaki Hd-73 pBR322 |
| pBt73-10 (Bam) | 11.2 | | p123/58-10 |
| pBt73-16 | 11.2 | 4 | pBt73-10 (Bam), pBt73-161 |
| pTR-proI | 12.1 | 4 | = pKS-proI |
| pTR-proI(Bam) | 12.1 | 4 | pTR-proI |
| pBR325 | 12.3 | 4 | |
| pBR325aBB | 12.3 | 4 | pBR325 |
| p403B | 12.1 | 4 | pBR325aBB, pTR-proI (Bam) |
| M13mp19 | 12.4 | 4 | |
| 1.6.4 | 12.4 | 4 | M13mp19, pBt73-16 |
| 1.6.4B-3.8.3 | 12.4 | 4 | 1.6.4 |
| p403B/BTB 3 | 12.3 | 4 | 1.6.4B-3.8.3, p403B |
| pH4-1 | 12.1 | | pSUP106, pTi15955, CaMV, Tn5 |
| pH400 | 12.1 | | pH4-1 |
| pDOB412 | 12.2 | | CaMV, pBR322 |
| pDOB512 | 12.2 | | pDOB412 |
| p403BRL1 | 12.3 | | p403B |
| pDOB514 | 12.3 | | pDOB513 |
| pMAN514 | 12.3 | | p403BRL1, pDOB514 |
| pKS4.2 | 12.3 | | pKS4 |
| pKS4.3 | 12.3 | | pKS4.2 |
| pBR322Bam | 12.3 | | pBR322, lambda |
| p11-83c | 12.3 | | pKS4.3, pBR322 Bam⁻ |
| pCJ161 | 12.5 | | 1.6.4B-3.8.3, pCG116 |
| pH450 | 12.6 | | pCJ161, pH400 |
| pCG116 | 12.3 | | p11-83c, pTR-proI (Bam) |

TABLE 5

Deposited Strains

| NRRL B-4488 | B. thuringiensis var. kurstaki HD-73 |
| NRRL B-15394 | E. coli C600 (pKS-4) |
| NRRL B-11371 | E. coli HB101 |
| NRRL B-12014 | E. coli RR1 (pBR322) |
| ATCC 37017 | pBR322 |
| ATCC 15955 | A. tumefaciens (pTi15955) |
| NRRL B-15393 | E. coli HB101 (p8.8) |

TABLE 5-continued

Deposited Strains

| NRRL B-15612 | E. coli HB101 (p123/58-10) |
| NRRL B-5759 | E. coli HB101 (pBT73-16) |
| NRRL B-18009 | E. coli K802 (pH4-1) |
| NRRL B-15486 | E. coli CSH52 (pSUP106) |

TABLE 6

MS Medium

| $NH_4NO_3$ | 1.65 | g/l |
| $KNO_3$ | 1.9 | g/l |
| $CaCl_2 \cdot 2H_2O$ | 440 | mg/l |
| $MgSO_4 \cdot 7H_2O$ | 370 | mg/l |
| $KH_2PO_4$ | 170 | mg/l |
| KI | 0.83 | mg/l |
| $H_3BO_3$ | 6.2 | mg/l |
| $MnSO_4 \cdot 4H_2O$ | 22.3 | mg/l |
| $ZnSO_4 \cdot 7H_2O$ | 8.6 | mg/l |
| $Na_2MoO_4 \cdot 2H_2O$ | 0.25 | mg/l |
| $CuSO_4 \cdot 5H_2O$ | 0.025 | mg/l |
| $CoCl_2 \cdot 6H_2O$ | 0.025 | mg/l |
| $Na_2$ EDTA | 37.23 | mg/l |
| $FeSO_4 \cdot 7H_2O$ | 27.85 | mg/l |
| Inositol | 1 | g/l |
| Nicotinic acid | 50 | mg/l |
| Pyroxidine HCl | 50 | mg/l |
| Thiamine HCl | 50 | mg/l |
| Sucrose | 30 | g/l |
| Agar | 8 | g/l |

TABLE 7

| | Experiment 1[5] | | Experiment 2[6] | |
|---|---|---|---|---|
| Clone | $A_{492}$[1] | CP[2] | $A_{492}$ | CP |
| 100 | 0.17 ± 0.03[7] | + | 0.14 | + |
| 101 | 0.02 ± 0.01 | − | 0.07 | ± |
| 102 | 0.06 ± 0.02 | ± | 0.21 | + |
| 103 | 0.00 ± 0.00 | − | ND | ND |
| 104 | ND[3] | ND | 0.11 | + |
| 105 | 0.00 ± 0.00 | − | 0.10 | + |
| 106 | 0.10 ± 0.02 | + | 0.01 | − |
| 107 | 0.06 ± 0.03 | ± | 0.06 | − |
| 109 | 0.11 ± 0.05 | + | 0.03 | − |
| 110 | 0.06 ± 0.01 | ± | 0.13 | + |
| 111 | 0.12 ± 0.02 | + | 0.00 | − |
| NX[4] | -0- | | -0- | |

[1]Average of three ELISA determinations. Absorbance at 492 nm, corrected by subtracting the value for the NX control.
[2]Rated as having (+) or not having (−) crystal protein. ± indicates a marginal rating.
[3]Not Determined.
[4]Untransformed Nicotiana tabacum var. "Xanthi" control. In experiments 1 and 2, respectively, 18 and 19 control leaves obtained from different plants were averaged.
[5]Experiment 1 was standardized for equal tissue wet weight.
[6]Experiment 2 was standardized for equal plant protein concentrations.
[7]± standard error of the mean.

TABLE 8

| Clone Number | Replicate Number | Total Larvae | Dead Larvae |
|---|---|---|---|
| 100 | 1 | 4 | 1 |
| | 2 | 5 | 0 |
| | 3 | 5 | 4 |
| 103 | 1 | 5 | 0 |
| | 2 | 5 | 0 |

TABLE 8-continued

| Clone Number | Replicate Number | Total Larvae | Dead Larvae |
|---|---|---|---|
|  | 3 | 5 | 0 |
| 106 | 1 | 5 | 0 |
|  | 2 | 5 | 0 |
|  | 3 | 5 | 0 |
| 109 | 1 | 5 | 2 |
|  | 2 | 5 | 0 |
|  | 3 | 5 | 3 |
| 111 | 1 | 5 | 2 |
|  | 2 | 5 | 1 |
|  | 3 | 5 | 0 |

TABLE 9

| Clone Number | Replicate Number | Total Larvae | Dead Larvae |
|---|---|---|---|
| 100 | 1 | 4 | 2 |
|  | 2 | 4 | 3 |
|  | 3 | 6 | 3 |
| 103 | 1 | 6 | 0 |
|  | 2 | 6 | 2 |
|  | 3 | 6 | 2 |
| 106 | 1 | 6 | 2 |
|  | 2 | 8 | 3 |
|  | 3 | 10 | 6 |
| 109 | 1 | 14 | 2 |
|  | 2 | 6 | 1 |
|  | 3 | 6 | 4 |
| 111 | 1 | 6 | 3 |
|  | 2 | 6 | 2 |
|  | 3 | 6 | 3 |

TABLE 10

| Callus #* | Treatment | ELISA Assays NPT2 | ELISA Assays NPT2 Btt | Southern Blots IG Probe | Southern Blots Probe |
|---|---|---|---|---|---|
| 5-1 | Fusion-High | − | − | − | − |
| 5-2 | Fusion-High | + | + | + | + |
| 5-3 | Fusion-High | − | ND | ND | ND |
| 19-1 | Fusion-Low | − | + | ND | ND |
| 20-1 | Fusion-High | − | + | + | + |
| 20-2 | Fusion-High | + | − | + | + |
| 20-3 | Fusion-High | − | + | + | + |
| 34-1 | Fusion-Low | − | ND | + | + |
| 35-1 | Fusion-High | + | + | + | + |
| EG5 | Neg. Control | − | − | − | − |

ND = not determined
*Only 9 of the 10 kanamycin resistant "Fusion" calli produced sufficient callus tissue for these analyses.

TABLE 11

| Callus # | Exp. 1 | Exp. 2 |
|---|---|---|
| 6-1 | + | + |
| 6-3 | − | − |
| 6-4 | ND | − |
| 6-9 | + | ND |
| 6-11 | − | − |
| 6-12 | + | + |
| 6-18 | + | + |
| 6-19 | + | + |
| 6-21 | + | − |
| 6-23 | + | + |
| 6-32 | + | − |
| 21-3 | − | − |

TABLE 11-continued

| Callus # | Exp. 1 | Exp. 2 |
|---|---|---|
| 21-4 | − | − |
| 21-5 | − | − |
| 21-8 | − | − |
| 21-9 | − | − |
| 21-12 | + | − |
| 21-13 | − | − |
| 21-16 | − | − |
| 21-19 | − | − |
| 21-26 | − | − |
| 36-1 | − | − |
| 36-3 | − | − |
| 36-4 | − | − |
| 36-12 | − | − |
| 36-14 | − | − |
| 36-17 | − | − |
| 36-25 | − | − |

ND = not determined

TABLE 12

Transformation of *Lycopersicum esculentum* Hypocotyl and Leaf Disc Tissues with Various Binary Vectors

| Transforming Plasmid | Hypocotyl Tissue Percent Transformed | Hypocotyl Tissue Percent Transformed w/buds | Leaf Tissue Percent Transformed | Leaf Tissue Percent Transformed w/buds |
|---|---|---|---|---|
| pH450 | 19 (178)[a] | 9 (34) | 0.17 (1189) | 100 (2) |
| pH575 | 9 (180) | 29 (17) | 5 (640) | 0 |
| pH576 | 21 (123) | 19 (26) | 5 (1993) | 0 |
| pH577 | 11 (282) | 22 (32) | 1 (1430) | 42 (12) |
| pH578 | 9 (136) | 58 (12) | 4 (820) | 23 (31) |
| pH582 | 9 (97) | 0 |  |  |
| pH585 | 11.5 (104) | 25 (12) |  |  |

[a](number)

TABLE 13

Summary of Bioassays and ELISAs on Tomato

| Plant* | Gen | Plant age months | Percent mortality (n) | % worm weight | ELISA |
|---|---|---|---|---|---|
| UC82 | (F$_1$) | <6 | 13 (385) | 100 | − |
| UC82 | (R$_0$) | <6 | 17 (50) | 91 | − |
| V7R | (F$_1$) | <6 | 23 (30) | 118 | − |
| V7R | (R$_0$) | <6 | 19 (11) | 78 | − |
| pH450-7 | (R$_0$) | <6 | 73 (55) | 77 | + |
|  |  | >6 | 39 (36) | 86 | + |
| pH450-13 | (R$_0$) | <6 | 35 (20) | 29 | + |
| pH450-19 | (R$_0$) | <6 | 70 (20) | 32 | + |
| pH450-1-1a | (R$_1$) | <6 | 50 (38) | 20 | + |
| pH450-2-3a | (R$_1$) | <6 | 17 (18) | 91 | − |
| pH450-2-5a | (R$_1$) | <6 | 10 (10) | 55 | − |
| pH450-2-5b | (R$_1$) | <6 | 22 (9) | 38 | − |
| pH450-4-1c | (R$_1$) | <6 | 78 (9) | 69 | + |
| pH450-4-2e | (R$_1$) | <6 | 78 (18) | 40 | + |
|  |  | >6 | 46 (13) | 120 | + |
| pH450-4-2f | (R$_1$) | <6 | 50 (14) | 32 | + |
| pH577-3a | (R$_0$) | <6 | 74 (46) | 19 | + |
| pH577-3c | (R$_0$) | <6 | 80 (20) | 15 | + |
| pH577-3d | (R$_0$) | <6 | 40 (10) | 39 | NA |
| pH577-3g-1 | (R$_0$) | <6 | 85 (20) | 8 | + |
| pH577-3g-2 | (R$_0$) | <6 | 65 (30) | 19 | + |
| pH577-3g-4 | (R$_0$) | <6 | 19 (16) | 43 | NA |
| pH577-3g-7 | (R$_0$) | <6 | 60 (20) | 20 | NA |
| pH577-17-5 | (R$_0$) | <6 | 38 (32) | 61 | + |
| pH577-17-6 | (R$_0$) | <6 | 0 (10) | 80 | − |
| pH577-21b | (R$_0$) | <6 | 30 (10) | 60 | NA |
| pH578-6-1b | (R$_0$) | <6 | 65 (23) | 89 | + |

TABLE 13-continued

Summary of Bioassays and ELISAs on Tomato

| Plant* | Gen | Plant age months | Percent mortality (n) | % worm weight | ELISA |
|---|---|---|---|---|---|
| pH578-6-2c | (R$_0$) | <6 | 0 (14) | 65 | − |
| pH578-15-10 | (R$_0$) | <6 | 67 (30) | 47 | + |

*All plants except UC82 and V7R are octopine positive and kanamycin resistant.
NA = not assayed.

We claim:

1. A method of providing insecticidal protein insects harmful to plants comprising:
   (a) transforming a plant cell capable of regeneration to contain a *Bacillus thuringiensis* crystal protein insecticide structural gene and a plant expressible promoter whereby the gene is expressible in the plant cell under control of the promoter;
   (b) regenerating said plant cell to form plant tissue expressing said gene in insecticidal amounts; and
   (c) allowing insects to feed on said insecticidal plant tissue whereby they are provided insecticidal protein.

2. A plant cell capable of regeneration, wherein the plant cell is transformed with a nucleic acid encoding a *Bacillus thuringiensis* crystal endotoxin under control of a promoter such that said endotoxin is expressed in insecticidal amounts in plant tissue regenerated from said cell.

3. The plant cell of claim 2 which is a tomato plant cell.

4. The plant cell of claim 2, wherein said endotoxin is a full-length *Bacillus thuringiensis* crystal endotoxin.

5. The plant tissue regenerated from the plant cell of claim 2, wherein the tissue expresses said protein in insecticidal amounts.

6. The plant regenerated from the plant cell of claim 2, or a progeny of said plant, wherein the plant or progeny expresses said protein in insecticidal amounts.

7. A plant cell comprising a nucleic acid encoding a *Bacillus thuringiensis* endotoxin or endotoxin fragment, wherein said nucleic acid is under the control of a promoter functional in said plant cell, wherein said endotoxin or endotoxin fragment is expressed at a level rendering said cell toxic to an insect.

8. A dicotyledonous plant cell comprising a nucleic acid encoding a *Bacillus thuringiensis* endotoxin or endotoxin fragment, wherein said nucleic acid is under the control of a promoter functional in said plant cell, wherein said endotoxin or endotoxin fragment is expressed at a level rendering said cell toxic to an insect.

9. A plant cell comprising a nucleic acid encoding a *Bacillus thuringiensis* var. *kurstaki* endotoxin or endotoxin fragment, wherein said nucleic acid is under the control of a promoter functional in said plant cell, wherein said endotoxin or endotoxin fragment is expressed at a level rendering said cell toxic to an insect.

10. A dicotyledonous plant cell comprising a nucleic acid encoding a *Bacillus thuringiensis* var. *kurstaki* endotoxin or endotoxin fragment, wherein said nucleic acid is under the control of a promoter functional in said plant cell, wherein said endotoxin or endotoxin fragment is expressed at a level rendering said cell toxic to an insect.

11. A dicotyledonous plant cell comprising a nucleic acid encoding a *Bacillus thuringiensis* var. *kurstaki* HD-1 endotoxin or endotoxin fragment, wherein said nucleic acid is under the control of a promoter functional in said plant cell, wherein said endotoxin or endotoxin fragment is expressed at a level rendering said cell toxic to an insect.

12. A dicotyledonous plant cell comprising a nucleic acid encoding a *Bacillus thuringiensis* var. *kurstaki* HD-73 endotoxin or endotoxin fragment, wherein said nucleic acid is under the control of a promoter functional in said plant cell, wherein said endotoxin or endotoxin fragment is expressed at a level rendering said cell toxic to an insect.

13. The plant cell of claim 8 or 9 which is a tomato plant cell.

14. The plant cell of claim 7, 8, 9, or 10 in which the endotoxin is full-length.

15. Insect-resistant plant tissue comprising the plant cell of claim 2, 7, 8, 9 or 10.

16. An insect resistant plant comprising the plant cell of claim 2, 7, 8, 9, or 10 and the insect-resistant progeny of said plant, wherein the progeny comprises the nucleic acid.

17. A method for providing insecticidal proteins to insects harmful to plants comprising the steps of cultivating a plant comprising the tissue of claim 15, and allowing insects to ingest said tissue.

18. The plant cell of claim 2 or 7, wherein said cell is rendered toxic to an insect belonging to an insect order selected from the group consisting of Lepidoptera, Coleoptera, Diptera, Hymenoptera, Mallophaga, and Trichoptera.

19. A plant regenerated from a plant cell which is susceptible to transformation by *Agrobacetrium tumefaciens*, wherein the plant cell is transformed with a nucleic acid encoding a *Bacillus thuringiensis* crystal protein of approximately 130–135 kD, and wherein the nucleic acid is under control of a promoter such that said protein is expressed in said plant in amounts insecticidal to Lepidopteran insects.

20. A plant regenerated from a plant cell which is susceptible to transformation by *Agrobacetrium tumefaciens*, wherein the plant cell is transformed with a nucleic acid encoding a *Bacillus thuringiensis* endotoxin, wherein the nucleic acid is under control of a promoter, and wherein said endotoxin is expressed in said plant in amounts insecticidal to Lepidopteran insects.

21. A plant cell comprising a nucleaic acid encoding a *Bacillus thuringiensis* endotoxin or endotoxin fragment, wherein said endotoxin or endotoxin fragments is expressed at a level rendering such cell toxic to an insect, said cell being capable of undergoing mitosis to yield a second plant cell comprising said nucleic acid, wherein said endotoxin or endotoxin fragments, is expressed at a level rendering said second plant cell toxic to an insect.

22. The plant cell of claim 21, wherein said cell is of a dicot species.

23. A tomato plant which has been regenerated from a tomato plant cell transformed to comprise a nucleic acid encoding a *Bacillus thuringiensis* crystal protein of approximately 130 kD, wherein the nucleic acid is under control of a promoter such that said protein is expressed in said plant in amounts insecticidal to Lepidopteran insects.

* * * * *

UNITED STATES PATENT AND TRADEMARK OFFICE
CERTIFICATE OF CORRECTION

PATENT NO. : 6,943,282 B1
APPLICATION NO. : 07/713624
DATED : September 13, 2005
INVENTOR(S) : Michael J. Adang and John D. Kemp It is certified that error appears in the above-identified patent and that said Letters Patent is hereby corrected as shown below:

Column 5:
Lines 5-6, "use of. Ti" should read --use of Ti--.

Column 9:
Lines 54-55, "Merlo (1082) *supra*" should read --Merlo (1982) *supra*--.

Column 18:
Line 28, "may be in Planta" should read --may be in planta--.

Column 28:
Line 58, "ligated-with" should read --ligated with--.

Column 29:
Line 51, "digested with XhaI" should read --digested with XhoI--.

Column 34:
Line 20, "109 bacteria" should read --$10^9$ bacteria--.

Column 35:
Line 21, "8 x 103 cells/ml" should read --8 x $10^3$ cells/ml--.

Column 35:
Line 43, "6.3 Regenerator of Plants" should read --6.3 Regeneration of Plants--.

Column 43:
Line 66, "107-108 ml-l" should read --$10^7$-$10^8$ ml$^{-1}$--.

Column 65:
Line 55, "Ostrinia (Pyrausta) nubilaiis" should read "Ostrinia (Pyrausta) nubialis--.

Column 73:
Line 14, "insecticidal protein insects" should read -- insecticidal protein to insects--.

Column 73:
Line 24, "provided insecticidal protein" should read --provided insecticidal proteins--.

Column 74:
Line 46, "nucleaic acid" should read --nucleic acid--.

UNITED STATES PATENT AND TRADEMARK OFFICE
CERTIFICATE OF CORRECTION

PATENT NO. : 6,943,282 B1
APPLICATION NO. : 07/713624
DATED : September 13, 2005
INVENTOR(S) : Michael J. Adang and John D. Kemp It is certified that error appears in the above-identified patent and that said Letters Patent is hereby corrected as shown below:

<u>Column 74</u>:
Line 48, "endotoxin fragments" should read --endotoxin fragment--.

<u>Column 74</u>:
Line 52, "endotoxin fragments" should read --endotoxin fragment--.

Signed and Sealed this

First Day of August, 2006

JON W. DUDAS
*Director of the United States Patent and Trademark Office*

EX PARTE REEXAMINATION CERTIFICATE (13015th)

United States Patent
Adang et al.

(10) Number: US 6,943,282 C1
(45) Certificate Issued: Aug. 20, 2025

(54) INSECT RESISTANT PLANTS

(75) Inventors: Michael J. Adang, Madison, WI (US); John D. Kemp, Las Cruces, NM (US)

(73) Assignee: Corteva Agriscience LLC

Reexamination Request:
No. 90/019,306, Nov. 27, 2023

Reexamination Certificate for:
Patent No.: 6,943,282
Issued: Sep. 13, 2005
Appl. No.: 07/713,624
Filed: Jun. 10, 1991

Certificate of Correction issued Aug. 1, 2006

Related U.S. Application Data

(63) Continuation of application No. 07/260,574, filed on Oct. 21, 1988, now abandoned, which is a continuation-in-part of application No. 06/848,733, filed on Apr. 4, 1986, now abandoned, which is a continuation-in-part of application No. 06/535,354, filed on Sep. 26, 1983, now abandoned.

(51) Int. Cl.
C07K 14/235 (2006.01)
C07K 14/325 (2006.01)
C12N 15/82 (2006.01)

(52) U.S. Cl.
CPC ........ *C07K 14/325* (2013.01); *C12N 15/8216* (2013.01); *C12N 15/8286* (2013.01); *Y02A 40/146* (2018.01)

(58) Field of Classification Search
None
See application file for complete search history.

(56) References Cited

To view the complete listing of prior art documents cited during the proceeding for Reexamination Control Number 90/019,306, please refer to the USPTO's Patent Electronic System.

*Primary Examiner* — Lora E Barnhart Driscoll

(57) ABSTRACT

A method for expressing insecticidal protein structural genes in plant genomes is provided. In the preferred embodiments this invention comprises placing a structural gene for the *Bacillus thuringiensis* crystal protein under control of a plant or a T-DNA promoter and ahead of a polyadenylation site followed by insertion of said promoter/structural gene combination into a plant genome by utilizing an *Agrobacterium tumefaciens* Ti plasmid-based transformation system. The modified Ti plasmid is then used to transform recipient plant cells. Also provided are the plants and tissues produced by this method and bacterial strains, plasmids, and vectors useful for execution of this invention.

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1-23 is confirmed.

* * * * *